United States Patent
Kim et al.

(10) Patent No.: US 8,957,102 B2
(45) Date of Patent: Feb. 17, 2015

(54) HETEROCYCLIC COMPOUND AS PROTEIN KINASE INHIBITOR

(75) Inventors: Tae-Seong Kim, Daejeon (KR); Eunkyung Lee, Daejeon (KR); Doyoung Kim, Daejeon (KR); Bu-mahn Park, Daejeon (KR); Jiyeon Park, Daejeon (KR); JungJe Joo, Daejeon (KR)

(73) Assignee: Neopharm Co., Ltd. (KR)

( * ) Notice: Subject to any disclaimer, the term of this patent is extended or adjusted under 35 U.S.C. 154(b) by 785 days.

(21) Appl. No.: 12/920,243

(22) PCT Filed: Aug. 28, 2009

(86) PCT No.: PCT/KR2009/004830
§ 371 (c)(1),
(2), (4) Date: Aug. 30, 2010

(87) PCT Pub. No.: WO2010/044543
PCT Pub. Date: Apr. 22, 2010

(65) Prior Publication Data
US 2011/0183983 A1    Jul. 28, 2011

(30) Foreign Application Priority Data
Oct. 14, 2008 (KR) .................. 10-2008-0100522

(51) Int. Cl.
*C07D 231/00* (2006.01)
*C07D 231/06* (2006.01)
*A01N 43/42* (2006.01)
*A01N 43/56* (2006.01)
*A61K 31/44* (2006.01)
*A61K 31/415* (2006.01)
*C07D 471/04* (2006.01)
*C07D 487/04* (2006.01)

(52) U.S. Cl.
CPC ............ *C07D 471/04* (2013.01); *C07D 487/04* (2013.01)
USPC ..... 514/404; 514/300; 548/366.1; 548/379.1; 546/112

(58) Field of Classification Search
None
See application file for complete search history.

(56) References Cited

U.S. PATENT DOCUMENTS

2008/0234268 A1    9/2008   Booker et al.
2008/0312232 A1   12/2008   Kim et al.

FOREIGN PATENT DOCUMENTS

KR    10-2008-0004617        1/2008
WO    WO2006/116713 A1  *    2/2006
WO    2008/052974           5/2008

OTHER PUBLICATIONS

Gherardi et al. "Targeting MET in cancer: rationale and progress", Nature Rev. Cancer, 2012, vol. 12, pp. 89-103.*
Hage et al. "The novel c-Met inhibitory cabozantinib overcomes gemcitabine resistance and stem cell signaling in pancreatic cancer", Cell Death and Disease, 2013, vol. 4, e627.*
Longbin Liu, et al, "Discovery of a Potent, Selective, and Orally Bioavailable c-Met Inhibitor: 1-(2-Hydroxy-2methylpropyl)-N-(5-(7-methoxyquinolin-4-yloxy)pyridin-2-yl)-5-methyl-3-oxo-2-phenyl-2,3-dihydro-1H-pyrazole-4-carboxamide" Journal of Medical Chemistry, 2008, pp. 3688-3691, vol. 51, No. 13, American Chemical Society.
Yihong Zhang, et al., "Identification of a Novel Recepteur d'Origine Nantais/c-Met Small-Molecule Kinase Inhibitor with Antitumor Activing in vivo", Cancer Res, 2008, pp. 6680-6687, vol. 68, No. 16, www.aacrjournals.org.
International Search Report—PCT/KR2009/004830 dated Apr. 22, 2010.

* cited by examiner

*Primary Examiner* — Jeffrey S Lundgren
*Assistant Examiner* — Stephanie Springer
(74) *Attorney, Agent, or Firm* — Cantor Colburn LLP

(57)  ABSTRACT

Provided are novel heterocyclic compounds useful as anti-cancer drugs by suppressing protein kinase activities of growth factor receptors such as c-Met, pharmaceutical compositions containing the same, and methods for using the compound.

11 Claims, No Drawings

HETEROCYCLIC COMPOUND AS PROTEIN KINASE INHIBITOR

TECHNICAL FIELD

The present invention relates to novel heterocyclic compounds which are useful as an anti-cancer drug by suppressing protein kinase activity of growth factor receptors such as c-Met. Also, pharmaceutical compositions containing the compound is useful in treating diseases other than cancer, related to signal transduction pathways operated through receptors of growth factors and neo-vascularization, for example, c-Met.

BACKGROUND ART

Since protein kinases which phosphorylate specific amino acids of proteins, are closely involved in various signal transduction in cells and disease mechanisms, inhibition of such kinases have been an important therapeutic target.

The protein kinases represent a large group of proteins playing critical roles in regulating various cellular processes for maintenance and control of cellular functions. They include abl, Akt, AXL, bcr-abl, Blk, Brk, Btk, c-kit, c-Met, c-src, c-fms, CDK1, CDK2, CDK3, CDK4, CDK5, CDK6, CDK7, CDK8, CDK9, CDK10, cRafl, CSFlR, CSK, DDR1, DDR2, EGFR, ErbB2, ErbB3, ErbB4, Erk, Fak, fes, FGFR1, FGFR2, FGFR3, FGFR4, FGFR5, Fgr, flt-1, flt-3, flt-4, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes and Zap70.

It is known that some protein kinases are closely related to uncontrolled vascularization, such asocular neovascularization, retinopathy (including diabetic retinopathy), age-related macular degeneration, psoriasis, hemangioblastoma, angioma, arteriosclerosis, inflammatory diseases, such as a rheumatoid, rheumatic inflammatory diseases including rheumatoid arthritis, or other chronic inflammatory diseases such as chronic asthma, post-transplantation atherosclerosis, endometriosis, and other neoplastic diseases, including solid tumor and liquid tumor. With regard to a lot of pathological disorders and diseases during embryonic development and normal growth, an angiogenic factor known as vascular endothelial growth factor (VEGF, originally known as "vascular permeability factor (VPR)") and its receptor play a critical role in the regulation of growth and differentiation of the vascular system and its components.

VEGF is a disulfide-linked, 46-kDa dimeric glycoprotein related to "platelet-derived growth factor (PDGF)". It is produced in normal and tumor cells, is an endothelial cell-specific mitogen, exhibits angiogenic activity in in vivo tests (e.g. in the rabbit cornea), is chemotactic for endothelial cells and monocytes, and induces plasminogen activating factor in endothelial cells, which is involved in degradation of protein in the cellular matrix during neovascularization of capillary vessels. A number of VEGF isoforms are known that exhibit biological activity comparable to VEGF but are secreted from different cells and have different heparin-binding abilities. Further, "placental growth factor (PlGF)" and VEGF-C are included in the VEGF family.

VEGF receptors (VEGFR) are transmembranous receptors of tyrosine kinase. They are characterized by seven extracellular immunoglobulin-like domains and an intracellular tyrosine kinase domain. Several VEGF receptors, such as VEGFR-1 (also known as flt-1), VEGFR-2 (also known as KDR) and VEGFR-3 are known.

In a lot of human tumors, especially in glioma and carcinomas, VEGF and VEGF receptors are expressed in high levels. This has led to the hypothesis that the VEGF released by tumor cells stimulates the growth of blood capillaries and proliferation of tumor endothelium in a paracrine manner and, through the improved blood supply, accelerates the tumor growth. Increased VEGF expression could explain the occurrence of cerebral edema in patients with glioma. A direct evidence of the role of VEGF as a tumor angiogenesis factor in vivo is shown in studies in which VEGF expression or VEGF activity was inhibited.

Angiogenesis is regarded as a necessary requirement for tumors to grow beyond a diameter of about 1-2 mm. Up to this limit, oxygen and nutrients may be transported to the tumor cells by diffusion. Every tumor, regardless of its origin and cause, is thus dependent on angiogenesis for its growth after it has reached a certain size.

Three principal mechanisms are important in the activity of angiogenesis inhibitors against tumors. They are: 1) inhibition of the growth of vessels, especially capillary vessels, into avascular resting tumors, with the result that there is no net tumor growth because of the balance that is activated between cell death and proliferation; 2) prevention of the migration of tumor cells owing to the absence of blood flow to and from tumors; and 3) inhibition of endothelial cell proliferation, thus avoiding the paracrine growth-stimulating effect exerted on the surrounding tissue by the endothelial cells which normally line the blood vessels.

It is known that VEGFs are the only angiogenic growth factors contributing vascular hyperpermeability and the formation of edema. In fact, vascular hyperpermeability and edema appear to be mediated via VEGF production.

VEGF-mediated hyperpermeability can significantly contribute to disorders with excessive matrix deposition, aberrant stromal proliferation, fibrosis, and so forth. Therefore, regulators of angiogenesis have become an important therapeutic target.

Hepatocyte growth factor (HGF) also known as scatter factor plays an important role in the regeneration of liver cells. HGF is a mesenchyme-derived cytokine known to induce multiple pleiotropic responses in normal and neoplastic cells result in proliferation in both epithelial and endothelial cells, dissociation of epithelial colonies into individual cells, stimulation of motility (motogenesis) of epithelial cells, cell survival, induction of cellular morphogenesis, promotion of invasion, and all critical processes underlying metastasis. It is also reported that HGF promotes angiogenesis, and that it plays a critical role in tissue regeneration, wound healing and normal embryonic processes, all of which are dependent on both cell motility and proliferation.

Those physiological processes are initiated by HGF through high-affinity binding to its receptor, c-Met, an identified proto-oncogene. The ligand binding induces c-Met dimerization that results in an autophosphorylated activated receptor. Activation of c-Met promotes signal transduction cascades of transphosphorylation of key cytoplasmic tyrosine residues responsible for recruiting multiple effector proteins including the p85 subunit of PI3-kinase, phospholipase Cγ, Grb2 and Shc adaptor proteins, the protein phosphatase SHP2 and Gab1. Activation of other signaling molecules has been reported in HGF-stimulated cells, most notably Ras, MAP kinase, STAT, ERK-1, -2 and FAK which are involved in cell proliferation.

c-Met, also known as hepatocyte growth factor receptor (HGFR), is a membrane receptor molecule located in epithelial cells. It plays a critical role in the regulation of cell motility. HGF/SF is secreted in the liver, as well as in the lungs, kidneys and heart, when the organs are damaged. c-Met is expressed predominantly in epithelial cells but has also been identified in endothelial cells, myoblasts, hematopoietic cells and motor neurons. Overexpression of HGF and activation of c-Met have been associated with the onset and progression of a number of different tumor types as well as the promotion of metastatic diseases.

HGF and c-Met are overexpressed in various solid tumors, liver cancer, breast cancer, pancreatic cancer, lung cancer, renal cancer, bladder cancer, ovarian cancer, brain tumor, prostate cancer, gallbladder cancer, myeloma and many other diseases. Mutations of c-Met have also been identified in ovarian cancer, childhood HCC, gastric carcinoma, head and neck squamous cell carcinoma, non-small cell lung carcinoma and colorectal metastasis. In addition, further evidence supporting the role of c-Met in cancer is based on the overexpression of HGF and c-Met receptor in various tumors including thyroid, ovarian and pancreatic carcinomas. It has also been demonstrated to be amplified in liver metastasis of colorectal carcinoma. Generally, most human tumors and tumor cell lines of mesenchymal origin inappropriately express HGFR and/or HGF.

Numerous experimental data have demonstrated the role of HGF and c-Met in tumor invasion, growth, survival and progression ultimately leading to metastasis. In preclinical studies, transgenic expression of HGF results in a metastatic phenotype, and an amplified/overexpression c-Met spontaneously transforms NIH-3T3 cells. In addition, biological agents, such as ribozymes, antibodies and antisense RNAs targeting either HGF or c-Met have been shown to inhibit tumorigenesis. In this regard, the contents of Korean Patent Publication No. 10-2008-0004617 are incorporated hereto in its entirety by reference.

Thus, selective, small molecule kinase modulators targeting c-Met are expected to have therapeutic potential for the treatment of cancers in which c-Met receptor activation plays a critical role in the development and progression of primary tumors and secondary metastases. HGF is also known to regulate angiogenesis, a process critical in tumor growth and dissemination. Therefore, there is a potential for this class of modulators to impact angiogenesis-dependent diseases as well that may include, among others, diabetic retinopathy, macular degeneration, obesity and inflammatory disease such as rheumatoid arthritis.

Considering the role of HGF and/or c-Met, it is important to substantially suppress or inhibit the biological effect of HGF and/or its receptor in order to improve the aforesaid diseases or pathological conditions. Thus, a compound inhibiting HGF will be a useful compound. The compounds presented herein have never been described in regard to treatment of cancer as angiogenesis inhibitors nor treatment of cancer as c-Met inhibitors.

DETAILED DESCRIPTION OF THE INVENTION

Technical Problem

The object of the present invention is to provide novel heterocyclic compounds which are useful for, but not limited to, an anti-cancer drug by suppressing protein kinase activities of growth factor receptors such as c-Met, pharmaceutical compositions containing the same, and methods for using the compound. Also, the pharmaceutical compositions containing the compounds are useful in treating diseases other than cancer, related to signal transduction pathways operated through receptors of growth factors and anti-vascularization, for example, c-Met.

Technical Solution

The object of the present invention could be attained by novel heterocyclic compounds represented by Chemical Formula 1, which are useful as an anti-cancer drug by suppressing protein kinase activity of growth factor receptors such as c-Met.

The present invention relates to novel heterocyclic compounds represented by Chemical Formula 1, pharmaceutical compositions containing the compounds, and methods for using the compounds.

The present invention provides novel heterocyclic compounds represented by Chemical Formula 1, pharmaceutically acceptable salts thereof, stereoisomers (e.g. enantiomer, diastereomer, etc.) thereof or solvates thereof:

[Chemical Formula 1]

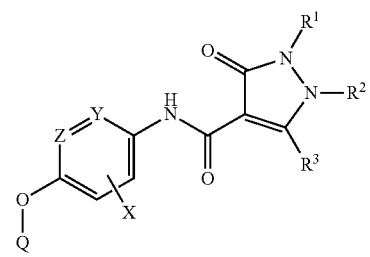

wherein $R^1$ is alkyl, substituted alkyl, cycloalkyl, substituted cycloalkyl, arylalkyl, substituted arylalkyl, aryl, substituted aryl, alkenyl, substituted alkenyl, alkynyl, substituted alkynyl, heteroaryl, substituted heteroaryl, heterocyclyl, substituted heterocyclyl, heteroarylalkyl, substituted heteroarylalkyl, heterocycloalkyl or substituted heterocycloalkyl;

$R^2$ is $C_1$-$C_6$ alkyl or substituted $C_1$-$C_6$ alkyl;

$R^3$ is alkyl, substituted alkyl, cycloalkyl, substituted cycloalkyl, arylalkyl, substituted arylalkyl, aryl, substituted aryl, alkenyl, substituted alkenyl, alkynyl, substituted alkynyl, heteroaryl, substituted heteroaryl, heterocyclyl, substituted heterocyclyl, heteroarylalkyl, substituted heteroarylalkyl, heterocycloalkyl or substituted heterocycloalkyl;

Q is unsaturated heterocyclyl fused from nitrogen-containing 5-membered unsaturated heterocyclyl and nitrogen-containing 6-membered unsaturated heterocyclyl;

X is hydrogen or halogen;

Y is CH or N; and

Z is CH or N.

The present invention further provides pharmaceutical compositions comprising therapeutically effective amounts of the compounds represented by Chemical Formula 1, pharmaceutically acceptable salts thereof, stereoisomers (e.g. enantiomer, diastereomer, etc.) thereof or solvates thereof in admixture with pharmaceutically acceptable carriers. The present invention further provides methods for treating cancer in a subject in need thereof, comprising administering pharmaceutically effective amounts of the compounds represented by Chemical Formula 1, pharmaceutically acceptable salts thereof, stereoisomers (e.g. enantiomer, diastereomer, etc.) thereof or solvates thereof to the subject and, optionally, administering one or more additional anti-cancer drug(s) to the subject.

Advantageous Effects

According to the present invention, there is provided a novel nitrogen-containing heterocyclic compound which is useful as an anti-cancer drug by suppressing protein kinase activity of growth factor receptors such as c-Met. A pharmaceutical composition containing the compound and a method for using the compound are useful in treating cancer. Also, they may useful in treating diseases related to signal transduction pathways operated through a receptor of growth factor and anti-vascularization, for example, c-Met.

BEST MODE FOR CARRYING OUT THE INVENTION

The present invention provides the novel heterocyclic compound represented by Chemical Formula 1 defined above, a pharmaceutical composition containing the compound, a method for preparing the compound and a method for using the compound.

The novel heterocyclic compound of the present invention includes a compound represented by Chemical Formula 1, a pharmaceutically acceptable salt thereof, a stereoisomer (e.g. enantiomer, diastereomer, etc.) thereof and a solvate thereof:

[Chemical Formula 1]

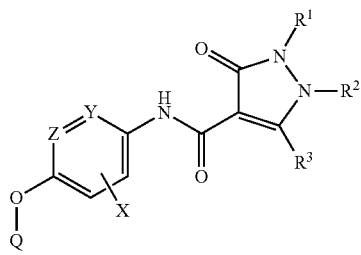

wherein $R^1$ is alkyl, substituted alkyl, cycloalkyl, substituted cycloalkyl, arylalkyl, substituted arylalkyl, aryl, substituted aryl, alkenyl, substituted alkenyl, alkynyl, substituted alkynyl, heteroaryl, substituted heteroaryl, heterocyclyl, substituted heterocyclyl, heteroarylalkyl, substituted heteroarylalkyl, heterocycloalkyl or substituted heterocycloalkyl;

$R^2$ is $C_1$-$C_6$ alkyl or substituted $C_1$-$C_6$ alkyl;

$R^3$ is alkyl, substituted alkyl, cycloalkyl, substituted cycloalkyl, arylalkyl, substituted arylalkyl, aryl, substituted aryl, alkenyl, substituted alkenyl, alkynyl, substituted alkynyl, heteroaryl, substituted heteroaryl, heterocyclyl, substituted heterocyclyl, heteroarylalkyl, substituted heteroarylalkyl, heterocycloalkyl or substituted heterocycloalkyl;

Q is unsaturated heterocyclyl fused from nitrogen-containing 5-membered unsaturated heterocyclyl and nitrogen-containing 6-membered unsaturated heterocyclyl;

X is hydrogen or halogen;

Y is CH or N; and

Z is CH or N.

The present invention includes the compounds represented by Chemical Formula 1, pharmaceutically acceptable salts thereof, stereoisomers (e.g. enantiomer, diastereomer, etc.) thereof, solvates thereof, prodrugs thereof, or the like.

In an embodiment of the present invention, Q is a radical represented by:

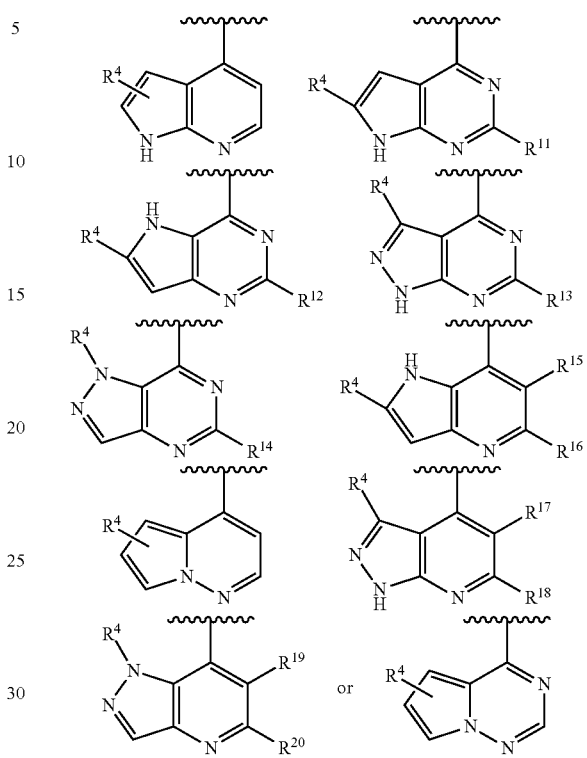

wherein $R^4$ is hydrogen, alkyl, substituted alkyl, cycloalkyl, substituted cycloalkyl, arylalkyl, substituted arylalkyl, halogen, aryl, substituted aryl, alkenyl, substituted alkenyl, alkynyl, substituted alkynyl, alkylcarbonyl, substituted alkylcarbonyl, hydroxyalkyl, substituted hydroxyalkyl, saturated or unsaturated heterocyclyl, substituted saturated or unsaturated heterocyclyl, saturated or unsaturated heterocyclyl-alkyl, or substituted saturated or unsaturated heterocyclyl-alkyl; and $R^{11}$, $R^{12}$, $R^{13}$, $R^{14}$, $R^{15}$, $R^{16}$, $R^{17}$, $R^{18}$, $R^{19}$ and $R^{20}$ are independently hydrogen, $C_1$-$C_6$ alkyl, $C_1$-$C_6$ alkoxy, —NH($C_1$-$C_6$ alkyl) or —NRR' (where R and R' are independently $C_1$-$C_6$ alkyl).

In an embodiment of the present invention, $R^1$ is $C_1$-$C_6$ alkyl, substituted $C_1$-$C_6$ alkyl, $C_2$-$C_6$ alkenyl, $C_2$-$C_6$ alkynyl, $C_3$-$C_7$ cycloalkyl, substituted $C_3$-$C_7$ cycloalkyl, $C_3$-$C_7$ heterocycloalkyl, $C_6$-$C_{10}$ aryl, substituted $C_6$-$C_{10}$ aryl, $C_5$-$C_{11}$ monocyclic or bicyclic heteroaryl, or substituted $C_5$-$C_{11}$ monocyclic or bicyclic heteroaryl. Specifically, in an embodiment of the present invention, $R^1$ is phenyl, substituted phenyl, naphthyl, substituted naphthyl, pyridyl, azepanyl, pyrazolyl, thiazolyl, indolyl, indazolyl, indenyl, cyclopropyl, isopropyl, phenylethyl, aminoalkyl, benzyl, amidoalkyl, morpholinyl or furanylmethyl.

More specifically, in an embodiment of the present invention, $R^1$ is phenyl, substituted phenyl, naphthyl, or substituted naphthyl, but is not limited thereto.

In another embodiment of the present invention, $R^3$ is $C_1$-$C_6$ alkyl, substituted $C_1$-$C_6$ alkyl, $C_6$-$C_{10}$ aryl or substituted $C_6$-$C_{10}$ aryl, but is not limited thereto.

In another embodiment of the present invention, X is halogen selected from the group consisting of F, Cl, Br and I, but is not limited thereto.

In another embodiment of the present invention, Q is

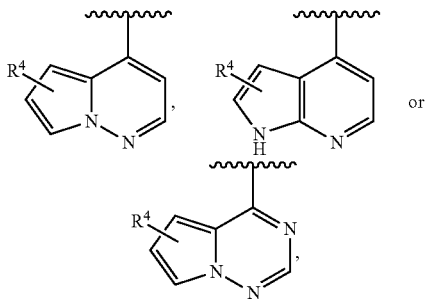

but is not limited thereto.

In an embodiment of the present invention, $R^4$ is hydrogen, halogen selected from the group consisting of F, Cl, Br and I, $C_1$-$C_6$ alkyl, substituted $C_1$-$C_6$ alkyl, $C_2$-$C_6$ alkenyl, $C_2$-$C_6$ alkynyl, $C_3$-$C_7$ cycloalkyl, substituted $C_3$-$C_7$ cycloalkyl, $C_6$-$C_{10}$ aryl, substituted $C_6$-$C_{10}$ aryl, $C_1$-$C_6$ alkylcarbonyl, substituted $C_1$-$C_6$ alkylcarbonyl, $C_1$-$C_6$ hydroxyalkyl, substituted $C_1$-$C_6$ hydroxyalkyl, 3- to 10-membered saturated or unsaturated heterocyclyl having one or more heteroatom(s) selected from the group consisting of N, S and O, or substituted 3- to 10-membered saturated or unsaturated heterocyclyl, but is not limited thereto.

Specifically, in an embodiment of the present invention, $R^4$ is hydrogen, halogen, phenyl, substituted phenyl, naphthyl, substituted naphthyl, pyridyl, substituted pyridyl, pyrazinyl, pyrimidinyl, azepanyl, pyrazolyl, thiazolyl, thiophenyl, isoxazolyl, substituted isoxazolyl, ethyl, acetyl, 1-hydroxyethyl, hydroxypropyl, cyclopropyl, isopropyl, aminoalkyl, benzyl, amidoalkyl, morpholinyl, furanylmethyl or piperidinyl, but is not limited thereto.

More specifically, in an embodiment of the present invention, $R^4$ is hydrogen, halogen, phenyl, substituted phenyl, naphthyl, substituted naphthyl, pyridyl, substituted pyridyl, pyrazinyl, pyrimidinyl, thiazolyl, thiophenyl, isoxazolyl, ethyl, acetyl, 1-hydroxyethyl, hydroxypropyl, substituted isoxazolyl or piperidinyl, but is not limited thereto.

In an embodiment of the present invention, $R^4$ is halogen, phenyl, or phenyl substituted with halogen or alkoxy, but is not limited thereto.

In another embodiment of the present invention, Q is

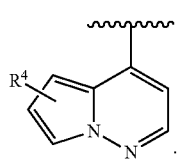

$R^4$ is independently selected from hydrogen, halogen, phenyl, substituted phenyl, naphthyl, substituted naphthyl, pyridyl, substituted pyridyl, pyrazinyl, pyrimidinyl, thiazolyl, thiophenyl, isoxazolyl, substituted isoxazolyl, ethyl, acetyl, 1-hydroxyethyl, hydroxypropyl, 5- or 6-membered saturated or unsaturated heterocyclyl having one or more heteroatom(s) selected from the group consisting of N, S and O, or substituted 5- or 6-membered saturated or unsaturated heterocyclyl, but is not limited thereto.

In an embodiment of the present invention, Q is

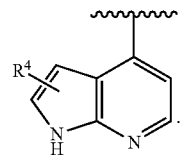

Herein, $R^4$ may be hydrogen, halogen, phenyl, substituted phenyl, naphthyl, substituted naphthyl or thiophenyl, but is not limited thereto.

In an embodiment of the present invention, Q is

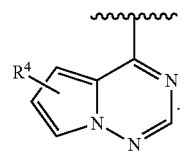

Herein, $R^4$ may be hydrogen, halogen, phenyl, substituted phenyl, naphthyl or substituted naphthyl, but is not limited thereto.

The present invention also relates to a compound selected from the following compounds, a pharmaceutically acceptable salt thereof, a stereoisomer (e.g. enantiomer, diastereomer, etc.) thereof and a solvate thereof:

N-(4-(5-bromopyrrolo[1,2-b]pyridazin-4-yloxy)-3-fluorophenyl)-1,5-dimethyl-3-oxo-2-phenyl-2,3-dihydro-1H-pyrazole-4-carboxamide;

N-(3-fluoro-4-(5-phenylpyrrolo[1,2-b]pyridazin-4-yloxo)phenyl)-1,5-dimethyl-3-oxo-2-phenyl-2,3-dihydro-1H-pyrazole-4-carboxamide;

N-(3-fluoro-4-(5-(4-fluorophenyl)pyrrolo[1,2-b]pyridazin-4-yloxy)phenyl)-1,5-dimethyl-3-oxo-2-phenyl-2,3-dihydro-1H-pyrazole-4-carboxamide;

N-(3-fluoro-4-(5-(4-methoxyphenyl)pyrrolo[1,2-b]pyridazin-4-yloxy)phenyl)-1,5-dimethyl-3-oxo-2-phenyl-2,3-dihydro-1H-pyrazole-4-carboxamide;

N-(3-fluoro-4-(5-(3-fluorophenyl)pyrrolo[1,2-b]pyridazin-4-yloxo)phenyl)-1,5-dimethyl-3-oxo-2-phenyl-2,3-dihydro-1H-pyrazole-4-carboxamide;

N-(3-fluoro-4-(5-(3-methoxyphenyl)pyrrolo[1,2-b]pyridazin-4-yloxy)phenyl)-1,5-dimethyl-3-oxo-2-phenyl-2,3-dihydro-1H-pyrazole-4-carboxamide;

N-(4-(5-bromopyrrolo[1,2-b]pyridazin-4-yloxy)-3-fluorophenyl)-2-(4-fluorophenyl)-1,5-dimethyl-3-oxo-2,3-dihydro-1H-pyrazole-4-carboxamide;

N-(3-fluoro-4-(5-phenylpyrrolo[1,2-b]pyridazin-4-yloxy)phenyl)-2-(4-fluorophenyl)-1,5-dimethyl-3-oxo-2,3-dihydro-1H-pyrazole-4-carboxamide;

1,5-dimethyl-3-oxo-2-phenyl-2,3-dihydro-1H-pyrazole-4-carboxylic acid [3-fluoro-4-(pyrrolo[1,2-b]pyridazin-4-yloxy)-phenyl]-amide;

1,5-dimethyl-3-oxo-2-phenyl-2,3-dihydro-1H-pyrazole-4-carboxylic acid [3-fluoro-4-(2-phenyl-1H-pyrrolo[2,3-b]pyridin-4-yloxy)-phenyl]-amide;

2-(4-fluoro-phenyl)-1,5-dimethyl-3-oxo-2,3-dihydro-1H-pyrazole-4-carboxylic acid [3-fluoro-4-(2-phenyl-1H-pyrrolo[2,3-b]pyridin-4-yloxy)-phenyl]-amide;

2-(4-fluoro-phenyl)-1,5-dimethyl-3-oxo-2,3-dihydro-1H-pyrazole-4-carboxylic acid

[3-fluoro-4-(3-phenyl-1H-pyrrolo[2,3-b]pyridin-4-yloxy)-phenyl]-amide;

N-(3-fluoro-4-(pyrrolo[1,2-f][1,2,4]triazin-4-yloxy)phenyl)-2-(4-fluorophenyl)-1,5-dimethyl-3-oxo-2,3-dihydro-1H-pyrazole-4-carboxamide;

N-(3-fluoro-4-(pyrrolo[1,2-f][1,2,4]triazin-4-yloxy)phenyl)-1,5-dimethyl-3-oxy-2-phenyl-2,3-dihydro-1H-pyrazole-4-carboxamide;

N-(3-fluoro-4-(6-phenylpyrrolo[1,2-f][1,2,4]triazin-4-yloxy)phenyl)-2-(4-fluorophenyl)-1,5-dimethyl-3-oxo-2,3-dihydro-1H-pyrazole-4-carboxamide;

N-(4-(6-chloropyrrolo[1,2-f][1,2,4]triazin-4-yloxy)-3-fluorophenyl)-2-(4-fluorophenyl)-1,5-dimethyl-3-oxo-2,3-dihydro-1H-Pyrazole-4-carboxamide;

N-(4-(6-chloropyrrolo[1,2-f][1,2,4]triazin-4-yloxy)-3-fluorophenyl)-1,5-dimethyl-3-oxo-2-phenyl-2,3-dihydro-1H-pyrazole-4-carboxamide;

N-(3-fluoro-4-(6-phenylpyrrolo[1,2-f][1,2,4]triazin-4-yloxy)phenyl)-1,5-dimethyl-3-oxo-2-phenyl-2,3-dihydro-1H-pyrazole-4-carboxamide;

N-(3-fluoro-4-(5-phenylpyrrolo[1,2-b]pyridazin-4-yloxy)phenyl)-1,2-dimethyl-3-oxo-5-phenyl-2,3-dihydro-1H-pyrazole-4-carboxamide;

N-(3-fluoro-4-(5-(pyridin-2-yl)pyrrolo[1,2-b]pyridazin-4-yloxy)phenyl)-2-(4-fluorophenyl)-1,5-dimethyl-3-oxo-2,3-dihydro-1-pyrazole-4-carboxamide;

N-(3-fluoro-4-(5-(thiophen-2-yl)pyrrolo[1,2-b]pyridazin-4-yloxy)phenyl)-2-(4-fluorophenyl)-1,5-dimethyl-3-oxo-2,3-dihydro-1H-pyrazole-4-carboxamide;

N-(3-fluoro-4-(5-(pyrimidin-5-yl)pyrrolo[1,2-b]pyridazin-4-yloxy)phenyl)-2-(4-fluorophenyl)-1,5-dimethyl-3-oxo-2,3-dihydro-1H-pyrazole-4-carboxamide;

N-(3-fluoro-4-(5-(thiazol-2-yl)pyrrolo[1,2-b]pyridazin-4-yloxy)phenyl)-2-(4-fluorophenyl-1,5-dimethyl-3-oxo-2,3-dihydro-1H-pyrazole-4-carboxamide;

N-(3-fluoro-4-(5-(pyrazin-2-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide;

N-(3-fluoro-4-(5-(piperidin-4-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide;

N-(3-fluoro-4-(5-(pyridin-3-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide;

N-(3-fluoro-4-(5-(pyridin-4-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide;

N-(3-fluoro-4-(5-(thiophen-3-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide;

N-(3-fluoro-4-(5-(3,5-dimethylisoxazol-4-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide;

N-(3-fluoro-4-(5-(6-methylpyridin-3-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide;

N-(3-fluoro-4-(5-(2-methylpyridin-4-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide;

N-(3-fluoro-4-(5-(1-hydroxyethyl)pyrrolo[1,2-b]pyridazin-4-yloxy)phenyl)-2-(4-fluorophenyl)-1,5-dimethyl-3-oxo-2,3-dihydro-1H-pyrazole-4-carboxamide;

N-(4-(5-acetylpyrrolo[1,2-b]pyridazin-4-yloxy)-3-fluorophenyl)-2-(4-fluorophenyl)-1-5-dimethyl-3-oxo-2,3-dihydro-1H-pyrazole-4-carboxamide;

N-(4-(5-acetylpyrrolo[1,2-b]pyridazin-4-yloxy)-3-fluorophenyl)-1,5-dimethyl-3-oxo-2-phenyl-2,3-dihydro-1H-pyrazole-4-carboxamide;

N-(3-fluoro-4-(5-(1-hydroxyethyl)pyrrolo[1,2-b]pyridazin-4-yloxy)phenyl)-1,5-dimethyl-3-oxo-2-phenyl-2,3-dihydro-1H-pyrazole-4-carboxamide;

N-(3-fluoro-4-(5-thiazol-2-yl)pyrrolo[1,2-b]pyridazin-4-yloxy)phenyl)-1,5-dimethyl-3-oxo-2-phenyl-2,3-dihydro-1H-pyrazole-4-carboxamide;

N-(3-fluoro-4-(5-(pyridin-3-yl)pyrrolo[1,2-b]pyridazin-4-yloxy)phenyl)-1,5-dimethyl-3-oxo-2-phenyl-2,3-dihydro-1H-pyrazole-4-carboxamide;

N-(4-(5-ethylpyrrolo[1,2-b]pyridazin-4-yloxy)-3-fluorophenyl)-2-(4-fluorophenyl)-1,5-dimethyl-3-oxo-2,3-dihydro-1H-pyrazole-4-carboxamide;

N-(3-fluoro-4-(pyrrolo[1,2-b]pyridazin-4-yloxy)phenyl)-2-(4-fluorophenyl)-1,5-dimethyl-3-oxo-2,3-dihydro-1H-pyrazole-4-carboxamide;

N-(3-fluoro-4-(5-(pyridin-4-yl)pyrrolo[1,2-b]pyridazin-4-yloxy)phenyl)-1,5-dimethyl-3-oxo-2-phenyl-2,3-dihydro-1H-pyrazole-4-carboxamide;

N-(4-(5-chloropyrrolo[1,2-b]pyridazin-4-yloxy)-3-fluorophenyl)-2-(4-fluorophenyl)-1,5-dimethyl-3-oxo-2,3-dihydro-1H-pyrazole-4-carboxamide;

N-(4-(5-chloropyrrolo[1,2-b]pyridazin-4-yloxy)-3-fluorophenyl)-1,5-dimethyl-3-oxo-2-phenyl-2,3-dihydro-1H-pyrazole-4-carboxamide;

N-(3-fluoro-4-(5-(1-hydroxypropyl)pyrrolo[1,2-b]pyridazin-4-yloxy)phenyl)-1,5-dimethyl-3-oxo-2-phenyl-2,3-dihydro-1H-pyrazole-4-carboxamide;

N-(3-fluoro-4-(2-(thiophen-2-yl)-1H-pyrrolo[2,3-b]pyridin-4-yloxy)phenyl)-2-(4-fluorophenyl)-1,5-dimethyl-3-oxo-2,3-dihydro-1H-pyrazole-4-carboxamide;

N-(3-fluoro-4-(2-(thiophen-3-yl)-1H-pyrrolo[2,3-b]pyridin-4-yloxy)phenyl)-2-(4-fluorophenyl)-1,5-dimethyl-3-oxo-2,3-dihydro-1H-pyrazole-4-carboxamide;

N-(3-fluoro-4-(2-(4-methoxyphenyl)-1H-pyrrolo[2,3-b]pyridin-4-yloxy)phenyl)-2-(4-fluorophenyl)-1,5-dimethyl-3-oxo-2,3-dihydro-1H-pyrazole-4-carboxamide;

N-(3-fluoro-4-(2-(4-methoxyphenyl)-1H-pyrrolo[2,3-b]pyridin-4-yloxy)phenyl)-1,5-dimethyl-3-oxo-2-phenyl-2,3-dihydro-1H-pyrazole-4-carboxamide;

N-(3-fluoro-4-(2-(thiophen-3-yl)-1H-pyrrolo[2,3-b]pyridin-4-yloxy)phenyl-1,5-dimethyl-3-oxo-2-phenyl-2,3-dihydro-1H-pyrazole-4-carboxamide; and N-(3-fluoro-4-(2-(thiophen-2-yl)-1H-pyrrolo[2,3-b]pyridin-4-yloxy)phenyl)-1,5-dimethyl-3-oxo-2-phenyl-2,3-dihydro-1H-pyrazole-4-carboxamide.

The various substituents used to describe the compound of the present invention are defined as follows. The definition applies to the present invention individually or as part of larger groups (unless specified otherwise).

The term "alkyl" used herein alone or as a suffix or prefix as in "alkoxy", "arylalkyl", "haloalkyl" and "alkylamino" includes, unless defined otherwise, a linear or branched radical having 1 to 12 carbon atoms. A more preferred alkyl radical is a "lower alkyl" radical having 1 to 6 carbon atom(s). The alkyl group may be substituted at any possible sites and may be a substituted linear, branched or cyclic saturated hydrocarbon group. An alkyl group substituted with another alkyl group is referred to as "branched alkyl". Typical alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, etc. Typical substituents of the alkyl group include the followings, but are not limited thereto: alkyl, aryl, halo (e.g. F, Cl, Br, I), haloalkyl (e.g. $CCl_3$ or $CF_3$), alkoxy, alkylthio, hydroxy, carboxy (—COOH), alkyloxycarbonyl (—C(O)OR), alkylcarbonyl (—C(O)R), alkylcarbonyloxy (—OCOR), amino (—NH$_2$), carbamoyl (—NHCOOR— or —OCONHR—), urea (—NHCONHR—) and thiol (—SH).

The term "alkenyl" used herein alone or as a suffix or prefix refers to a linear, branched or cyclic hydrocarbon radical having 2 to 12 carbon atoms and one or more carbon-carbon double bond(s). A more preferred alkenyl radical is a "lower alkenyl" radical having 2 to 6 carbon atoms. The most preferred lower alkenyl radical is one having 2 to 4 carbon atoms. The alkenyl group may be substituted at any possible sites. Examples of the alkenyl radical include ethenyl, propenyl, allyl, propenyl, butenyl and 4-methylbutenyl. The terms "alkenyl" and "lower alkenyl" embrace radicals having "cis" and "trans" configurations, or alternatively, "E" and "Z" configurations. Typical substituents of the alkenyl group are the aforesaid alkyl groups. They may be further substituted with, for example, amino, oxo, hydroxyl, etc.

The term "alkynyl" used herein alone or as a suffix or prefix refers to a linear, branched or cyclic hydrocarbon radical having 2 to 12 carbon atoms and one or more carbon-carbon triple bond(s). A more preferred alkynyl radical is a "lower alkynyl" radical having 2 to 6 carbon atoms. The most preferred one is a lower alkynyl radical having 2 to 4 carbon atoms. Examples of the radical include propargyl, butynyl, etc. The alkynyl group may be substituted at any possible sites. Typical substituents of the alkynyl group are the aforesaid alkyl groups as well as amino, alkylamino, etc.

The subscript number following the symbol "C" refers to the number of carbon atoms that the particular group may have. For instance, "$C_1$-$C_6$ alkyl" or "$C_1$-$C_6$ alkyl" refers to a linear or branched saturated carbon chain having 1 to 6 carbon atom (s), for example, methyl, ethyl, n-propyl, isopropyl, n-butyl, sec-butyl, isobutyl, t-butyl, n-pentyl, sec-pentyl, isopentyl and n-hexyl. Depending on the context, "$C_1$-$C_6$ alkyl" may refer only to $C_1$-$C_6$ alkylene with two bridged groups, for example, propane-1,3-diyl, butane-1,4-diyl, 2-methyl-butane-1,4-diyl, etc. "$C_2$-$C_6$ alkenyl" refers to a linear or branched carbon chain having one or more carbon-carbon double bond (s) and 2 to 6 carbon atoms, for example, ethenyl, propenyl, isopropenyl, butenyl, isobutenyl, pentenyl and hexenyl. Depending on the context, "$C_2$-$C_6$ alkenyl" may refer only to $C_2$-$C_6$ alkenediyl with two bridged groups, for example, ethylene-1,2-diyl (vinylene), 2-methyl-2-butene-1, 4-diyl, 2-hexene-1,6-diyl, etc. "$C_2$-$C_6$ alkynyl" refers to a linear or branched carbon chain having one or more carbon-carbon triple bond(s) and 2 to 6 carbon atoms, for example, ethynyl, propynyl, butynyl and hexynyl.

The term "alkoxy" or "alkylthio" used herein alone or as a suffix or prefix respectively refers to an alkyl group linked by oxygen (—O—) or sulfur (—S—).

The term "alkoxycarbonyl" used herein alone or as a suffix or prefix refers to an alkoxy group linked by a carbonyl group. The alkoxycarbonyl radical is represented by —C(O)OR (where R is linear or branched $C_1$-$C_6$ alkyl, cycloalkyl, aryl or heteroaryl).

The term "alkylcarbonyl" used herein alone or as a suffix or prefix refers to an alkyl group linked by a carbonyl, i.e., —C(O)R.

The term "hydroxyalkyl" used herein alone or as a suffix or prefix refers to an alkyl group linked by a hydroxy group, i.e., —COH.

The term "alkylcarbonyloxy" used herein alone or as a suffix or prefix refers to an alkylcarbonyl linked by oxygen.

The term "arylalkyl (or aralkyl)" used herein alone or as a suffix or prefix refers to an aromatic ring linked by an alkyl group, i.e., an aryl-substituted alkyl radical. A preferred arylalkyl radical is a "lower arylalkyl" radical with an aryl radical attached to an alkyl radical having 1 to 6 carbon atom(s). More preferred is "phenylalkylenyl" attached to an alkyl moiety having 1 to 3 carbon atom(s). Examples of the radical include benzyl, biphenylmethyl and phenylethyl. The aryl of the arylalkyl may be further substituted with halo, alkyl, alkoxy, haloalkyl or haloalkoxy.

The term "aryl" used herein alone or as a suffix or prefix refers to a monocyclic or bicyclic aromatic ring, for example, phenyl, substituted phenyl, etc., as well as a fused ring, for example, naphthyl, phenanthrenyl, indenyl, tetrahydronaphthyl, indanyl, etc. Thus, the aryl group may have one or more ring(s) having 6 or more atoms and 5 or less rings having 22 or less atoms. Alternating (conjugated) double bonds may be present between neighboring carbon atoms or adequate heteroatom(s). The aryl group may be substituted with one or more group(s) including, halogen, e.g. F, Br, Cl or I, alkyl, e.g. methyl, ethyl or propyl, alkoxy, e.g. methoxy or ethoxy, hydroxy, carboxy, carbamoyl, alkyloxycarbonyl, nitro, alkenyloxy, trifluoromethyl, amino, cycloalkyl, aryl, heteroaryl, cyano, alkyl S(O)$_m$ (where m=0, 1 or 2) or thiol, but not limited thereto. A preferred aryl group is substituted phenyl.

The term "heterocyclyl" includes a saturated, partially saturated or unsaturated heteroatom-containing ring radical, wherein the heteroatom may be one or more selected from nitrogen, sulfur and oxygen. The "heterocyclyl" group may be a 3- to 10-membered heterocyclyl group. The "heterocyclyl" group may be substituted with 1 to 3 hydroxyl, Boc, halo, haloalkyl, cyano, lower alkyl, lower aralkyl, oxo, lower alkoxy, amino or lower alkylamino substituent(s).

Examples of the saturated heterocyclyl group include: a saturated 3 to 6-membered heterocyclyl group containing 1 to 4 nitrogen atom(s) (e.g. pyrrolidinyl, imidazolinyl, piperidinyl, pyrrolinyl or piperazinyl); a saturated 3- to 6-membered heteromonocyclic group containing 1 or 2 oxygen atom(s) and 1 to 3 nitrogen atom(s) (e.g. morpholinyl); and a saturated 3- to 6-membered heteromonocyclic group containing 1 or 2 sulfur atom(s) and 1 to 3 nitrogen atom(s) (e.g. thiazolidinyl). Examples of the partially saturated heterocyclyl radical include dihydrothienyl, dihydropyranyl, dihydrofuryl and dihydrothiazolyl.

Examples of the unsaturated heterocyclyl group include: an unsaturated 5- or 6-membered heteromonocyclic group containing 1 to 4 nitrogen atom(s), e.g. pyrrolyl, imidazolyl, pyrazolyl, 2-pyridyl, 3-pyridyl, 4-pyridyl, pyrimidyl, pyrazinyl, pyridazinyl or triazolyl (e.g. 4H-1,2,4-triazolyl, 1H-1,2, 3-triazolyl or 2H-1,2,3-triazolyl); an unsaturated 5- or 6-membered heteromonocyclic group containing one oxygen atom, e.g. pyranyl, 2-furyl, 3-furyl, etc.; an unsaturated 5- or 6-membered heteromonocyclic group containing one sulfur atom, e.g. 2-thienyl, 3-thienyl, thiophenyl, etc.; an unsaturated 5- or 6-membered heteromonocyclic group containing 1 or 2 oxygen atom(s) and 1 to 3 nitrogen atom(s), e.g. oxazolyl, isoxazolyl or oxadiazolyl (e.g. 1,2,4-oxadiazolyl, 1,3,4-oxadiazolyl or 1,2,5-oxadiazolyl); and an unsaturated 5- or 6-membered heteromonocyclic group containing 1 or sulfur atom(s) and 1 to 3 nitrogen atom(s), e.g. thiazolyl, thiadiazolyl (e.g. 1,2,4-thiadiazolyl, 1,3,4-thiadiazolyl, 1,2,5-thiadiazolyl).

The term "heterocyclyl" also embraces a heterocyclic radical fused/condensed with an aryl radical. For example, an unsaturated condensed heterocyclic group containing 1 to 5 nitrogen atom(s), e.g. indolyl, isoindolyl, indolizinyl, benzimidazolyl, quinolyl, isoquinolyl, indazolyl, benzotriazolyl, tetrazolopyridazinyl (e.g. tetrazolo[1,5-b]pyridazinyl); an unsaturated condensed heterocyclic group containing 1 or 2 oxygen atom(s) and 1 to 3 nitrogen atom(s), e.g. benzoxazolyl or benzoxadiazolyl; an unsaturated condensed heterocyclic group containing 1 or 2 sulfur atom(s) and 1 to 3 nitrogen atom(s), e.g. benzothiazolyl or benzothiadiazolyl; and a saturated, partially saturated or unsaturated condensed heterocyclic group containing 1 or 2 oxygen atom(s) or sulfur atom(s), e.g. benzofuryl, benzothienyl, 2,3-dihydro-benzo[1,4]dioxynyl or dihydrobenzofuryl, are included. A preferred heterocyclic radical includes a fused or unfused radical consisting of 5 to 10 atoms. More preferred examples of the heteroaryl radical include quinolyl, isoquinolyl, imidazolyl, pyridyl, thienyl, thiazolyl, oxazolyl, furyl and pyrazinyl. Another preferred heteroaryl radical is 5- or 6-membered heteroaryl containing 1 or 2 heteroatom(s) selected from sulfur, nitrogen and oxygen, and may be selected form thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Specific examples of a non-nitrogen-containing heteroaryl include pyranyl, 2-furyl, 3-furyl, 2-thienyl, 3-thienyl, benzofuryl, benzothienyl, etc.

Specific examples of partially saturated or saturated heterocyclyl include pyrrolidinyl, imidazolinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydroquinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-I-'-benzo[d]isothiazol-6-yl, dihydropyranyl, dihydrofuryl, dihydrothiazolyl, etc.

The term "amino" used herein alone or as a suffix or prefix refers to —NH$_2$. The "amino" group may be substituted with 1 or 2 identical or different substituent(s), e.g. alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, carbonyl or carboxyl. These substituents may be further substituted with a carboxylic, alkyl or aryl substituent. In some embodiments, the amino group is substituted with carboxyl or carbonyl to form an N-acyl or N-carbamoyl derivative.

The term "cycloalkyl" used herein alone or as a suffix or prefix refers to a completely saturated or partially saturated hydrocarbon ring having 3 to 9, preferably 3 to 7 carbon atoms. The cycloalkyl group may be substituted. A substituted cycloalkyl ring may have 1, 2 or 3 substituent(s) selected from the group consisting of halo, alkyl, substituted alkyl, alkenyl, alkynyl, nitro, cyano, oxo (=O), hydroxy, alkoxy, thioalkyl, —CO$_2$H, —C(=O)H, CO$_2$-alkyl, —C(=O) alkyl, keto, =N—OH, =N—O-alkyl, aryl, heteroaryl, heterocyclyl, 5- or 6-membered ketal (e.g. 1,3-dioxolane or 1,3-dioxane), —NR'R", —C(=O)NR'R", —CO$_2$NR'R", —NR'CO$_2$R", —NR'C(=O)R", —SO$_2$NR'R" and —NR'SO$_2$R" (where each R' and R" is independently selected from hydrogen, alkyl, substituted alkyl and cycloalkyl, or R' and R" together forms a heterocyclo or heteroaryl ring).

The term "heteroaryl" used herein alone or as a suffix or prefix refers to a substituted or unsubstituted aromatic 5- or 6-membered monocyclic group, 9- or 10-membered bicyclic group or 11- to 14-membered tricyclic group containing one or more heteroatom(s) (O, S or N) in one or more ring(s). Each ring of the heteroaryl group containing the heteroatom(s) may contain 1 or 2 oxygen or sulfur atom(s) and/or 1 to 4 nitrogen atom(s), with the proviso that each ring contains 4 or less heteroatom(s) and has 1 or more carbon atom(s). The fused rings that constitute a bicyclic or tricyclic group may contain carbon atoms only, and may be saturated, partially saturated or unsaturated. The nitrogen or sulfur atom may be oxidized, and the nitrogen atom may be quaternized. The bicyclic or tricyclic heteroaryl group should have one or more complete aromatic ring(s), but other fused rings may be aromatic or non-aromatic. The heteroaryl may be substituted at nitrogen or carbon atom of any possible sites. The heteroaryl ring may have 0, 1, 2 or 3 substituent (s) selected from the group consisting of halo, alkyl, substituted alkyl, alkenyl, alkynyl, aryl, nitro, cyano, hydroxy, alkoxy, thioalkyl, —CO$_2$H, —C(=O)H, —CO$_2$-alkyl, —C(=O)alkyl, phenyl, benzyl, phenylethyl, phenyloxy, phenylthio, cycloalkyl, substituted cycloalkyl, heterocyclyl, heteroaryl, —NR'R", —C(=O)NR'R", —CO$_2$NR'R", —NR'CO$_2$R", —NR'C(=O)R", —SO$_2$NR'R" and —NR'SO$_2$R" (where each R' and R" is independently selected from hydrogen, alkyl, substituted alkyl and cycloalkyl, or R' and R" together forms a heterocyclo or heteroaryl ring).

Typical monocyclic heteroaryl groups include pyrrolyl, pyrazolyl, pyrazolinyl, imidazolyl, oxazolyl, diazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, etc.

Typical bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl, etc.

Typical tricyclic heteroaryl groups include carbazolyl, benzidolyl, phenanthrolinyl, acridinyl, phenanthridinyl, xanthenyl, etc.

The term "heterocycloalkyl" used herein alone or as a suffix or prefix refers to cycloalkyl (non-aromatic) one carbon atom of which is replaced by a heteroatom selected from O, S and N and 3 or less additional carbon atom(s) of which may be replaced by the heteroatom(s). The term "heterocycloalkyl" used herein alone or as a suffix or prefix refers to a stable, 5- to 7-membered saturated or partially saturated monocyclic ring containing carbon atoms and heteroatom(s) selected from nitrogen, sulfur and oxygen. The heterocyclic ring may be a 5-, 6- or 7-membered monocyclic ring and may contain 1, 2 or 3 heteroatom (s) selected from nitrogen, sulfur and oxygen. The heterocyclic ring may be substituted at one or more possible site(s) with one or more substituent(s) selected from alkyl (preferably lower alkyl), heterocycloalkyl, heteroaryl, alkoxy (preferably lower alkoxy), nitro, monoalkylamino (preferably lower alkylamino), dialkylamino (preferably di[lower]alkylamino), cyano, halo, haloalkyl (preferably trifluoromethyl), alkanoyl, aminocarbonyl, monoalkylaminocarbonyl, dialkylaminocarbonyl, alkylamido (preferably lower alkylamido), alkoxyalkyl (preferably lower alkoxy [lower]alkyl), alkoxycarbonyl (preferably lower alkoxycarbonyl), alkylcarbonyloxy (preferably lower alkylcarbonyloxy) and aryl (preferably phenyl) (the aryl may be substituted with halo, lower alkyl or lower alkoxy). Examples of the heterocycloalkyl group include piperazinyl, piperidinyl, morpholinyl, homomorpholinyl, thiomorpholinyl, pyrrolidinyl and azetidinyl.

Also, the heteroaryl or heterocycloalkyl group may be a 8- to 11-membered bicyclic ring containing carbon atoms and 1, 2 or 3 heteroatom(s) selected from nitrogen, sulfur and oxygen. Some preferred bicyclic rings include benzodioxolyl, quinoxalinyl, indolyl and quinolinyl. The phrase that heteroaryl or heterocycloalkyl "may be substituted" means that the heteroaryl or heterocycloalkyl group may be substituted at one or more possible site(s) with one or more substituent(s) selected from alkyl (preferably lower alkyl), alkoxy (preferably lower alkoxy), nitro, monoalkylamino (preferably lower alkylamino), dialkylamino (preferably di[lower]alkylamino), cyano, halo, haloalkyl (preferably trifluoromethyl), alkanoyl, aminocarbonyl, monoalkylaminocarbonyl, dialkylaminocarbonyl, alkylamido (preferably lower alkylamido), alkoxyalkyl (preferably lower alkoxy[lower]alkyl), alkoxycarbonyl (preferably lower alkoxycarbonyl), alkylcarbonyloxy (preferably lower alkylcarbonyloxy) and aryl (preferably phenyl) (the aryl may be substituted with halo, lower alkyl or lower alkoxy).

The term "heteroatom" refers to O, S or N. It is to be noted that a heteroatom having unsatisfied valence has hydrogen atom(s) to satisfy the valence requirement.

The term "halogen" or "halo" refers to chlorine, bromine, fluorine or iodine.

The term "sulfonyl" used herein alone or with other terms such as alkylsulfonyl refer to the divalent radical —$SO_2$—.

The terms "sulfamyl", "aminosulfonyl" and "sulfonamidyl" refer to a sulfonyl radical substituted with an amine radical, forming sulfonamide (—$SO_2NH_2$).

The term "alkylaminosulfonyl" embraces "N-alkylaminosulfonyl" with a sulfamyl radical substituted with 1 or 2 alkyl radical(s). A more preferred alkylaminosulfonyl radical is a "lower alkylaminosulfonyl" radical having 1 to 6 carbon atom(s). Further more preferred is a lower alkylaminosulfonyl radical having 1 to 3 carbon atom(s). Examples of the lower alkylaminosulfonyl radical include N-methylaminosulfonyl and N-ethylaminosulfonyl.

The term "carboxy" or "carboxyl" used herein alone or with other terms such as "carboxyalkyl" refers to —$CO_2H$.

The term "carbonyl" used herein alone or with other terms such as "aminocarbonyl" refers to —(C=O)—.

The term "aminocarbonyl" refers to an amide group represented by —C(=O)$NH_2$—.

The terms "N-alkylaminocarbonyl" and "N,N-dialkylaminocarbonyl" respectively refer to an aminocarbonyl radical substituted with 1 or 2 alkyl radical(s). More preferred is "lower alkylaminocarbonyl" with a lower alkyl radical attached to the aminocarbonyl radical.

The terms "N-arylaminocarbonyl" and "N-alkyl-N-arylaminocarbonyl" respectively refer to an aminocarbonyl radical substituted with one aryl radical or with one alkyl and one aryl radicals.

The terms "heterocyclylalkylenyl" and "heterocyclylalkyl" embrace a heterocyclic-substituted alkyl radical. A more preferred heterocyclylalkyl radical is a "5- or 6-membered heteroarylalkyl" radical having a $C_1$-$C_6$ alkyl moiety and a 5- or 6-membered heteroaryl radical. Further more preferred is a lower heteroarylalkylenyl radical having a $C_1$-$C_3$ alkyl moiety. Examples include pyridinylmethyl and thienylmethyl.

The term "alkylthio" embraces a radical having a $C_1$-$C_{10}$ linear or branched alkyl radical attached to a divalent sulfur atom. More preferred is a lower alkylthio radical having 1 to 3 carbon atom(s). Examples of "alkylthio" include methylthio ($CH_3S$—).

The term "haloalkylthio" embraces a radical having a $C_1$-$C_{10}$ haloalkyl radical attached to a divalent sulfur atom. More preferred is a lower haloalkylthio radical having 1 to 3 carbon atom (s). Examples of "haloalkylthio" include trifluoromethylthio.

The term "alkylamino" embraces "N-alkylamino" and "N,N-dialkylamino", wherein the amino group may be substituted with one or two alkyl radical(s).

A more preferred alkylamino radical is a "lower alkylamino" radical with one or two $C_1$-$C_6$ alkyl radical (s) attached to the nitrogen atom. Further more preferred is a lower alkylamino radical having 1 to 3 carbon atom(s). A suitable alkylamino radical may be mono- or dialkylamino such as N-methylamino, N-ethylamino, N,N-dimethylamino, N,N-diethylamino, etc.

The term "arylamino" refers to an amino group substituted with one or two aryl radical(s) such as N-phenylamino. The aryl ring moiety of the arylamino radical may be further substituted.

The term "heteroarylamino" refers to an amino group substituted with one or two heteroaryl radical(s) such as N-thienylamino. The heteroaryl ring moiety of the "heteroarylamino" radical may be further substituted.

The term "aralkylamino" refers to an amino group substituted with one or two aralkyl radical(s). More preferred is a phenyl-$C_1$-$C_3$ alkylamino radical such as N-benzylamino. The aryl ring moiety of the aralkylamino radical may be further substituted.

The terms "N-alkyl-N-arylamino" and "N-aralkyl-N-alkylamino" respectively refer to an amino group substituted with one aralkyl and one alkyl radicals, or with one aryl and one alkyl radicals.

The term "aminoalkyl" embraces a linear or branched alkyl radical having 1 to 10 carbon atom(s) one of which may be substituted with one or more amino radical(s). A more preferred aminoalkyl radical is a "lower aminoalkyl" radical having 1 to 6 carbon atom(s) and one or more amino radical(s). Examples of the radical include aminomethyl, aminoethyl, aminopropyl, aminobutyl and aminohexyl. More preferred is a lower aminoalkyl radical having 1 to 3 carbon atom(s).

The term "alkylaminoalkyl" embraces an alkyl radical substituted with an alkylamino radical. A more preferred alkylaminoalkyl radical is a "lower alkylaminoalkyl" radical having 1 to 6 carbon atom(s). Further more preferred is a lower alkyl aminoalkyl radical having a $C_1$-$C_3$ alkyl radical. A suitable alkylaminoalkyl radical may be mono- or dialkyl-substituted such as N-methylaminomethyl, N,N-dimethyl-aminoethyl, N,N-diethylaminomethyl, and the like.

The term "alkylaminoalkoxy" embraces an alkoxy radical substituted with an alkylamino radical. A more preferred alkylaminoalkoxy radical is a "lower alkylaminoalkoxy" radical having $C_1$-$C_6$ alkoxy radical. Further more preferred is a lower alkylaminoalkoxy radical having a $C_1$-$C_3$ alkyl radical. A suitable alkylaminoalkoxy radical may be mono- or dialkyl-substituted such as N-methylaminoethoxy, N,N-dimethylaminoethoxy, N,N-diethylaminoethoxy, and the like.

The term "alkylaminoalkoxyalkoxy" embraces an alkoxy radical substituted with an alkylaminoalkoxy radical. A more preferred alkylaminoalkoxyalkoxy radical is a "lower alkylaminoalkoxyalkoxy" radical having a $C_1$-$C_6$ alkoxy radical. Further more preferred is a lower alkylaminoalkoxyalkoxy radical having a $C_1$-$C_3$ alkyl radical. A suitable alkylaminoalkoxyalkoxy radical may be mono- or dialkyl-substituted such as N-methylaminomethoxyethoxy, N-methylaminoethoxyethoxy, N,N-dimethylaminoethoxyethoxy, N,N-diethylaminomethoxymethoxy, and the like.

The term "carboxyalkyl" embraces a linear or branched alkyl radical having 1 to 10 carbon atom(s) one of which may be substituted with one or more carboxy radical(s). A more preferred carboxyalkyl radical is a "lower carboxyalkyl" radical having 1 to 6 carbon atom(s) and a carboxy radical. Examples of the radical include carboxylmethyl, carboxypropyl, and the like.

Further more preferred is a lower carboxyalkyl radical having 1 to 3 $CH_2$ group(s).

The term "halosulfonyl" embraces a sulfonyl radical substituted with a halogen radical. Examples of the halosulfonyl radical include chlorosulfonyl and fluorosulfonyl.

The term "arylthio" embraces a $C_6$-$C_{10}$ aryl radical attached to a divalent sulfur atom. Examples of "arylthio" include phenylthio.

The term "aralkylthio" embraces an aralkyl radical attached to a divalent sulfur atom. More preferred is a phenyl-$C_1$-$C_3$ alkylthio radical. Examples of "aralkylthio" include benzylthio.

The term "aryloxy" embraces an aryl radical, which may be substituted, attached to an oxygen atom. Examples of the radical include phenoxy.

The term "aralkoxy" embraces an oxy-containing aralkyl radical attached to another radical via an oxygen atom.

A more preferred aralkoxy radical is a "lower aralkoxy" radical having a lower alkoxy radical with a phenyl radical, which may be substituted, attached thereto.

The term "heteroaryloxy" embraces a heteroaryl radical, which may be substituted, attached to an oxygen atom.

The term "heteroarylalkoxy" embraces an oxy-containing heteroarylalkyl radical attached to another radical via an oxygen atom. A more preferred heteroarylalkoxy radical is a "lower heteroarylalkoxy" radical having a lower alkoxy radical with a heteroaryl radical, which may be substituted, attached thereto.

The term "cycloalkylalkyl" embraces a cycloalkyl-substituted alkyl radical. A preferred cycloalkylalkyl radical is a "lower cycloalkylalkyl" radical with a cycloalkyl radical attached to a $C_1$-$C_6$ alkyl radical. Further more preferred is "5- or 6-membered cycloalkylalkyl" attached to a $C_1$-$C_3$ alkyl moiety. Examples of the radical include cyclohexylmethyl. The cycloalkyl of the radical may be further substituted with halo, alkyl, alkoxy or hydroxy.

The term "cycloalkenyl" embraces a carbocyclic group having one or more carbon-carbon double bond(s), including "cycloalkyldienyl". A preferred cycloalkenyl group has a $C_3$-$C_6$ ring. More preferred are cyclopentenyl, cyclopentadienyl, cyclohexenyl and cycloheptadienyl.

The term "include", "embrace" or "comprise" is to be understood to include the listed elements but not exclude others.

The term "Chemical Formula 1" is to be understood to include any subformulae.

Medical Use

The compound of the present invention is effective in preventing or treating angiogenesis-related diseases although not limited thereto. The compound of the present invention has inhibitory activity against kinases such as VEGFR/KDR and/or c-Met. The compound of the present invention is useful in treating tumors or minimizing harmful effects of VEGF and/or HGF.

The present invention provides pharmaceutical compositions comprising therapeutically effective amounts of one or more compound(s) represented by Chemical Formula 1 and a pharmaceutically acceptable carrier.

The pharmaceutical composition of the present invention is useful in treating HGF-mediated diseases.

The pharmaceutical composition of the present invention is also useful in treating cancer, asthma, allergy, atopic skin disease, psoriasis or rheumatoid arthritis. Thus, the present invention provides a pharmaceutical composition useful in treating non-small cell lung cancer, colorectal cancer, glioblastoma, head and neck cancer, stomach cancer, bladder cancer, liver cancer, ovarian cancer, and etc.

The pharmaceutical composition of the present invention may further comprise one or more selected from the group consisting of antibiotics, alkylating agents, antimetabolites, hormone drugs, immunological agents, interferon agents and other anti-cancer drugs.

The present invention also provides methods for treating an HGF-mediated disease in a subject in need thereof, comprising administering therapeutically effective amounts of the compound represented by Chemical Formula 1 to the subject.

The present invention also provides methods for treating cancer in a subject in need thereof, comprising administering a therapeutically effective amount of the compound represented by Chemical Formula 1 to the subject.

In the above treating methods, one or more selected from the group consisting of antibiotic, alkylating agent, antimetabolite, hormone drug, immunological agent, interferon agent and other anti-cancer drug may be further administered to the subject.

However, the medical use and treating methods using the compound of the present invention represented by Chemical Formula 1 are not limited to those afore-described. In addition, the drugs that may be used in combination therewith are not limited to those afore-described.

Hereinafter, the medical use and treating method using the compound of the present invention represented by Chemical Formula 1 will be described in detail.

The compound of the present invention is useful in treating tumors, including the following cancers and metastatic tumors, without being limited thereto: cancers, e.g. bladder cancer, breast cancer, colon cancer, renal cancer, liver cancer, lung cancer (including small cell lung cancer), esophageal cancer, gallbladder cancer, ovarian cancer, pancreatic cancer, stomach cancer, cervical cancer, thyroid cancer, prostate cancer and skin cancer (including squamous cell carcinoma); lymphatic hematopoietic tumors (including leukemia, acute lymphoblastic leukemia, acute lymphoblastic leukemia, B-cell lymphoma, T-cell lymphoma, Hodgkin's lymphoma, non-Hodgkin lymphoma, hairy cell lymphoma and Burkitt's lymphoma); myelogenous hematopoietic tumors (including acute and chronic myelogenous leukemia, myelodysplastic syndrome and promyelocytic leukemia); mesenchymally-derived tumors (fibrosarcoma, rhabdomyosarcoma and other sarcoma of, e.g., soft tissue and bone); tumors of the central and peripheral nervous systems (including astrocytoma, neuroblastoma, glioma and neurilemmoma); and other tumors (including melanoma, seminoma, teratocarcinoma, osteosarcoma, xeroderma pigmentosum, keratoacanthoma, follicular thyroid carcinoma and Kaposi's sarcoma).

Preferably, the compound of the present invention is useful in treating tumors selected from lung cancer, colon cancer and breast cancer.

The compound of the present invention may also be useful in treating ophthalmological symptoms, e.g. corneal graft rejection, ocular neovascularization, retinal neovascularization including neovascularization following damage or infection, diabetic retinopathy, retrolental fibroplasia and neovascular glaucoma, retinal ischemia and vitreous hemorrhage; ulcer diseases, e.g. gastric ulcer; pathological but nonmalignant symptoms, e.g. angioma including infantile hemangioma, nasopharyngeal angiofibroma and avascular bone necrosis; and women's reproductive disorders, e.g. endometriosis.

The compound of the present invention is also useful in treating edema and vascular hyperpermeability.

The compound of the present invention is useful in treating proliferative diseases. The compound may be used to treat inflammatory or rheumatoid diseases, particularly clinical symptoms of locomotive organs, e.g. various rheumatoid inflammatory diseases, especially rheumatoid arthritis, juvenile arthritis or chronic multiple arthritis including psoriatic arthropathy; psoriatic arthropathy, tumor-induced inflammatory disease, opacity, extravasation or collagenosis, e.g. systemic lupus erythematosus, multiple myositis, dermatomyositis, systemic sclerodema or mixed collagenosis; post-infection arthritis (In this case, living pathogenic organisms cannot be found in the infected site.) or seronegative spondyloarthritis, e.g. ankylosing spondylitis; vasculitis, sarcoidosis or arthropathy; or complications thereof. Examples of inflammatory diseases include synovial inflammation, e.g. synovitis of particular undetermined/non-induced type, especially bursal synovitis and purulent synovitis. The synovial inflammation may be caused by or related with diseases, for example, osteoarthritis, rheumatoid arthritis or arthritis deformans. The present invention is further applicable to treatment of inflammation, e.g. inflammatory disease or condition at the musculotendinous junction or tendon sheath or systemic inflammation of joints or locomotive organs. The inflammation may be caused by or related with, for example, diseases or conditions including myofascial syndrome and tendomyositis or surgical treatments. The present invention is further applicable to treatment of inflammatory diseases or conditions of connective tissues, e.g. dermatomyositis and myositis.

The compound of the present invention may be used as an active ingredient for disease conditions such as arthritis, atherosclerosis, psoriasis, angioma, myocardial angiogenesis, coronary and cerebral angiogenesis, ischemic leg vascularization, wound healing, peptic ulcer, Helicobacter-related disease, bone fracture, cat scratch fever, rubeosis, neovascular glaucoma, retinopathy, e.g. diabetic retinopathy, and macular degeneration-related diseases. Further, some of the compounds may be used as an active ingredient for solid tumors, malignant ascites, hematopoietic cancers and hyperproliferative diseases, e.g. hyperthyroidism (especially Grave's disease) and cystoma [e.g. hypervascularity of the ovarian stroma characteristic of polycystic ovarian syndrome (Stein-Leventhal syndrome)], since these diseases require proliferation of blood vessel cells for growth and/or metastasis.

Also, some of these compounds may be used as an active ingredient for burns, chronic pulmonary diseases, seizure, polyps, hypersensitivity, chronic and allergic inflammations, ovarian hyperstimulation syndrome, brain tumor-related cerebral edema, high-grade trauma- or hypoxia-induced cerebral or pulmonary edema, intraocular and mascular edema, ascitic and vascular hyperpermeability, extravasation, exudation, protein extravasation or other diseases accompanying edema. These compounds are useful in treating the diseases that induce deposition of fibrin in the extracellular matrix by protein extravasation and accelerate matrix expansion (e.g. fibrosis, cirrhosis and carpal tunnel syndrome).

The compound of the present invention is also useful in treating ulcers including bacterial ulcer, fungal ulcer, Mooren's ulcer and ulcerative colitis.

The compound of the present invention is also useful in treating unwanted angiogenesis, edema or matrix deposition in viral or protozoan infections, e.g. herpes simplex, shingles, AIDS, Kaposi's sarcoma and toxoplasmosis, following trauma, radiation, seizure, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic obstructive pulmonary disease, asthma, inflammatory rheumatoid or rheumatoid diseases.

These compounds are also useful in reducing subcutaneous fat or treating obesity.

The compound of the present invention is also useful in treating ophthalmological conditions other than retinopathy and macular degeneration, such as intraocular and macular edema, ocular neovascularization disease, sclerotitis, uveitis, vitritis, myopia, optical pits, chronic retinal detachment, complications following radial keratotomy or laser surgery, glaucoma, conjunctivitis, Stargardt disease and Eales disease.

The compound of the present invention is also useful in treating cardiovascular conditions, e.g. atherosclerosis, restenosis, arteriosclerosis, occlusion and carotid artery occlusive disease.

The compound of the present invention is also useful in treating cancer-related symptoms, e.g. solid tumor, sarcoma (especially Ewing's sarcoma and osteosarcoma), retinoblastoma, rhabdomyosarcoma, neuroblastoma, hematopoietic tumors including leukemia, lymphoma, tumor-induced pleural or pericardial extravasation, and malignant ascites.

The compound of the present invention is also useful in treating diabetic symptoms, e.g. diabetic retinopathy and microangiopathy. The compound of the present invention is also useful in reducing blood flow to tumors in a patient. The compound of the present invention is also useful in reducing metastasis of tumors in a patient. The compound of the present invention may act as an inhibitor against other protein kinases, e.g. tie-2, lck, src, fgf, c-Met, ron, ckit and ret, and thus may be useful in treating other protein kinase-related diseases.

In addition to treatment of human, the compound of the present invention is also useful for veterinary treatment of mammals, companion animals including rodents, exotic animals and farm animals. More preferred animals include horse, dog and cat.

As used herein, the compound of the present invention includes pharmaceutically acceptable derivatives thereof. In the specification, the plural form of the compound, salt, or the like, is understood to include a sing compound, salt, or the like.

The compound of the present invention may be administered alone as an active ingredient. However, one or more of the compound of the present invention may also be used optionally in combination with other agent. When used in combination, the treatment drug may be formulated into individual compositions to be administered at once or at different times, or into a single composition.

The term "cotherapy" or "combination-therapy", in defining the use of the compound of the present invention or other pharmaceutical agents, embraces the administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of the compound of the present invention may be accompanied by an additional therapy known to those skilled in the art with regard to the prevention or treatment of tumors, such as radiotherapy or administration of an inhibitor of cell proliferation or a cytotoxic agent.

When formulated for a fixed administration dose, the combination drug may comprise the compound of the present invention within an allowed administration range. If combination with other agent is inadequate, the compound represented by Chemical Formula 1 may be administered sequentially with a known anti-cancer drug or cytotoxic agent. The order of administration is not particularly limited. That is to say, the compound of the present invention may be administered before, after or simultaneously with the known anticancer drug or cytotoxic agent.

At present, the standard treatment of primary tumors consists of surgical operation followed by radiation or chemotherapy via IV injection. Commonly, a chemotherapic regimen comprises a DNA alkylating agent, a DNA insertion agent, a CDK inhibitor or a microtubular toxin. The chemotherapic administration dose is below the maximum allowable dose. In general, the dose-limiting toxicities include nausea, vomiting, diarrhea, depilation, neutropenia, or the like.

A lot of antitumor agents selected for the treatment of tumors via combination drug chemotherapy for commercial purpose, clinical evaluation and pre-clinical development may be used. The antitumor agent may be classified into several major categories, i.e., antibiotic agents, alkylating agents, antimetabolic agents, hormone agents, immunological agents, interferon agents, or the like.

A first class of antitumor agents that may be used in combination with the compound of the present invention consists of antimetabolic/thymidylate synthase-inhibiting antitumor agents. Suitable antimetabolic antitumor agents may be selected from the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin, but are not limited thereto.

A second class of antitumor agents which may be used in combination with the compound of the present invention consists of alkylating-type antitumor agents.

Suitable alkylating-type antitumor agents may be selected from the group consisting of Shionogi 254-S, i-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenyl spiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin and trimelamol, but are not limited thereto.

A third class of antitumor agents that may be used in combination with the compound of the present invention consists of antibiotic-type antitumor agents. Suitable antibiotic-type antitumor agents may be selected from known antibiotic-type antitumor agents.

A fourth class of antitumor agents that may be used in combination with the compound of the present invention consists of tubulin-interacting agents, topoisomerase II inhibitor, topoisomerase I inhibitor, hormone agents and other antitumor agents, but are not limited thereto.

Alternatively, the compound of the present invention may be used in combination with the following other antitumor agents: acemannann, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizximab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicinalfa, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, imiquimod, interferon alfa, interferon alfa, natural, interferon alfa-2, interferon alfa-2a, interferon alfa-2b, interferon alfa-N1, interferon alfa-n3, interferon alfacon-1, interferon alfa, natural, interferon beta, interferon beta-1a, interferon beta-1b, interferon gamma, natural, interferon gamma-1a, interferon gamma-1b, interleukin-1 beta, iobenguane, irinotecan, irsogladine, lanreotide, LC 9018 (Yakult), lefiunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium ($^{186}$Re) etidronate, RII retinamide, rituximab, romurtide, samarium ($^{153}$Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, virulizin, zinostatin stimalamer, zoledronic acid, abarelix, AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, p30 protein, pegvisomant, pemetrexed, porfiromycin, prinomastat, RL 0903 (Shire), rubitecan, satraplatin, sodium phenylacetate, sparfosic acid, SRL 172 (SRPharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysate vaccine (Royal Newcastle Hospital) oor valspodar.

Alternatively, the compound of the present invention may also be used in combination therapies with known VEGFR inhibitors. Other compounds described in various patents and patent applications can be used in combination therapies.

In some embodiments, the combination comprises the composition of the present invention with one or more anti-angiogenic agent(s). These agents are inclusive of, but not limited to, chemical compositions synthesized in vitro, antibodies, antigen binding regions, radionuclides and combinations and conjugates thereof. The agent can be agonist, antagonist, allosteric modulator, toxin or, more generally, may act to inhibit or stimulate its target (e.g. receptor or enzyme), and thereby promote cell death or arrest cell growth.

Exemplary antitumor agents include HERCEPTIN™ (trastuzumab), which may be used to treat breast cancer and other forms of cancer, and RITUXAN™ (rituximab), ZEVALIN™ (ibritumomab tiuxetan) and LYMPHOCIDE™ (epratuzumab), which may be used to treat non-Hodgkin lymphoma and other forms of cancer, GLEEVAC™ which may be used to treat chronic myelogenous leukemia and gastrointestinal stromal tumors, and BEXXAR™ (iodine 131 tositumomab) which may be used to treat non-Hodgkin lymphoma.

Exemplary anti-angiogenic agents include ERBITUX™ (IMC-C225), KDR (kinase domain receptor) inhibitors (e.g. antibodies and antigen binding regions that specifically bind to the kinase domain receptor), anti-VEGF agents (e.g. antibodies and antigen binding regions that specifically bind to VEGF, soluble VEGF receptors or a ligand binding region thereof) such as AVASTIN™ or VEGF-TRAP™, anti-VEGF receptor agents (e.g. antibodies and antigen binding regions that specifically bind thereto), EGFR inhibitors (e.g. antibodies and antigen binding regions that specifically bind thereto) such as ABX-EGF (panitumumab), IRESSA™ (gefitinib) and TARCEVA™ (erlotinib), anti-Ang1 and anti-Ang2 agents (e.g. antibodies and antigen binding regions that specifically bind thereto or to their receptors, e.g. Tie2/Tek) and anti-Tie2 kinase inhibitors (e.g. antibodies and antigen binding regions that specifically bind thereto). The pharmaceutical composition of the present invention can also include one or more agent (s) (e.g. antibodies, antigen binding regions or soluble receptors) that specifically bind to and inhibit the activity of growth factors, such as antagonists of hepatocyte growth factor (HGF, also known as scatter factor), and antibodies and antigen binding regions that specifically bind to its receptor "c-Met".

Other anti-angiogenic agents include Campath, IL-8, B-FGF, Tek antagonists, anti-TWEAK agents (e.g. antibodies and antigen binding regions that specifically bind thereto or soluble TWEAK receptor antagonists), ADAM disintegrin domain that antagonizes the binding of integrin to its ligand, anti-eph receptor and/or anti-ephrin antibodies or antigen binding regions that specifically bind thereto, and anti-PDGF-BB antagonists (e.g. antibodies and antigen binding regions that specifically bind thereto), as well as antibodies and antigen binding regions that specifically bind to PDGF-BB ligands, and PDGFR kinase inhibitors (e.g. antibodies and antigen binding regions that specifically bind thereto).

Alternatively, the compound of the present invention may also be used in combination therapies with other antitumor agents, such as VEGF antagonists, other kinase inhibitors including p38 inhibitors KDR inhibitors, EGF inhibitors and CDK inhibitors, TNF inhibitors, matrix metalloprotease inhibitors (MMP), COX-2 inhibitors including celecoxib, NSAID's or $\alpha_v\beta_3$ inhibitors.

A pharmaceutical composition containing the compound of the present invention may be in a form adequate for oral administration, for example, tablet, buccal tablet, lozenge, aqueous or oily suspension, dispensable powder, granule, emulsion, hard or soft capsule, syrup or elixir. The composition intended for oral administration may be prepared according to any method known in the art. Such compositions may typically contain one or more agent(s) selected from the group consisting of sweetener, flavoring agent, coloring agent and preservative in order to provide pharmaceutically elegant and palatable preparations. The tablet may contain an adequate, nontoxic, pharmaceutically acceptable excipient as well as the active ingredient. The excipient may be, for example, inert diluents such as calcium carbonate, sodium carbonate, lactose, calcium phosphate or sodium phosphate, granulating and disintegrating agents such as microcrystalline cellulose, sodium crosscarmellose, corn starch or alginic acid, binders such as starch, gelatin, polyvinylpyrrolidone or gum acacia, and lubricants such as magnesium stearate, stearic acid or talc. The tablet may be un-coated or coated by known techniques to mask the taste of the drug or delay disintegration and absorption in the gastrointestinal tract and thereby provide a sustained action over a longer period. For example, a water-soluble taste masking material such as hydroxypropyl methylcellulose or hydroxypropylcellulose, or a time delay material such as ethyl cellulose or cellulose acetate butyrate may be employed. Formulations for oral use may be presented as hard gelatin capsules wherein the active ingredient is mixed with an inert solid diluent, for example, calcium carbonate, calcium phosphate or kaolin, or as soft gelatin capsules wherein the active ingredient is mixed with a water-soluble carrier such as polyethylene glycol or an oil medium, for example, peanut oil, liquid paraffin or olive oil.

An aqueous suspension contains the active ingredient in admixture with an excipient suitable for the preparation of aqueous suspensions. The excipient may be suspending agents, for example, sodium carboxymethylcellulose, methylcellulose, hydroxypropyl methylcellulose, sodium alginate, polyvinylpyrrolidone, gum tragacanth and gum acacia, dispersing or wetting agents such as a naturally-occurring phosphatide, e.g. lecithin, condensation products of alkylene oxide with fatty acid, e.g. polyoxyethylene stearate, condensation products of ethylene oxide with long chain aliphatic alcohol, e.g. heptadecaethyleneoxycetanol, condensation products of ethylene oxide with partial ester derived from fatty acid and hexitol, e.g. polyoxyethylen esorbitol monooleate, or condensation products of ethylene oxide with partial ester derived from fatty acid and hexitol anhydride, e.g. polyethylene sorbitan monooleate. The aqueous suspension may also contain one or more preservative(s), e.g. ethyl or n-propyl p-hydroxybenzoate, one or more coloring agent(s), one or more flavoring agent (s) and one or more sweetener (s), e.g. sucrose, saccharin or aspartame.

An oily suspension may be formulated by suspending the active ingredient in a vegetable oil, for example, arachis oil, olive oil, sesame oil or coconut oil, or in a mineral oil such as liquid paraffin. The oily suspension may contain a thickening agent, for example, beeswax, hard paraffin or cetyl alcohol. A sweetener such as those set forth above and a flavoring agent may be added to provide a palatable oral preparation. These compositions may be preserved by adding an antioxidant such as butylated hydroxyanisole or alpha-tocopherol.

Dispensable powder and granule suitable for preparation of an aqueous suspension by adding water provide the aqueous suspension comprising the active ingredient in admixture with a dispersing agent, a wetting agent, a suspending agent and one or more preservative(s). A suitable dispersing agent, wetting agent or suspending agent are exemplified by those already mentioned above. Additional excipients, for example, sweetener, flavoring agent and coloring agent may also be present. These compositions may be preserved by adding an antioxidant such as ascorbic acid. The pharmaceutical composition of the present invention may also be in the form of an oil-in-water emulsion. The oily phase may be a vegetable oil, for example, olive oil or arachis oil, or a mineral oil, for example, liquid paraffin, or a mixture thereof. A suitable emulsifier may be naturally-occurring phosphatides, e.g. soybean lecithin, and esters or partial esters derived from fatty acid and hexitol anhydride, e.g. sorbitan monooleate, and condensation products of the aforesaid partial ester with ethylene oxide, e.g. polyoxyethylene sorbitan monooleate.

The emulsion may also contain a sweetener, a flavoring agent, a preservative or an antioxidant.

The syrup and elixir may be formulated using a sweetener, for example, glycerol, propylene glycol, sorbitol or sucrose. Such formulations may also contain a demulcent, a preservative, a flavoring agent, a coloring agent or an antioxidant. The pharmaceutical composition may also be a sterile injectable aqueous solution. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in an oily phase. For example, the active ingredient may be first dissolved in a mixture of soybean oil and lecithin. The oil solution is then introduced into a mixture of water and glycerol and processed to form a microemulsion. The injectable solution or microemulsion may be introduced into a patient's bloodstream by local bolus injection.

Alternatively, it may be advantageous to administer the solution or microemulsion in such a way as to maintain a constant circulating concentration of the compound of the present invention. In order to maintain such a constant concentration, a continuous intravenous delivery device may be utilized. An example of such a device is the Deltec CADD-PLUS™ model 5400 intravenous pump.

The pharmaceutical composition of the present invention may be in the form of a sterile injectable aqueous or oleaginous suspension for intramuscular or subcutaneous administration. This suspension may be formulated according to the known art using those suitable dispersing agents, wetting agents or suspending agents which have been mentioned above. The sterile injectable preparation may also be a sterile injectable solution or suspension in a non-toxic parenterally-acceptable diluent or solvent, for example, as a solution in 1,3-butanediol. In addition, a sterile fixed oil may be commonly employed as a solvent or suspending medium. For this purpose, any bland fixed oil may be employed including synthetic mono- or diglyceride. In addition, fatty acids such as oleic acid find use in the preparation of injectables.

The compound of the present invention represented by Chemical Formula 1 may also be administered in the form of a suppository for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions, suspensions, and the like containing the compound represented by Chemical Formula 1 can be used (As used herein, topical application can include mouth washes and gargles).

The compound of the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the administration dosage will, of course, be continuous rather than intermittent throughout the dosage regimen. The compound of the present invention may be administered in the form of a suppository using, for example, cocoa butter, glycerinated gelatin, hydrogenated vegetable oils, mixtures of polyethylene glycols of various molecular weights or fatty acid esters of polyethylene glycol.

When the compound according to the present invention is administered into a human subject, the daily dosage will normally be determined by the prescribing physician with the dosage generally varying according to the age, weight, sex and response of the individual patient, as well as the severity of the patient's symptoms. Such combination products if formulated as a fixed dose employ the compound of the present invention within the dose range described above as well as other pharmaceutically active agent within its approved dose range. In case the combination preparation of the compound represented by Chemical Formula 1 is inappropriate, it may be administered sequentially with a known anti-cancer drug or cytotoxic agent. The sequence of the administration is not limited in the present invention. That is to say, the compound represented by Chemical Formula 1 may be administered before or after the administration of the known anti-cancer drug or cytotoxic agent.

The terms used in this specification are defined as follows.

The term "angiogenesis" refers to the change in existing blood vessels favoring tissue perfusion or the formation of new vasculature. It embraces sprouting of new blood vessels from existing ones by producing endothelial cells, as well as modification of existing blood vessels for improving tissue perfusion through change in size, development, direction or fluidity.

As used herein, the term "HGF" refers to hepatocyte growth factor/scatter factor. It embraces purified hepatocyte growth factor/scatter factor, fragments of hepatocyte growth factor/scatter factor, fragments of chemically synthesized hepatocyte growth factor/scatter factor, derivatives or mutation variants of hepatocyte growth factor/scatter factor, and fused protein comprising hepatocyte growth factor/scatter factor and other protein. The term "HGF" as used herein also embraces hepatocyte growth factor/scatter factor isolated from species other than human.

As used herein, the term "c-Met" refers to an HGF receptor. It embraces a purified receptor, fragments of the receptor, fragments of a chemically synthesized receptor, derivatives or mutation variants of the receptor, and fused protein comprising the receptor and other protein. The term "c-Met" also embraces an HGF receptor isolated from species other than human.

As used herein, the term "HGF" refers to hepatocyte growth factor/scatter factor. It embraces purified hepatocyte growth factor/scatter factor, fragments of hepatocyte growth factor/scatter factor, fragments of chemically synthesized hepatocyte growth factor/scatter factor, derivatives or mutation variants of hepatocyte growth factor/scatter factor, and fused protein comprising hepatocyte growth factor/scatter factor and other protein. The term "HGF" as used herein also embraces hepatocyte growth factor/scatter factor isolated from species other than human.

As used herein, the term "c-Met" refers to an HGF receptor. It embraces a purified receptor, fragments of the receptor, fragments of a chemically synthesized receptor, derivatives or mutation variants of the receptor, and fused protein comprising the receptor and other protein. The term "c-Met" also embraces an HGF receptor isolated from species other than human.

As used herein, the terms "hepatocyte growth factor" and "HGF" generally refer to a growth factor having 6 domains (finger, Kringle 1, Kringle 2, Kringle 3, Kringle 4 and serine protease domains). A fragment of HGF has a smaller number of domains, and a variant of HGF may have some HGF domains in plural numbers. Both are allowed as long as the ability to bind to the HGF receptor is retained. The terms "hepatocyte growth factor" and "HGF" embrace a hepatocyte growth factor derived from human ("huHGF") and non-human mammals, especially rat. As used herein, the terms embrace mature, pre, pre-pro and pro forms purified from a naturally occurring source, synthesized chemically, or produced by recombination. Human HGF is encoded by the cDNA sequence recorded by Miyazawa et al. or Nakamura et al. The sequences recorded by them differ in 14 amino acids. The reason for the differences is not entirely clear. Polymorphism or cloning artifacts are among the possibilities.

Both sequences are specifically encompassed by the foregoing terms. It will be understood that natural allelic variations exist and can occur among individuals, as demonstrated by one or more difference(s) in the amino acid sequence of each individual. The terms "hepatocyte growth factor" and "HGF" specifically include delta 5 huHGF.

The terms "HGF receptor" and "c-Met" as used herein refer to a cellular receptor for HGF, which typically includes an extracellular domain, a transmembrane domain and an intracellular domain, as well as variants and fragments thereof which retain the ability to bind to HGF. The terms "HGF receptor" and "c-Met" include the polypeptide molecule that comprises the full-length, native amino acid sequence encoded by the gene variously known as $p190^{MET}$. This definition specifically encompasses soluble forms of HGF receptor and HGF receptors from natural sources, synthetically produced in vitro or obtained by genetic manipulation including methods of recombinant DNA technology. The HGF receptor variants or fragments preferably share at least about 65% sequence homology, and more preferably about 75% sequence homology with any domain of the human c-Met amino acid sequence.

The terms "agonist" and "agonistic" as used herein refer to or describe a molecule which is capable of, directly or indirectly, substantially inducing, promoting or enhancing biological activity of HGF or activation of HGF receptor.

The terms "cancer", "cancerous" and "malignant" refer to or describe the physiological condition in mammals that is typically characterized by unregulated cell growth. Examples of cancer include but are not limited to carcinoma, lymphoma, sarcoma, blastoma and leukemia. More particular examples of such cancers include squamous cell carcinoma, lung cancer, pancreatic cancer, cervical cancer, bladder cancer, liver cancer, breast cancer, colon cancer and head and neck cancer. Although the term "cancer" used herein is not limited to particular types of diseases, the method according to the present invention seems to be particularly effective for cancers in mammals that are known to be accompanied by increased level of HGF or c-Met expression.

The terms "treating", "treatment" and "therapy" as used herein refer to curative therapy, prophylactic therapy and preventive therapy.

The term "mammal" as herein refers to any mammal classified as a mammal, including human, cow, horse, dog and cat. In a preferred embodiment of the present invention, the mammal is a human.

When increased levels of c-Met and HGF are observed in hypertension, arteriosclerosis, myocardial infarction and rheumatoid arthritis, the compound of the present invention is effective for treating the diseases.

The term "treatment" embraces therapeutic measures as well as prophylactic measures (inhibition of onset of disorders or retardation of onset of pre-clinically explicit disorders in individuals).

The term "pharmaceutically acceptable derivative" refers to a salt or ester of the compound of the present invention, other compound that may provide the compound of the present invention (directly or indirectly) or otherwise inhibit angiogenesis when administered to a patient, a metabolite thereof, or a residue thereof.

The phrase "therapeutically effective amount" is meant to refer to an amount of each agent that will accomplish the improvement of the severity or occurrence of the disease while avoiding undesired adverse reactions. For example, a therapeutically effective amount of an antitumor agent will provide the effect of prolonging the survival period of a patient, suppressing proliferation of tumors or leading to degeneration of tumors.

The present invention also provides a method for preparing the compound represented by Chemical Formula 1. And, the compound represented by Chemical Formula 1 includes a pharmaceutically acceptable salt thereof. The term "pharmaceutically acceptable salt" includes a salt commonly used to form an alkali metal salt and an addition salt of free acid or free base. Although the properties of the salt are not particularly important, it should be pharmaceutically acceptable. A pharmaceutically acceptable acid addition salt of the compound represented by Chemical Formula 1 may be prepared form an inorganic acid or an organic acid. Examples of the inorganic acid include hydrochloric acid, hydrobromic acid, hydriodic acid, nitric acid, carbonic acid, sulfuric acid and phosphoric acid. Suitable organic acids may be selected from aliphatic, alicyclic, aromatic, arylaliphatic, heterocyclic, carboxylic and sulfonic organic acids. Examples include formic acid, acetic acid, adipic acid, butyric acid, propionic acid, succinic acid, glycolic acid, gluconic acid, lactic acid, malic acid, tartaric acid, citric acid, ascorbic acid, glucuronic acid, maleic acid, fumaric acid, pyruvic acid, aspartic acid, glutamic acid, benzoic acid, anthranilic acid, mesylic acid, 4-hydroxybenzoic acid, phenylacetic acid, mandelic acid, embonic acid (pamoic acid), methanesulfonic acid, ethanesulfonic acid, ethanedisulfonic acid, benzenesulfonic acid, pantothenic acid, 2-hydroxyethanesulfonic acid, toluenesulfonic acid, sulfanilic acid, cyclohexylaminosulfonic acid, camphoric acid, camphorsulfonic acid, digluconic acid, cyclopentanepropionic acid, dodecylsulfonic acid, glucoheptanoic acid, glycerophosphonic acid, heptanoic acid, hexanoic acid, 2-hydroxy-ethanesulfonic acid, nicotinic acid, 2-naphthalenesulfonic acid, oxalic acid, palmoic acid, pectinic acid, persulfuric acid, 2-phenylpropionic acid, picric acid, pyvalic acid, propionic acid, succinic acid, tartaric acid, thiocyanic acid, undecanoic acid, stearic acid, alginic acid, β-hydroxybutyric acid, salicylic acid, galactaric acid and galacturonic acid. Examples of the pharmaceutically acceptable base addition salt of the compound represented by Chemical Formula 1 include metal salts such as aluminum, calcium, lithium, magnesium, potassium, sodium and zinc salts, organic base including primary, secondary or amine and substituted amine such as cyclic amine, e.g. caffeine, arginine, diethylamine, N-ethylpiperidine, aistidine, glucamine, isopropylamine, lysine, morpholine, N-ethylmorpholine, piperazine, piperidine, triethylamine and trimethylamine. All of these salts may be prepared by conventional methods from the corresponding compound of the present invention by reacting, for example, the appropriate acid or base with the compound represented by Chemical Formula 1. When a base group and an acid group are present in the same molecule, the compound represented by Chemical Formula 1 may also form an internal salt.

Synthesis Process

Specific compounds of the present invention, which are represented by Chemical Formula 1, may be prepared according to the following reaction schemes. The compounds are easily synthesized using the synthesis methods known to those skilled in the art. Tautomers and solvates (e.g. hydrate) of the compound represented by Chemical Formula 1 are also included in the scope of the present invention. Solvation techniques are known in the art. Accordingly, the compound of the present invention may be in free or hydrated form, and may be obtained from the methods exemplified by the following reaction schemes. In the following reaction schemes, the substituents are the same as defined in Chemical Formula 1 unless specified otherwise.

Abbreviations used in the specification are as follows.

HBTU: O-benzotriazol-1-yl-N,N,N',N'-tetramethyluronium hexafluorophosphate

HATU: O-(7-azabenzotriazol-1-yl)-N,N,N',N-tetramethyluronium hexafluorophosphate PyBop: benzotriazol-1-yl-oxy-tripyrrolidino-phosphonium hexafluorophosphate $Pd_2(dba)_3$: bis(dibenzylideneacetone)palladium BINAP: 2,2'-bis(diphenylphosphino)-1,1-binaphthyl TEAC: bis(tetraethylammonium)carbonate $Et_2O$: diethyl ether DBU: 1,8-diazabicyclo[5.4.0]undec-7-ene DIBAL: diisobutylaluminum hydride DIAD: diisopropyl azodicarboxylate DIEA: diisopropylethylamine DMF: dimethylformamide DMAP: 4-dimethylaminopyridine DMSO: dimethyl sulfoxide EDC, EDCl: 1-(3-dimethylaminopropyl)-3-ethylacrbodiimide hydrochloride DPPA: diphenylphosphoryl azide EtOAc: ethyl acetate FBS: fetal bovine serum HOBt: 1-hydroxybenzotriazole hydrate LiHMDS: lithium bis(trimethylsilyl)amide LDA: lithium diisopropylamide MCPBA: meta-chloroperbenzoic acid $CH_2Cl_2$, DCM: methylene chloride NMP: N-methylpyrrolidone Pd/C: palladium on carbon $Pd(OAc)_2$: palladium(II) acetate $Pd(OH)_2$: palladium hydroxide $Pd(PPh_3)_4$: tetrakis(triphenylphosphine)palladium $Pd(dppf)Cl_2$: 1,1-bis(diphenylphosphino)ferrocene palladium chloride PBS: phosphate buffered saline RT: room temperature SEM: 2-(trimethylsilyl)ethoxymethyl TBTU: O-benzotriazol-1-yl-N,N,N',N'-tetramethyluronium tetrafluoroborate THF: tetrahydrofuran Et3N, TEA: triethylamine TFA: trifluoroacetic acid $P(t-Bu)_3$: tri(tert-butyl)phosphine In general, the target heterocyclic compound represented by Chemical Formula 1 may be prepared according to Reaction Schemes 1 to 3.

[Reaction Scheme 1]

In Reaction Scheme 1, Q, X, Y, Z, $R^1$, $R^2$ and $R^3$ are the same as defined in Chemical Formula 1.

Specifically, a compound with Y=Z=CH and Q=

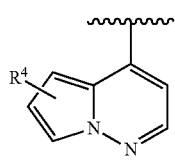

be prepared according to Reaction Scheme 2.

[Reaction Scheme 2]

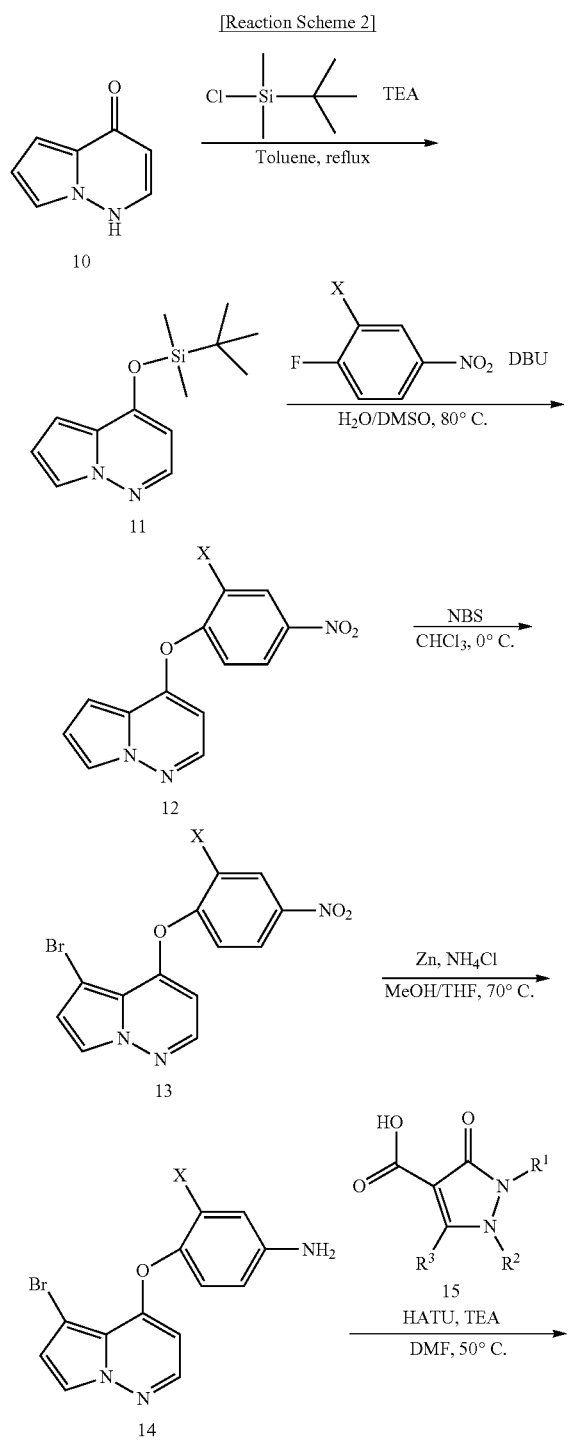

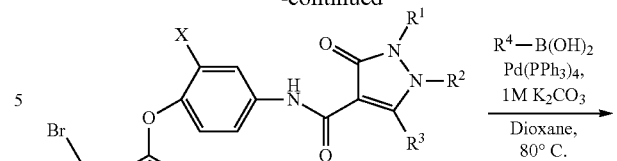

-continued

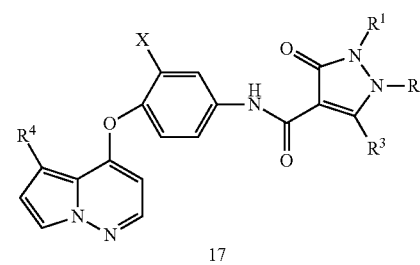

According to Reaction Scheme 2, Compound 10 (pyrrolo[1,2-b]pyridazin-4(1H)-one) is silylated to obtain compound 11. After sequentially adding water, a 3-X-4-fluoronitrobenzene derivative and 1,8-diazabicyclo[5,4,0]-undec-7-ene (DBU) to a solution of compound 11 in dimethyl sulfoxide, reaction is carried out to obtain Compound 12. Compound 12 is brominated to obtain compound 13. The nitro group of compound 13 is reduced to an amino group using zinc powder and ammonium chloride to obtain compound 14. Compound 14 and a pyrazole-4-carboxylic acid derivative (Compound 15) are dissolved in DMF. After sequentially adding HATU and triethylamine are sequentially added, the reaction is carried out to obtain compound 16. Compound 16 and an $R^4$-containing boronic acid [$R^4$—B(OH)$_2$] are dissolved in dioxane. After sequentially adding potassium carbonate aqueous solution and Pd(PPh$_3$)$_4$, reaction is carried out to obtain compound 17.

Specifically, a compound with Y=Z=CH and Q=

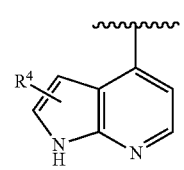

may be prepared according to Reaction Scheme 3.

[Reaction Scheme 3]

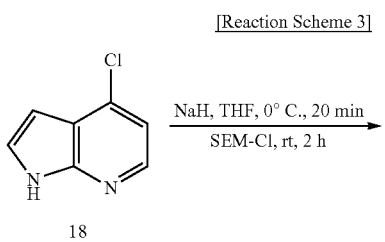

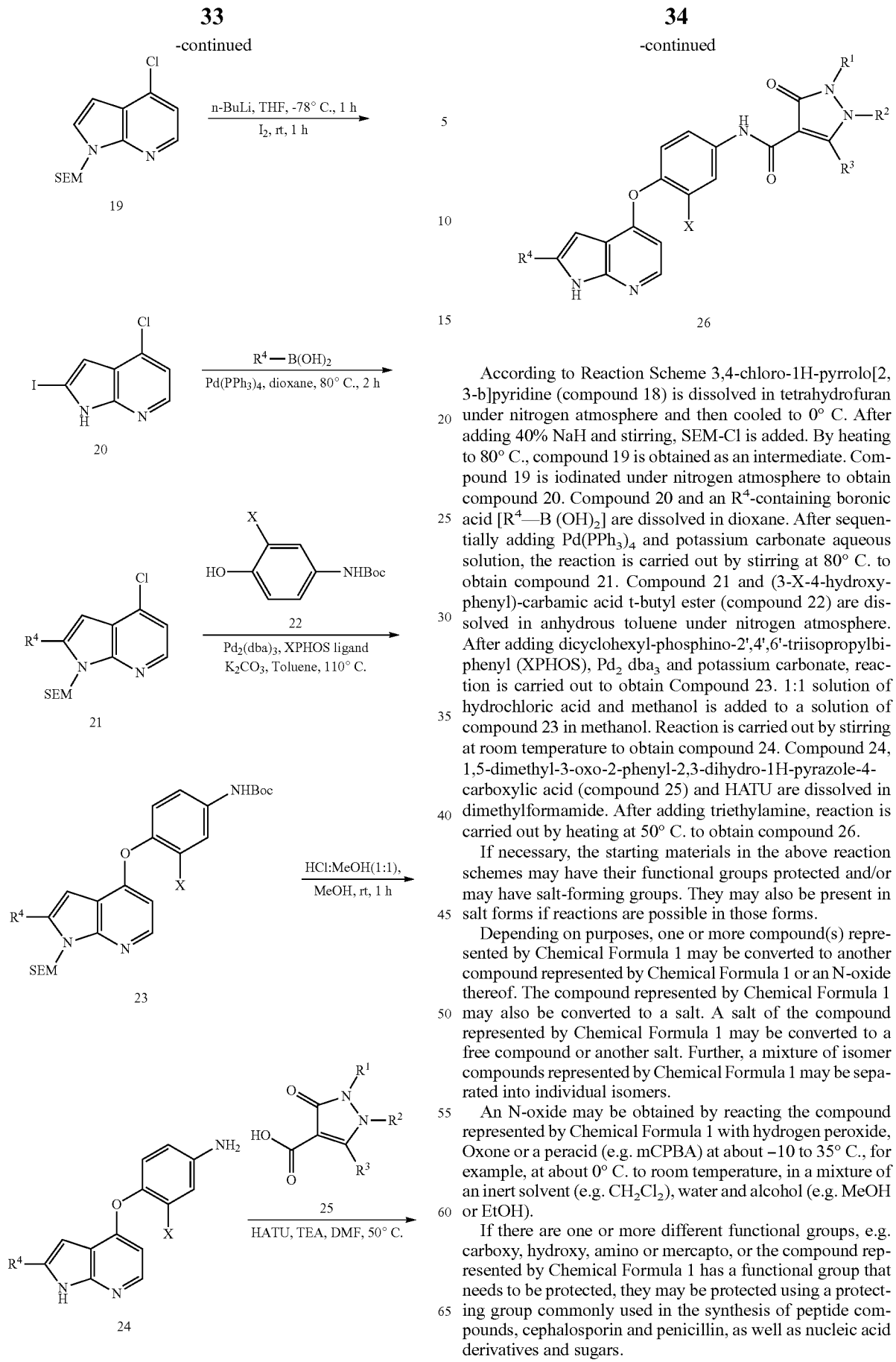

According to Reaction Scheme 3,4-chloro-1H-pyrrolo[2,3-b]pyridine (compound 18) is dissolved in tetrahydrofuran under nitrogen atmosphere and then cooled to 0° C. After adding 40% NaH and stirring, SEM-Cl is added. By heating to 80° C., compound 19 is obtained as an intermediate. Compound 19 is iodinated under nitrogen atmosphere to obtain compound 20. Compound 20 and an $R^4$-containing boronic acid [$R^4$—B (OH)$_2$] are dissolved in dioxane. After sequentially adding Pd(PPh$_3$)$_4$ and potassium carbonate aqueous solution, the reaction is carried out by stirring at 80° C. to obtain compound 21. Compound 21 and (3-X-4-hydroxyphenyl)-carbamic acid t-butyl ester (compound 22) are dissolved in anhydrous toluene under nitrogen atmosphere. After adding dicyclohexyl-phosphino-2',4',6'-triisopropylbiphenyl (XPHOS), Pd$_2$ dba$_3$ and potassium carbonate, reaction is carried out to obtain Compound 23. 1:1 solution of hydrochloric acid and methanol is added to a solution of compound 23 in methanol. Reaction is carried out by stirring at room temperature to obtain compound 24. Compound 24, 1,5-dimethyl-3-oxo-2-phenyl-2,3-dihydro-1H-pyrazole-4-carboxylic acid (compound 25) and HATU are dissolved in dimethylformamide. After adding triethylamine, reaction is carried out by heating at 50° C. to obtain compound 26.

If necessary, the starting materials in the above reaction schemes may have their functional groups protected and/or may have salt-forming groups. They may also be present in salt forms if reactions are possible in those forms.

Depending on purposes, one or more compound(s) represented by Chemical Formula 1 may be converted to another compound represented by Chemical Formula 1 or an N-oxide thereof. The compound represented by Chemical Formula 1 may also be converted to a salt. A salt of the compound represented by Chemical Formula 1 may be converted to a free compound or another salt. Further, a mixture of isomer compounds represented by Chemical Formula 1 may be separated into individual isomers.

An N-oxide may be obtained by reacting the compound represented by Chemical Formula 1 with hydrogen peroxide, Oxone or a peracid (e.g. mCPBA) at about −10 to 35° C., for example, at about 0° C. to room temperature, in a mixture of an inert solvent (e.g. CH$_2$Cl$_2$), water and alcohol (e.g. MeOH or EtOH).

If there are one or more different functional groups, e.g. carboxy, hydroxy, amino or mercapto, or the compound represented by Chemical Formula 1 has a functional group that needs to be protected, they may be protected using a protecting group commonly used in the synthesis of peptide compounds, cephalosporin and penicillin, as well as nucleic acid derivatives and sugars.

The protecting group may be already present in a precursor and is intended to protect the functional group in question from undesired secondary reactions, e.g. acylation, etherification, esterification, oxidation, solvolysis and other similar reactions. The protecting group can be removed easily, i.e. without undesired secondary reactions taking place, for example by solvolysis, reduction or photolysis, and also enzymatically, for example, under physiological conditions, and does not exist in the end product. Those skilled in the art will know or easily select the protecting groups that are appropriate for the above and following reactions.

In the following processes, the functional groups of the staring materials that did not participate in the reaction as desired may be present as unprotected or protected by one or more protecting group (s). Later, all or some of the protecting groups are removed according to the aforesaid method.

A salt of a compound represented by Chemical Formula 1 having a salt-forming group may be prepared according to a known method. An acid addition salt of the compound represented by Chemical Formula 1 may be prepared by treating with an acid or a suitable anion exchange reagent. A salt with two acid molecules (for example, a dihalogenide of the compound represented by Chemical Formula 1) may also be converted into a salt with one acid molecule per compound (for example, a monohalogenide). This may be done by heating to a melt or, for example, by heating as a solid under a high vacuum at elevated temperature, for example from 130 to 170° C., so that one acid molecule is expelled per molecule of the compound represented by Chemical Formula 1.

A salt can usually be converted to a free compound, for example, by treating with a suitable basic compound, e.g. alkali metal carbonate, alkali metal hydrogen carbonate or alkali metal hydroxide, typically potassium carbonate or sodium hydroxide.

All the processes described herein may be performed under a known reaction condition, preferably under a specified condition, in the absence of or usually in the presence of a solvents or diluents that, preferably such as are inert to the reagents used and able to dissolve these, in the absence or presence of catalysts, condensing agents or neutralizing agents, for example ion exchangers, typically cation exchangers (e.g. in the H$^+$ form), depending on the type of reaction and/or reactants, at reduced, normal or elevated temperature, for example in the range from about −100° C. to about 190° C., preferably from about −80° C. to about 150° C., for example, from about −80° C. to about 60° C., at room temperature, from about −20° C. to about 40° C. or at the boiling point of the solvent used, under atmospheric pressure or in a closed vessel, where appropriate, under pressure and/or in an inert atmosphere, for example, under argon or nitrogen atmosphere.

Salts may be present in all starting materials and intermediates, if these contain salt-forming groups. Salts may also be present during the reaction of such compounds, provided the reaction is not disturbed thereby.

Under certain circumstance, typically in hydrogenation, a stereoselective reaction may be achieved, for example, to allow easier obtainment of individual isomers.

Solvents that may be used in the reactions may be selected from the followings: water, ester, typically lower alkyl-lower alkanoate (e.g. EtOAc), ether, typically aliphatic ether (e.g. Et$_2$O) or cyclic ether (e.g. THF), liquid aromatic hydrocarbon, typically benzene or toluene, alcohol, typically MeOH, EtOH, 1-propanol or IPOH, nitrile, typically CH$_3$CN, halogenated hydrocarbon, typically CH$_2$Cl$_2$, acid amide, typically DMF, base, typically heterocyclic nitrogenous base (e.g. pyridine), carboxylic acid, typically lower alkanecarboxylic acid (e.g. AcOH), carboxylic acid anhydride, typically lower alkanoic anhydride (e.g. acetic anhydride), cyclic, linear or branched hydrocarbon, typically cyclohexane, hexane or isopentane, and mixtures of these solvent (e.g. aqueous solution). Such solvent mixtures may also be employed in such processes as chromatography.

In accordance with the present invention, a specific material may be prepared from a compound that may be obtained transiently at any step. An omitted step may be performed and the process may be stopped at any step. Also, the starting material may be formed under the reaction condition, or the starting material may be used in the form of a reactive derivative or salt. Or, a compound that may be obtained according to the method of the present invention may be prepared to be used in the other process. In a preferred embodiment, a material is prepared from the starting material that gives rise to the material.

The compound represented by Chemical Formula 1 includes a salt thereof and may be obtained in a hydrated form. Crystals of the compounds may include, for example, the solvent (existing as solvate) used for crystallization.

Not only the novel starting material and/or intermediate, but also the preparation method thereof is a subject matter of the present invention. In a preferred embodiment, a reaction condition is selected so that the desired compound can be obtained from the starting material.

The starting material of the present invention may be known or commercially available or may be synthesized according to a method known in the art.

When preparing the starting material, the functional groups that do not participate in the reaction may be needed to be protected.

Preferred protecting groups, and introduction and removal thereof are described in the foregoing description or in the following examples.

All the starting materials are previously known, may be prepared according to known methods, or are commercially available. Especially, they may be prepared according to the description of the examples.

In general, the compound of the present invention may have one or more asymmetric carbon atom(s). Therefore, the compound of the present invention may be present as optical isomers, racemates or non-racemic mixtures thereof. The optical isomers can be obtained by resolving the racemic mixture according to a common method, for example by treating with an optically active acid or base, thereby forming diastereomeric salts. Examples of suitable acids include tartaric acid, diacetyltartaric acid, dibenzoyltartaric acid, ditoloyltartaric acid and camphorsulfonic acid. Then, the diastereomeric mixture is separated by crystallization followed by freeing of the optically active base from the salt. Another method for the separation of optical isomers is to use a chiral chromatographic column optimally selected to maximize the separation of enantiomers. Another available method is to react the compound of the present invention with an activated, optically pure acid or optically pure isocyanate to synthesize a covalently bonded diastereomer molecule. The synthesized diastereomer is separated by a common method such as chromatography, distillation, crystallization or sublimation, and then hydrolyzed to obtain an enantiomerically pure compound. Optically active compounds of the present invention may be prepared from optically active starting materials. These isomers may be in the form of free acids, free bases, esters or salts.

Since the compound of the present invention has one or more asymmetric center(s), it may be present as racemate, racemic mixture, scalemic mixture, enantiomer, individual diastereomers and diastereomeric mixture. All of these isomers are explicitly encompassed in the present invention. The present invention also explicitly encompasses all tautomer forms of the compounds described herein. The compound may also be in cis-, trans-, E- or Z-isomer form. All of these isomer forms are also explicitly encompassed in the present invention. And, all crystal forms of the compounds described herein are explicitly encompassed in the present invention.

A cyclic substituent (e.g. phenyl, thienyl, and the like.) may be attached to a specific atom. This means that the substituent may or may not be fixed at specific atom.

The compound of the present invention may include a heterocyclic ring attached to another ring. The heterocyclic ring may be attached via a carbon atom or a heteroatom of the ring system.

Any of the compounds with the chemical formulae described herein may be synthesized by the methods disclosed herein.

In the preparation methods described in this specification, the steps may be performed sequentially and, if necessary, further protecting/deprotecting step may precede or follow. Additional inert solvent, reagent, for example base (e.g. LDA, DIEA, pyridine, $K_2CO_3$, and the like), catalyst, or salts thereof may be used under suitable reaction conditions. An intermediate may be isolated or subjected to the next step with or without a purification process. The purification may be performed according to methods known in the art. They include, for example, crystallization, chromatography (liquid-phase, gas-phase), extraction, distillation, pulverization, reversed-phase HPLC, or the like. Reaction conditions such as temperature, period, pressure and atmosphere (e.g., inert gas or ambient atmosphere) are known in the art and may be adjusted appropriately depending on the particular reactions.

As will be recognized by those skilled in the art, the foregoing synthesis reaction schemes are not intended to comprehensively include all the possible means of synthesizing the compounds of the present invention. Those skilled in the art will also appreciate other additional methods. In the foregoing reaction schemes, various synthesis steps may be performed alternatingly or sequentially to obtain the desired compounds.

The compound of the present invention may be modified by attaching an adequate functional group to selectively enhance its biological features. Such modification is known in the art and includes those enhancing biological infiltration into a given biological system (e.g. cardiovascular system, lymphatic system, CNS), increasing oral availability, increasing solubility to allow administration by injection, altering metabolism and changing secretion rate.

The foregoing detailed description is given to describe examples of the general synthesis procedure which is included in the scope of the present invention. The detailed description is provided for illustrative purposes only and is not intended to limit the scope of the present invention.

Hereunder is given examples and preparations according to the present invention. The following examples are only exemplary and the present invention is not limited thereby. It is to be understood that there may exist other embodiments that are included in the intent and scope of the present invention.

EXAMPLES

Unless specified otherwise, all materials were acquired from ordinary suppliers and were used without further purification.

For analysis of compounds, all the $^1$H-NMR spectra were measured using Varian's Unity Inova 400 Series and all the mass spectra were measured using Shimadzu's LCMS-2010EV Series.

LCMS analysis was performed using Shimadzu's LCMS-2010 EV under the following conditions:
Degasser: DGU-20A
Pump: LC-20AD
Autosampler: SIL-20A
UV/Vis detector: SPD-20A
Column oven: CTO-20A
Solvent: 90% CAN (0.1% TFA) in $H_2O$
Wavelength: 254 nm
Injection volume: 5 µL
Column: XDB C18 5 m, 4.5×150 mm (Agilent)

Preparation Example 1

1,5-Dimethyl-3-oxo-2-phenyl-2,3-dihydro-1H-pyrazole-4-carboxylic acid

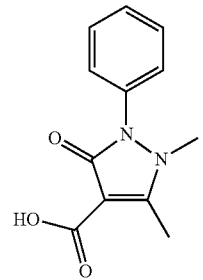 [SMILES: Cc1c(C(=O)O)c(=O)n(-c2ccccc2)n1C]

1,5-Dimethyl-3-oxo-2-phenyl-2,3-dihydro-1H-pyrazole-4-carboxylic acid, which is one of the intermediate compounds used in the synthesis of the compound of the present invention, was prepared as follows:

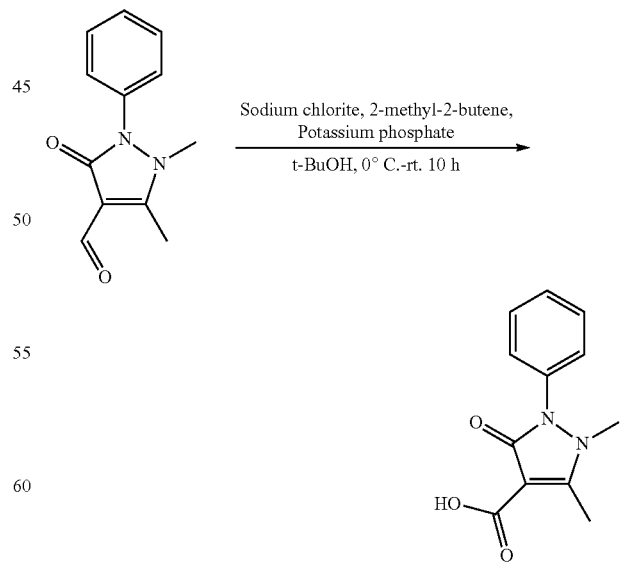

To a mixture of 1-benzyl-5-methyl-3-oxo-2-phenyl-2,3-dihydro-1H-pyrazole-4-carboxaldehyde (1 g, 4.624 mmol) in butyl alcohol were added to $NaClO_2$ (1.254 g, 13.873 mmol)

in an aqueous solution and potassium phosphate monobasic monohydrate (3.146 g, 23.12 mmol) in an aqueous solution slowly at 0° C. The resulting reaction mixture was slowly heated to room temperature and stirred for 10 hours. NaClO₃ (1 g) was further added while monitoring the reaction. Following the addition of sodium chlorite, the reaction mixture was stirred and then extracted with ethyl acetate. The organic layer was washed with, dried with Na₂SO₄ and then filtered. The filtrate was concentrated under reduced pressure. The resulting residue was washed with 20% ethyl acetate solution in small amount of hexane. The target compound was obtained as a white solid (808 mg, 3.48 mmol, 75% yield).

¹H NMR (400 MHz, DMSO): 12.22 (br s, 1H), 7.61-7.42 (m, 5H), 3.36 (s, 3H), 2.59 (s, 3H).

Preparation Example 2

2-(4-Fluorophenyl)-1,5-dimethyl-3-oxo-2,3-dihydro-1H-pyrazole-4-carboxylic acid

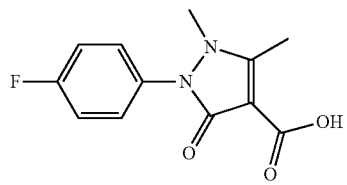 [SMILES: Cc1c(C(=O)O)c(=O)n(-c2ccc(F)cc2)n1C]

2-(4-Fluorophenyl)-1,5-dimethyl-3-oxo-2,3-dihydro-1H-pyrazole-4-carboxylic acid, which is one of the common intermediates used in the synthesis of compounds of the present invention, was prepared as follows:

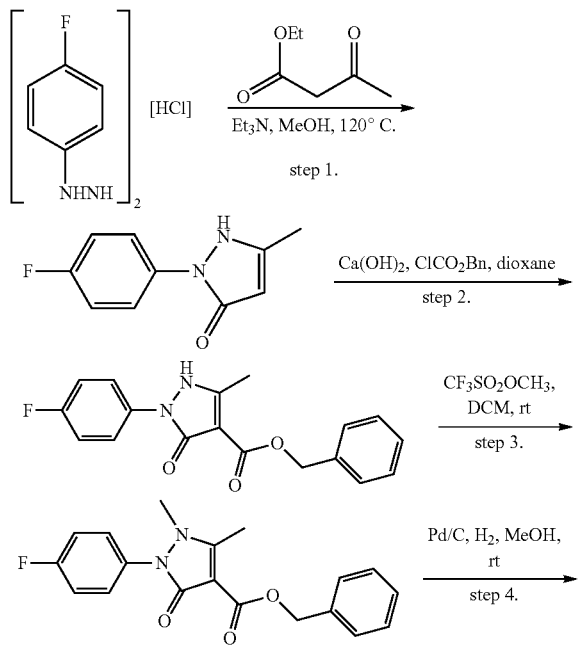

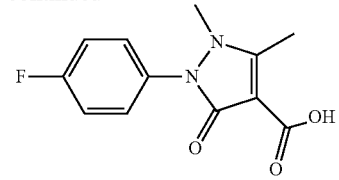

(Step 1) 2-(4-fluorophenyl)-5-methyl-1H-pyrazol-3(2H)-one

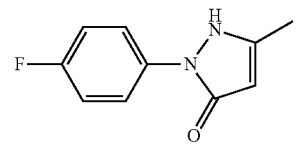

(4-Fluorophenyl)hydrazine hydrochloride (20.0 g, 0.123 mol) was added to a solution of triethylamine (20.5 mL) in methanol (350 mL). Then, a solution of ethyl acetoacetate (16.0 g, 0.123 mol) in methanol (50 mL) was added. The resulting reaction mixture was stirred for 4 hours under reflux and extracted with dichloromethane and sodium chloride aqueous solution. The aqueous layer was extracted again with dichloromethane. All the organic layers were collected, dried with Na₂SO₄ and then filtered. The filtrate was concentrated. The resulting residue was purified by silica gel chromatography (ethyl acetate:hexane=1:2). The target compound was yielded (21.0 g, 89% yield).

MS (ESI pos. ion) m/z: 193 (MH⁺). Calc'd exact mass for C₁₀H₉FN₂O: 192.07.

¹H NMR (400 MHz, CDCl₃): 7.84-7.81 (m, 2H), 7.09-7.05 (m, 2H), 3.43 (s, 1H), 3.07 (br s, 1H), 2.19 (s, 3H).

(Step 2) benzyl-2-(4-fluorophenyl)-5-methyl-3-oxo-2,3-dihydro-1H-pyrazole-4-carboxylate

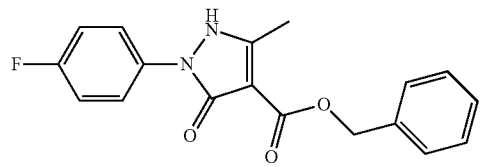 [SMILES: Cc1[nH]n(-c2ccc(F)cc2)c(=O)c1C(=O)OCc1ccccc1]

2-(4-Fluorophenyl)-5-methyl-1H-pyrazol-3(2H)-one (20.3 g, 0.105 mol) and calcium hydroxide (17.2 g, 0.232 mol) were suspended in anhydrous 1,4-dioxane (200 mL). The resulting suspension was heated at 50° C. for 20 minutes. The heated suspension was cooled to 10° C. and a solution of benzyl chloroformate (14.9 mL, 0.105 mol) in dioxane (10 mL) was added. The resulting reaction mixture was heated at 90° C. for 3 hours. Upon completion of the reaction, the reaction mixture was slowly cooled to 0° C. After adding 1 M hydrochloric acid, the mixture was stirred at room temperature overnight. Then, the produced solid was collected by filtration, washed with cold ethanol and ether, and dried in vacuum to give the target compound (22.88 g, 66% yield).

MS (ESI pos. ion) m/z: 327 (MH+). Calc'd exact mass for C$_{18}$H$_{15}$FN$_2$O$_3$: 326.11.

$^1$H NMR (400 MHz, CDCl$_3$): 7.82-7.79 (m, 2H), 7.40-7.29 (m, 5H), 7.09-7.04 (m, 2H), 5.30 (s, 1H), 5.19 (s, 1H), 2.38 (s, 3H).

(Step 3) benzyl 2-(4-fluorophenyl)-1,5-dimethyl-3-oxo-2,3-dihydro-1H-pyrazole-4-carboxylate

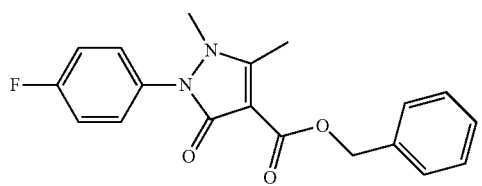 [SMILES: Cc1c(C(=O)OCc2ccccc2)c(=O)n(-c2ccc(F)cc2)n1C]

To a solution of benzyl 2-(4-fluorophenyl)-5-methyl-3-oxo-2,3-dihydro-1H-pyrazole-4-carboxylate (8.0 g, 0.024 mol) in dichloromethane (80 mL), methyl trifluoromethanesulfonate (4.8 g, 0.029 mol) was added and stirred at room temperature for 24 hours. The resulting mixture was extracted with dichloromethane and saturated baryta water. After phase separation, the aqueous layer was extracted again with dichloromethane. All the organic layers were collected, dried with Na$_2$SO$_4$ and then filtered. The filtrate was concentrated under reduced pressure. The resulting residue was purified by silica gel chromatography (ethyl acetate:hexane=4:1) to give the target compound (2.69 g, 32% yield).

MS (ESI pos. ion) m/z: 341 (MH+) Calc'd exact mass for C$_{19}$H$_{17}$FN$_2$O$_3$: 340.12.

$^1$H NMR (400 MHz, CDCl$_3$): 7.51-7.48 (m, 2H), 7.35-7.26 (m, 5H), 7.19-7.15 (m, 2H), 5.33 (s, 1H), 3.28 (s, 3H), 2.62 (s, 3H).

(Step 4) 2-(4-fluorophenyl)-1,5-dimethyl-3-oxo-2,3-dihydro-1H-pyrazole-4-carboxylic acid

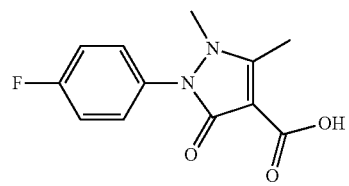 [SMILES: Cc1c(C(=O)O)c(=O)n(-c2ccc(F)cc2)n1C]

To a solution of benzyl 2-(4-fluorophenyl)-1,5-dimethyl-3-oxo-2,3-dihydro-1H-pyrazole-4-carboxylate (2.6 g, 7.64 mmol) in methanol (25 mL), Pd/C (0.5 g) was added. While blowing in hydrogen gas, the mixture was stirred for 8 hours. The resulting reaction mixture was filtered by passing through a celite pad. The filtrate was concentrated under reduced pressure. The target compound was yielded (1.8 g, 94% yield).

MS (ESI pos. ion) m/z: 251 (MH+) Calc'd exact mass for C$_{12}$H$_{11}$FN$_2$O$_3$: 250.08.

$^1$H NMR (400 MHz, CDCl$_3$): 11.94 (br s, 1H), 7.36-7.32 (m, 2H), 7.27-7.22 (m, 2H), 3.36 (s, 3H), 2.69 (s, 3H).

Example 1

N-(4-(5-Bromopyrrolo[1,2-b]pyridazin-4-yloxy)-3-fluorophenyl)-1,5-dimethyl-3-oxo-2-phenyl-2,3-dihydro-1H-pyrazole-4-carboxamide

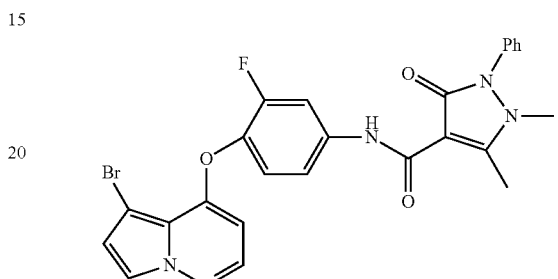

The target compound was prepared as follows:

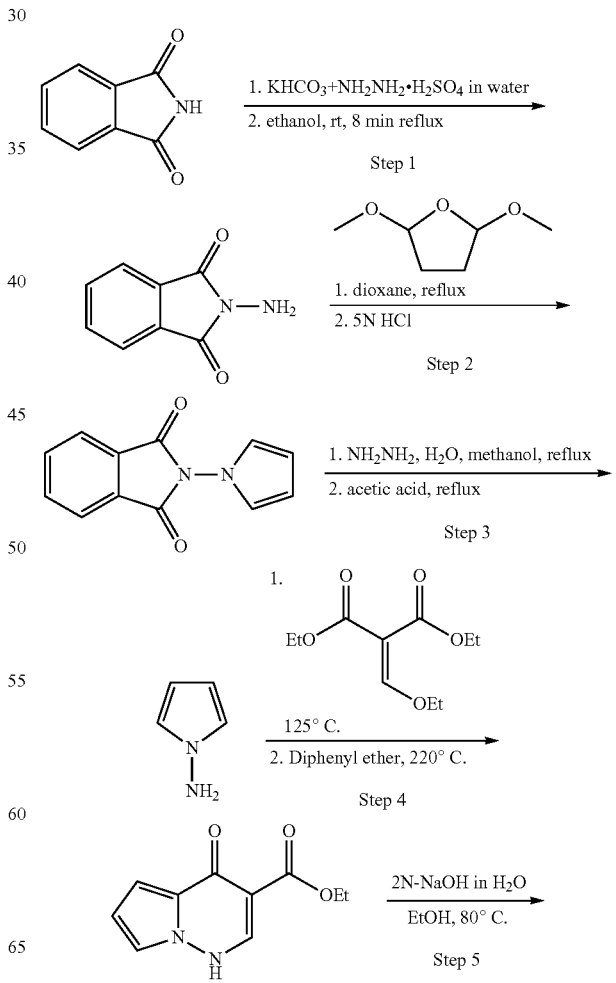

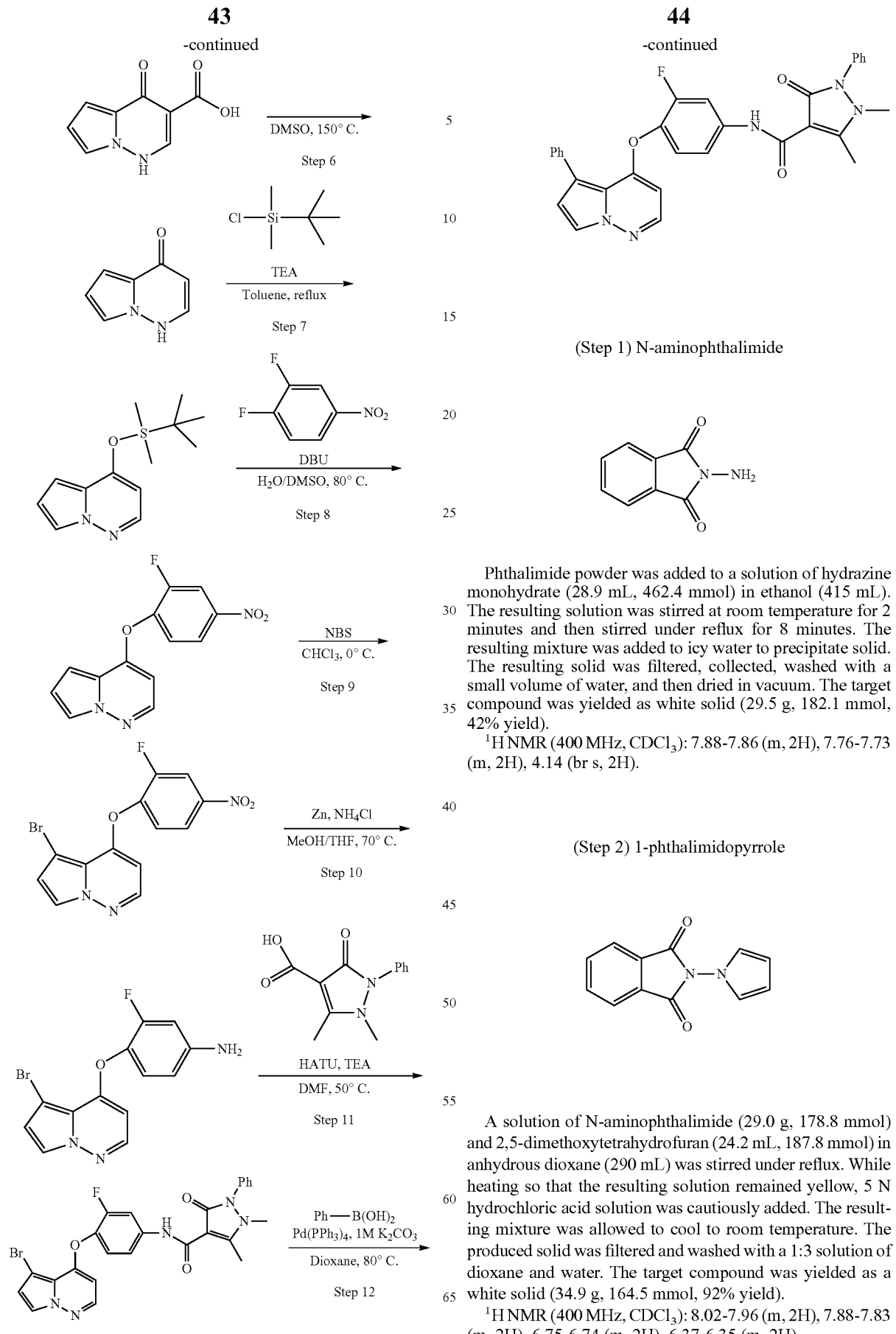

(Step 1) N-aminophthalimide

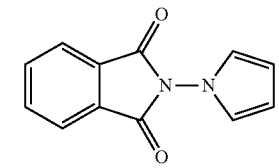 [SMILES: O=C1c2ccccc2C(=O)N1n1cccc1]

Phthalimide powder was added to a solution of hydrazine monohydrate (28.9 mL, 462.4 mmol) in ethanol (415 mL). The resulting solution was stirred at room temperature for 2 minutes and then stirred under reflux for 8 minutes. The resulting mixture was added to icy water to precipitate solid. The resulting solid was filtered, collected, washed with a small volume of water, and then dried in vacuum. The target compound was yielded as white solid (29.5 g, 182.1 mmol, 42% yield).

$^1$H NMR (400 MHz, CDCl$_3$): 7.88-7.86 (m, 2H), 7.76-7.73 (m, 2H), 4.14 (br s, 2H).

(Step 2) 1-phthalimidopyrrole

A solution of N-aminophthalimide (29.0 g, 178.8 mmol) and 2,5-dimethoxytetrahydrofuran (24.2 mL, 187.8 mmol) in anhydrous dioxane (290 mL) was stirred under reflux. While heating so that the resulting solution remained yellow, 5 N hydrochloric acid solution was cautiously added. The resulting mixture was allowed to cool to room temperature. The produced solid was filtered and washed with a 1:3 solution of dioxane and water. The target compound was yielded as a white solid (34.9 g, 164.5 mmol, 92% yield).

$^1$H NMR (400 MHz, CDCl$_3$): 8.02-7.96 (m, 2H), 7.88-7.83 (m, 2H), 6.75-6.74 (m, 2H), 6.37-6.35 (m, 2H).

(Step 3) N-aminopyrrole

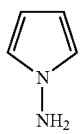

Hydrazine monohydrate (8.8 ml, 144.8 mmol) was added to a solution of 1-phthalimidopyrrole (25.6 g, 120.6 mmol) in methanol (500 mL) and stirred for 1 hour under reflux. The resulting reaction mixture was cooled to room temperature and stirred for 15 minutes under reflux after cautiously adding acetic acid. The resulting solution was filtered and methanol was removed by distillation. The resulting residue was extracted with dichloromethane after adding 40% sodium hydroxide aqueous solution. Then, the extract was concentrated and the remaining residue was purified by vacuum distillation. The target compound was yielded (6.5 g, 79.2 mmol, 66% yield).

$^1$H NMR (400 MHz, CDCl$_3$): 6.70-6.68 (m, 2H), 6.05-6.03 (m, 2H), 4.84 (br s, 2H).

(Step 4) ethyl 4-oxo-1,4-dihydropyrrole[1,2-b]pyridazin-3-carboxyate

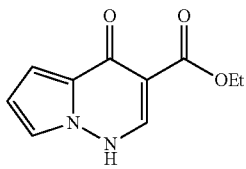 [SMILES: CCOC(=O)c1c[nH]n2cccc2c1=O]

A mixture of N-aminopyrrole (6.2 g, 75.5 mmol) and diethyl ethoxymethylenemalonate (18.2 mL, 90.6 mmol) was heated at 125° C. for 2 hours to give diethyl 2-((1H-pyrrol-1-ylamino)methylene)malonate as an intermediate and then diphenyl ether (22 mL) was added thereto. The resulting reaction mixture was heated under nitrogen atmosphere at 220° C. for 2 hours and ethanol produced during the reaction was removed by distillation. The reaction mixture with ethanol removed was cooled to room temperature and purified by silica gel chromatography. The target compound was yielded as a yellow solid (11.0 g, 53.3 mmol, 71% yield).

$^1$H NMR (400 MHz, CDCl$_3$): 12.34 (br s, 1H), 8.29 (s, 1H), 7.44 (dd, J=2.8 Hz, 1.6 Hz, 1H), 6.97 (dd, J=4.4 Hz, 1.6 Hz, 1H), 6.78-6.76 (m, 1H).

(Step 5) 4-oxo-1,4-dihydropyrrolo[1,2-b]pyridazine-3-carboxylic acid

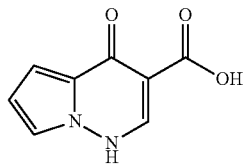 [SMILES: O=C(O)c1c[nH]n2cccc2c1=O]

2 M sodium hydroxide aqueous solution was added to a suspension of ethyl 4-oxo-1,4-dihydropyrrolo[1,2,b]pyridazin-3-carboxylate in ethanol (165 mL) and stirred overnight at 100° C. The resulting reaction mixture was cooled to room temperature, distilled under reduced pressure, and concentrated. Then, concentrated hydrochloric acid was added until pH decreased to 2. Thereafter, the solid was filtered, washed with water and dried in vacuum. The target compound obtained was subjected to the next step without further purification.

(Step 6) pyrrolo[1,2-b]pyridazin-4(1H)-one

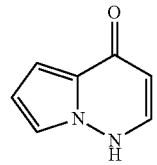

4-oxo-1,4-dihydropyrrolo[1,2-b]pyridazine-3-carboxylic acid was dissolved in dimethyl sulfoxide (110 mL) and heated at 150° C. for 1 hour. After removing the solvent by distillation under reduced pressure, the resulting residue was purified by silica gel chromatography (5% ethyl acetate in dichloromethane) to give the target compound (5.3 g, 39.5 mmol, 74% yield).

$^1$H NMR (400 MHz, CDCl$_3$): 7.88 (d, J=5.2 Hz, 1H), 7.74-7.72 (m, 1H), 6.78-6.75 (m, 1H), 6.65-6.63 (m, 1H), 5.99 (d, J=5.2 Hz, 1H).

(Step 7) 4-(t-butyldimethylsilyloxy)pyrrolo[1,2-b]pyridazine

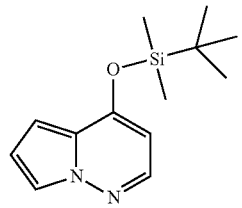 [SMILES: CC(C)(C)[Si](C)(C)Oc1ccnn2cccc12]

Pyrrolo[1,2-b]pyridazin-4(1H)-one (2.0 g, 14.9 mmol) and t-butyldimethylsilyl chloride (2.7 g, 17.9 mmol) were dissolved in anhydrous toluene under nitrogen atmosphere. After adding triethylamine (3.1 mL, 22.4 mmol), the mixture was stirred for 1 hour under reflux. Upon completion of the reaction, the produced solid was filtered and washed with a small volume of toluene. The filtrate was concentrated by distillation under reduced pressure. The resulting residue was subjected to the next step without further purification.

(Step 8) 4-(2-fluoro-4-nitrophenoxy)pyrrolo[1,2-b]pyridazine

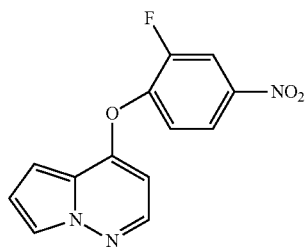 [SMILES: O=[N+]([O-])c1ccc(Oc2ccnn3cccc23)c(F)c1]

Water (0.05 mL, 2.68 mmol), 3,4-difluoronitrobenzene (1.65 mL, 14.9 mmol) and 1,8-diazabicyclo[5,4,0]-undec-7-ene (0.27 mL, 1.79 mmol) were sequentially added to a solution of 4-(t-butyldimethylsilyloxy)pyrrolo[1,2-b]pyridazines in dimethyl sulfoxide (55 mL). The resulting mixture was heated to 80° C. and stirred until 3,4-difluoronitrobenzene disappeared. Upon completion of the reaction, the mixture was extracted with dichloromethane and sodium chloride aqueous solution. The organic layer was separated, dried with anhydrous magnesium sulfate, and then filtered. The filtrate was concentrated by distillation under reduced pressure. The resulting residue was purified by silica gel chromatography (10% ethyl acetate in n-hexane) to give the target compound as a yellow solid (2.65 g, 9.70 mmol, 65% yield).

$^1$H NMR (400 MHz, CDCl$_3$): 8.19-8.11 (m, 2H), 7.92 (d, J=5.2 Hz, 1H), 7.82 (dd, J=2.8 Hz, 1.6 Hz, 1H), 7.39 (dd, J=8.8 Hz, 7.6 Hz, 1H), 6.85 (dd, J=4.4 Hz, 2.4 Hz, 1H), 6.67 (dd, J=4.4 Hz, 1.6 Hz, 1H), 5.83 (d, J=5.2 Hz, 1H).

(Step 9) 5-bromo-4-(2-fluoro-4-nitrophenoxy)pyrrolo[1,2-b]pyridazine

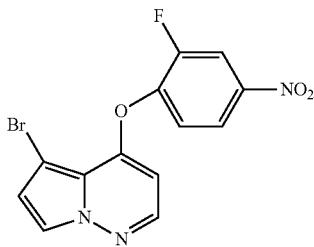

N-Bromosuccinimide (1.49 g, 8.42 mmol) was added to a solution of 4-(2-fluoro-4-nitrophenoxy)pyrrolo[1,2-b]pyridazine (2.30 g, 8.42 mmol) in anhydrous chloroform (70 mL) at 0° C. and stirred for 4 hours. Upon completion of the reaction, the resulting mixture was washed by adding water thereto. The organic layer was separated, dried with magnesium sulfate, and then filtered. The filtrate was concentrated by distillation under reduced pressure. The resulting residue was purified by silica gel chromatography (10% ethyl acetate in n-hexane) to give the target compound as a yellow solid (840 mg, 2.39 mmol, 28% yield).

$^1$H NMR (400 MHz, CDCl$_3$): 8.19-8.12 (m, 8H), 7.89 (d, J=5.2 Hz, 1H), 7.74 (d, J=5.2 Hz, 1H), 7.35 (dd, J=8.8 Hz, 7.6 Hz, 1H), 6.86 (dd, J=3.2 Hz, 0.4 Hz, 1H), 5.84 (dd, J=5.2 Hz, 0.8 Hz, 1H).

(Step 10) 4-(5-bromopyrrolo[1,2-b]pyridazin-4-yloxy)-3-fluoroaniline

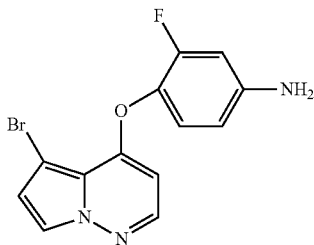 [SMILES: O=[N+]([O-])c1ccc(Oc2ccnn3ccc(Br)c23)c(F)c1]

Methanol (1.2 mL), zinc powder (300 mg, 4.57=1) and ammonium chloride (130 mg, 2.47 mmol) were sequentially added to a solution of 5-bromo-4-(2-fluoro-4-nitrophenoxy)pyrrolo[1,2-b]pyridazine (67 mg, 0.19 mmol) in tetrahydrofuran (4.7 mL) and heated at 70° C. for 1.5 hours. Upon completion of the reaction, the resulting reaction mixture was cooled to room temperature and filtered by passing through a celite pad. The filtrate was concentrated under reduced pressure. The resulting residue was purified by silica gel chromatography (1-6% ethyl acetate in dichloromethane) to give the target compound (57 mg, 0.178 mmol, 93% yield).

$^1$H NMR (400 MHz, CDCl$_3$): 7.77 (d, J=5.2 Hz, 1H), 7.65 (d, J=2.8 Hz, 1H), 7.05 (t, J=8.8 Hz, 1H), 6.79 (dd, J=2.8 Hz, 0.4 Hz, 1H), 6.56-6.46 (m, 2H), 5.66 (dd, J=5.2 Hz, 1.2 Hz, 1H), 3.81 (br s, 2H).

(Step 11) N-(4-(5-bromopyrrolo[1,2-b]pyridazin-4-yloxy)-3-fluorophenyl)-1,5-dimethyl-3-oxo-2-phenyl-2,3-dihydro-1H-pyrazole-4-carboxamide

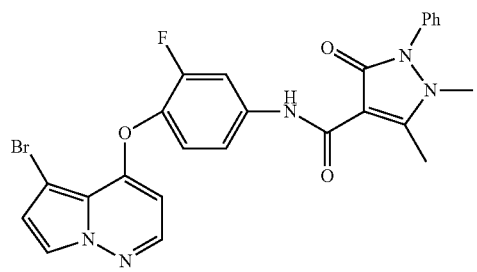 [SMILES: Cc1c(C(=O)Nc2ccc(Oc3ccnn4ccc(-c5ccccc5)c34)c(F)c2)c(=O)n(-c2ccccc2)n1C]

To a solution of 4-(5-bromopyrrolo[1,2-b]pyridazin-4-yloxy)-3-fluoroaniline (57 mg, 0.178 mmol) and 1,5-dimethyl-3-oxo-2-phenyl-2,3-dihydro-1H-pyrazole-4-carboxylic acid (124 mg, 0.534 mmol) prepared in Preparation Example 1 in dimethylformamide (2 mL), HATU (270 mg, 0.711 mmol) and triethylamine (0.1 mL, 0.711 mmol) were sequentially added and stirred at 50° C. overnight. The resulting reaction mixture was concentrated under reduced pressure and the resulting residue was extracted with dichloromethane and water. The organic layer was separated, dried with magnesium sulfate, and then filtered. The filtrate was concentrated under reduced pressure. The resulting residue was purified by silica gel chromatography (10% ethyl acetate in dichloromethane) to give the target compound as a white solid (60 mg, 0.111 mmol, 63% yield).

MS (ESI pos. ion) m/z: 536, 538 (MH$^+$). Calc'd exact mass for C$_{25}$H$_{19}$Br$_{79}$FN$_5$O$_3$: 535, Calc'd exact mass for C$_{25}$H$_{19}$Br$_{81}$FN$_5$O$_3$: 537.

$^1$H NMR (400 MHz, CDCl$_3$): 10.89 (br s, 1H), 7.91 (dd, J=12.4 Hz, 2.4 Hz, 1H), 7.78 (d, J=5.6 Hz, 1H), 7.65 (d, J=2.8 Hz, 1H), 7.59-7.54 (m, 2H), 7.52-7.46 (m, 1H), 7.38-7.35 (m, 2H), 7.31-7.28 (m, 1H), 7.19 (t, J=8.8 Hz, 1H), 6.80 (d, J=2.8 Hz, 1H), 5.67 (dd, J=5.6 Hz, 1.2 Hz, 1H), 3.38 (s, 3H), 2.80 (s, 3H).

Example 2

N-(3-Fluoro-4-(5-phenylpyrrolo[1,2-b]pyridazin-4-yloxo)phenyl)-1,5-dimethyl-3-oxo-2-phenyl-2,3-dihydro-1H-pyrazole-4-carboxamide

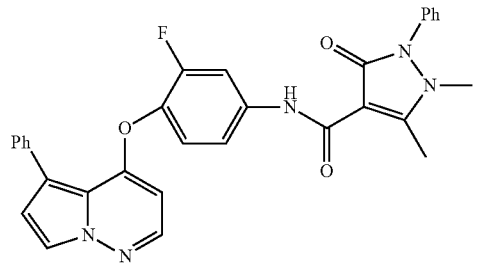

To a solution of N-(4-(5-bromopyrrolo[1,2-b]pyridazin-4-yloxy)-3-fluorophenyl)-1,5-dimethyl-3-oxo-2-phenyl-2,3- dihydro-1H-pyrazole-4-carboxamide (50 mg, 0.093 mmol) prepared in Example 1 and phenylboronic acid (45 mg, 0.373 mmol) dissolved in dioxane (0.8 mL), 1 M potassium carbonate aqueous solution (0.4 mL, 0.373 mmol) and Pd(PPh$_3$)$_4$ (11 mg, 0.009 mmol) were sequentially added. The resulting reaction mixture was stirred at 80° C. for 2 hours. The resulting mixture was extracted with dichloromethane and water. The organic layer was separated, dried with magnesium sulfate, and then filtered. The filtrate was concentrated under reduced pressure. The resulting residue was purified by silica gel chromatography (10% ethyl acetate in dichloromethane) to give the target compound as a yellow solid (36 mg, 0.067 mmol, 72% yield).

MS (ESI pos. ion) m/z: 534 (MH$^+$). Calc'd exact mass for C$_{31}$H$_{24}$FN$_5$O$_3$: 533.

$^1$H NMR (400 MHz, CDCl$_3$): 10.84 (br s, 1H), 7.87 (dd, J=12.8 Hz, 2.4 Hz, 1H), 8.83-7.79 (m, 2H), 7.66-7.44 (m, 5H), 7.37-7.32 (m, 4H), 7.24-7.20 (m, 2H), 7.07 (t, J=8.8 Hz, 1H), 6.88 (d, J=2.8 Hz, 1H), 5.68 (d, J=5.2 Hz, 1H), 3.37 (s, 3H), 2.79 (s, 3H).

Example 3

N-(3-Fluoro-4-(5-(4-fluorophenyl)pyrrolo[1,2-b]pyridazin-4-yloxy)phenyl)-1,5-dimethyl-3-oxo-2-phenyl-2,3-dihydro-1H-pyrazole-4-carboxamide

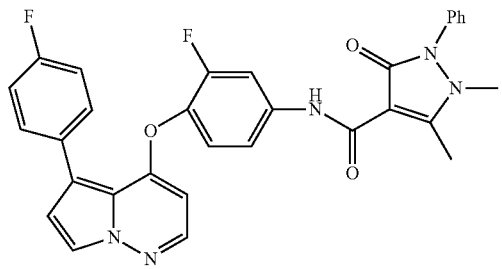 [SMILES: Cc1c(C(=O)Nc2ccc(Oc3ccnn4ccc(-c5ccc(F)cc5)c34)c(F)c2)c(=O)n(-c2ccccc2)n1C]

The target compound N-(3-fluoro-4-(5-(4-fluorophenyl)pyrrolo[1,2-b]pyridazin-4-yloxy)phenyl)-1,5-dimethyl-3-oxo-2-phenyl-2,3-dihydro-1H-pyrazole-4-carboxamide was prepared in the same manner as Example 2, except for using 4-fluorophenylboronic acid (0.373 mmol) instead of phenyl boronic acid.

MS (ESI pos. ion) m/z: 552 Calc'd exact mass for C$_{31}$H$_{23}$F$_2$N$_5$O$_3$: 551.

$^1$H NMR (400 MHz, CDCl$_3$): 10.85 (br s, 1H), 7.88 (dd, J=12.4 Hz, 2.4 Hz, 1H), 7.81 (dd, J=5.2 Hz, 0.4 Hz, 1H), 7.79 (d, J=2.8 Hz, 1H), 7.61-7.52 (m, 4H), 7.50-7.45 (m, 1H), 7.37-7.35 (m, 2H), 7.25-7.21 (m, 1H), 7.08-7.00 (m, 3H), 6.84 (dd, J=2.4 Hz, 0.4 Hz, 1H), 5.68 (dd, J=5.2 Hz, 1.2 Hz, 1H), 3.71 (s, 3H), 2.79 (s, 3H).

Example 4

N-(3-Fluoro-4-(5-(4-methoxyphenyl)pyrrolo[1,2-b]pyridazin-4-yloxy)phenyl)-1,5-dimethyl-3-oxo-2-phenyl-2,3-dihydro-1H-pyrazole-4-carboxamide

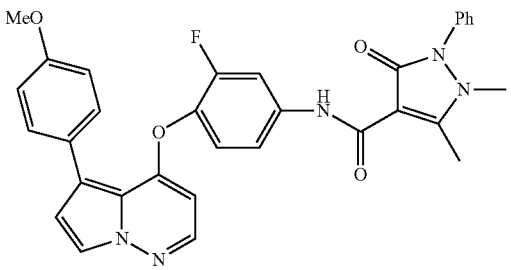 [SMILES: COc1ccc(-c2ccn3nccc(Oc4ccc(NC(=O)c5c(C)n(C)n(-c6ccccc6)c5=O)cc4F)c23)cc1]

The target compound N-(3-fluoro-4-(5-(4-methoxyphenyl)pyrrolo[1,2-b]pyridazin-4-yloxy)phenyl)-1,5-dimethyl-3-oxo-2-phenyl-2,3-dihydro-1H-pyrazole-4-carboxamide was prepared in the same manner as Example 2, except for using 4-methoxyphenylboronic acid (0.373 mmol) instead of phenylboronic acid.

MS (ESI pos. ion) m/z: 564 (MH$^+$). Calc'd exact mass for C$_{32}$H$_{26}$FN$_5$O$_4$: 563.

$^1$H NMR (400 MHz, CDCl$_3$): 10.84 (br s, 1H), 7.87 (dd, J=12.4 Hz, 2.8 Hz, 1H), 7.79 (d, J=5.2 Hz, 1H), 7.77 (d, J=2.8 Hz, 1H), 7.59-7.53 (m, 4H), 7.50-7.44 (m, 1H), 7.38-7.34 (m, 2H), 7.26-7.21 (m, 1H), 7.07 (t, J=8.8 Hz, 1H), 6.91-6.88 (m, 2H), 6.83 (d, J=2.4 Hz, 1H), 5.65 (dd, J=5.2 Hz, 1.2 Hz, 1H), 3.81 (s, 3H), 3.37 (s, 3H), 2.79 (s, 3H).

Example 5

N-(3-Fluoro-4-(5-(3-fluorophenyl)pyrrolo[1,2-b]pyridazin-4-yloxo) phenyl)-1,5-dimethyl-3-oxo-2-phenyl-2,3-dihydro-1H-pyrazole-4-carboxamide

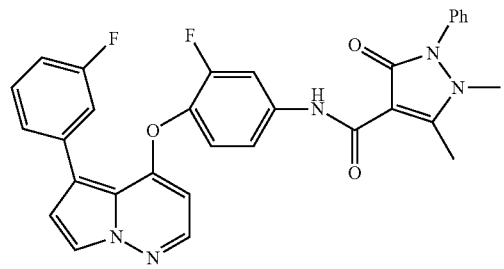 [SMILES: Cc1c(C(=O)Nc2ccc(Oc3ccnn4ccc(-c5cccc(F)c5)c34)c(F)c2)c(=O)n(-c2ccccc2)n1C]

The target compound N-(3-fluoro-4-(5-(4-fluorophenyl)pyrrolo[1,2-b]pyridazin-4-yloxy)phenyl)-1,5-dimethyl-3-oxo-2-phenyl-2,3-dihydro-1H-pyrazole-4-carboxamide was prepared in the same manner as Example 2, except for using 3-fluorophenylboronic acid (0.373 mmol) instead of phenylboronic acid.

MS (ESI pos. ion) m/z: 552 (MH$^+$) Calc'd exact mass for C$_{31}$H$_{23}$F$_2$N$_5$O$_3$: 551.

$^1$H NMR (400 MHz, CDCl$_3$): 10.85 (br s, 1H), 7.88 (dd, J=12.4 Hz, 2.4 Hz, 1H), 7.84 (d, J=5.6 Hz, 1H), 7.80 (d, J=2.8 Hz, 1H), 7.59-7.54 (m, 2H), 7.50-7.46 (m, 1H), 7.43-7.40 (m,

1H), 7.37-7.22 (m, 5H), 7.08 (t, J=8.8 Hz, 1H), 6.94-6.87 (m, 1H), 6.88 (d, J=3.2 Hz, 1H), 5.72 (dd, J=5.6 Hz, 1.2 Hz, 1H), 3.37 (s, 3H), 2.79 (s, 3H).

Example 6

N-(3-Fluoro-4-(5-(3-methoxyphenyl)pyrrolo[1,2-b]pyridazin-4-yloxy)phenyl)-1,5-dimethyl-3-oxo-2-phenyl-2,3-dihydro-1H-pyrazole-4-carboxamide

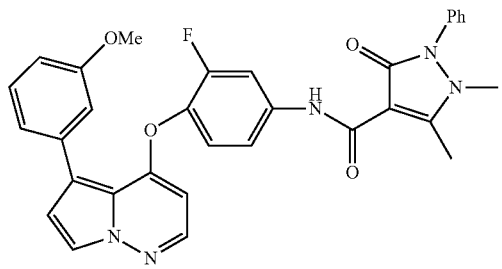 [SMILES: COc1cccc(-c2ccn3nccc(Oc4ccc(NC(=O)c5c(C)n(C)n(-c6ccccc6)c5=O)cc4F)c23)c1]

The target compound N-(3-fluoro-4-(5-(4-methoxyphenyl)pyrrolo[1,2-b]pyridazin-4-yloxy)phenyl)-1,5-dimethyl-3-oxo-2-phenyl-2,3-dihydro-1H-pyrazole-4-carboxamide was prepared in the same manner as Example 2, except for using 3-methoxyphenylboronic acid (0.373 mmol) instead of phenylboronic acid.

MS (ESI pos. ion) m/z: 564 (MH$^+$). Calc'd exact mass for $C_{32}H_{26}FN_5O_4$ 563.

$^1$H NMR (400 MHz, CDCl$_3$): 10.85 (br s, 1H), 7.89 (dd, J=12.4 Hz, 2.4 Hz, 1H), 7.82 (d, J=5.6 Hz, 1H), 7.79 (d, J=2.8 Hz, 1H), 7.58-7.54 (m, 2H), 7.50-7.47 (m, 1H), 7.37-7.34 (m, 2H), 7.26-7.21 (m, 4H), 7.07 (t, J=8.8 Hz, 1H), 6.90 (d, J=2.8 Hz, 1H), 6.81-6.78 (m, 1H), 5.68 (dd, J=5.2 Hz, 1.2 Hz, 1H), 3.78 (s, 3H), 3.72 (s, 3H), 2.79 (s, 3H).

Example 7

N-(4-(5-Bromopyrrolo[1,2-b]pyridazin-4-yloxy)-3-fluorophenyl)-2-(4-fluorophenyl)-1,5-dimethyl-3-oxo-2,3-dihydro-1H-pyrazole-4-carboxamide

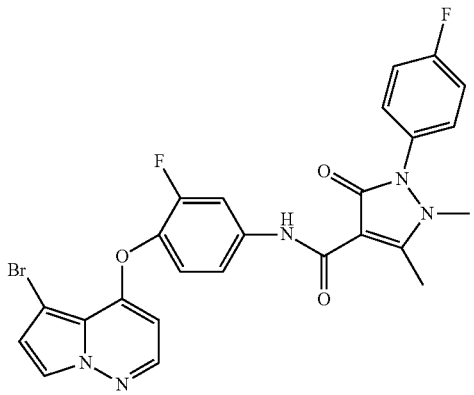

The target compound N-(4-(5-bromopyrrolo[1,2-b]pyridazin-4-yloxy)-3-fluorophenyl)-2-(4-fluorophenyl)-1,5-dimethyl-3-oxo-2,3-dihydro-1H-pyrazole-4-carboxamide was prepared in the same manner as Example 1, except for using 2-(4-fluorophenyl)-1,5-dimethyl-3-oxo-2,3-dihydro-1H-pyrazole-4-carboxylic acid prepared in Preparation Example 2 instead of 1,5-dimethyl-3-oxo-2-phenyl-2,3-dihydro-1H-pyrazole-4-carboxylic in Step 11 of Example 1.

MS (ESI pos. ion) m/z: 554 (MH$^+$). Calc'd exact mass for $C_{25}H_{18}BrF_2N_5O_3$: 553.

$^1$H NMR (400 MHz, CDCl$_3$): 10.81 (br s, 1H), 7.91 (dd, J=12.4 Hz, 2.4 Hz, 1H), 7.78 (d, J=5.2 Hz, 1H), 7.65 (d, J=3.2 Hz, 1H), 7.37-7.33 (m, 2H), 7.31-7.17 (m, 4H), 6.80 (d, J=3.2 Hz, 1H), 5.67 (dd, J=5.2 Hz, 1.2 Hz, 1H), 3.36 (s, 3H), 2.80 (s, 3H).

Example 8

N-(3-Fluoro-4-(5-phenylpyrrolo[1,2-b]pyridazin-4-yloxy)phenyl)-2-(4-fluorophenyl)-1,5-dimethyl-3-oxo-2,3-dihydro-1H-pyrazole-4-carboxamide

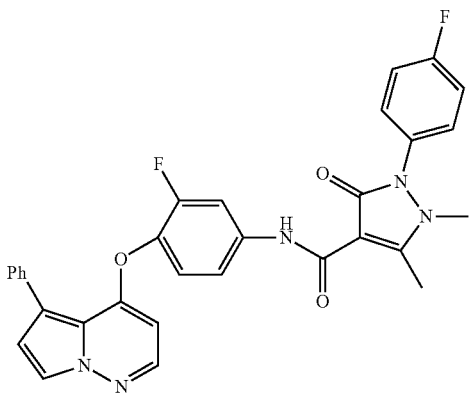 [SMILES: Cc1c(C(=O)Nc2ccc(Oc3ccnn4ccc(-c5ccccc5)c34)c(F)c2)c(=O)n(-c2ccc(F)cc2)n1C]

The target compound N-(3-fluoro-4-(5-phenylpyrrolo[1,2-b]pyridazin-4-yloxy)phenyl)-2-(4-fluorophenyl)-1,5-dimethyl-3-oxo-2,3-dihydro-1H-pyrazole-4-carboxamide was prepared in the same manner as Example 2.

MS (ESI pos. ion) m/z: 552 (MH$^+$). Calc'd exact mass for $C_{31}H_{23}F_2N_5O_3$: 551.

$^1$H NMR (400 MHz, CDCl$_3$): 10.77 (br s, 1H), 7.86 (dd, J=12.4 Hz, 2.4 Hz, 1H), 8.83-7.79 (m, 2H), 7.75-7.72 (m, 1H), 7.66-7.63 (m, 2H), 7.43-7.32 (m, 5H), 7.28-7.20 (m, 2H), 7.06 (t, J=8.8 Hz, 1H), 6.89 (d, J=2.8 Hz, 1H), 5.68 (dd, J=5.2 Hz, 0.8 Hz, 1H), 3.35 (s, 3H), 2.79 (s, 3H).

Example 9

1,5-Dimethyl-3-oxo-2-phenyl-2,3-dihydro-1H-pyrazole-4-carboxylic acid [3-fluoro-4-(pyrrolo[1,2-b]pyridazin-4-yloxy)-phenyl]-amide

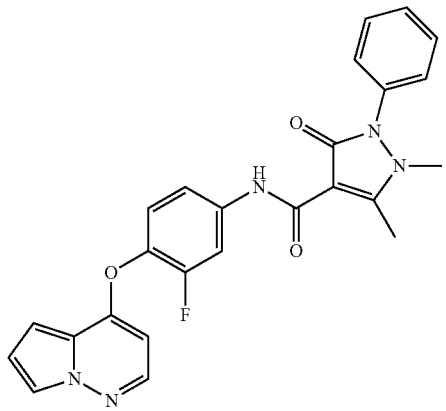 [SMILES: Cc1c(C(=O)Nc2ccc(Oc3ccnn4cccc34)c(F)c2)c(=O)n(-c2ccccc2)n1C]

To a solution of 3-fluoro-4-(pyrrolo[1,2-b]pyridazin-4-yloxy)-phenylamine (50 mg, 0.206 mmol) and 1,5-dimethyl- 3-oxo-2-phenyl-2,3-dihydro-1H-pyrazole-4-carboxylic acid (32 mg, 0.137 mmol) dissolved in dimethylformamide (3 mL), HATU (78 mg, 0.206 mmol) and triethylamine (0.05 mL, 0.343 mmol) were sequentially added and heated at 50° C. for 7 hours. The resulting mixture was concentrated and the resulting residue was extracted with dichloromethane and water. After phase separation, the organic layer was washed with sodium chloride aqueous solution, dried with magnesium sulfate, and then filtered. The filtrate was concentrated under reduced pressure. The resulting residue was purified by silica gel chromatography (ethyl acetate:hexane=1:3) to give the target compound as a white solid (16 mg, 0.04 mmol, 25% yield).

$^1$H NMR (400 MHz, CDCl$_3$): 10.88 (br S, 1H) 7.90 (dd, J=12.8 Hz, 2.4 Hz, 1H), 7.83 (d, J=5.6 Hz, 1H), 7.74 (dd, J=2.4 Hz, 1.6 Hz, 1H), 7.59-7.36 (m, 5H), 7.29 (m, J=8.8 Hz, 2.4 Hz, 1.2 Hz, 1H), 7.17 (t, J=8.8 Hz, 1H), 6.81 (dd, J=4.4 Hz, 2.4 Hz, 1H), 5.69 (d, J=5.2 Hz, 1H), 3.38 (s, 3H), 2.80 (s, 3H). MS (ESI pos. ion) m/z: 458 (MH$^+$), Calc'd exact mass for C$_{25}$H$_{20}$FN$_5$O$_3$: 457.16.

Example 10

1,5-Dimethyl-3-oxo-2-phenyl-2,3-dihydro-1H-pyrazole-4-carboxylic acid

[3-fluoro-4-(2-phenyl-1H-pyrrolo[2,3-b]pyridin-4-yloxy)-phenyl]-amide

The target compound was prepared as follows:

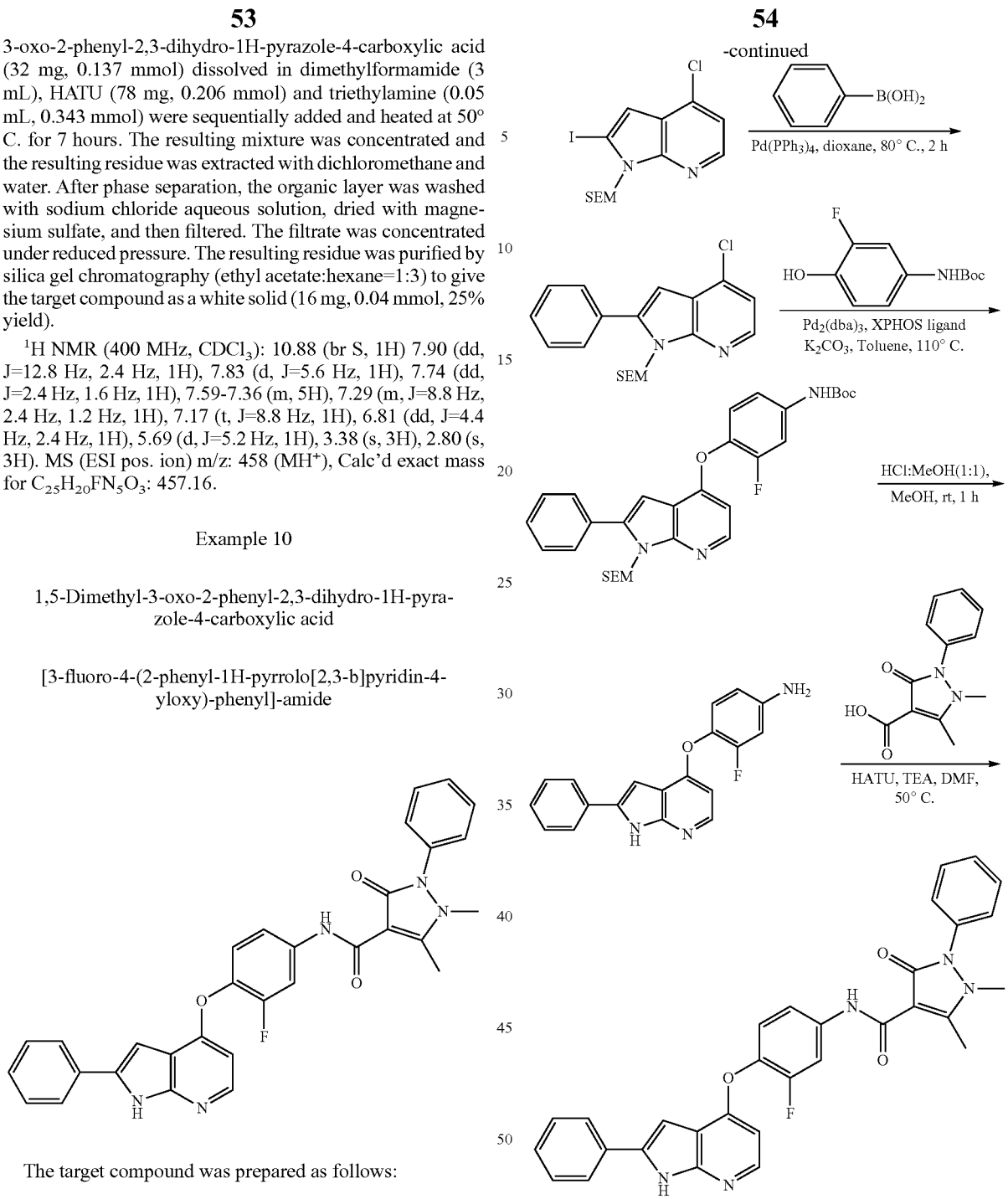

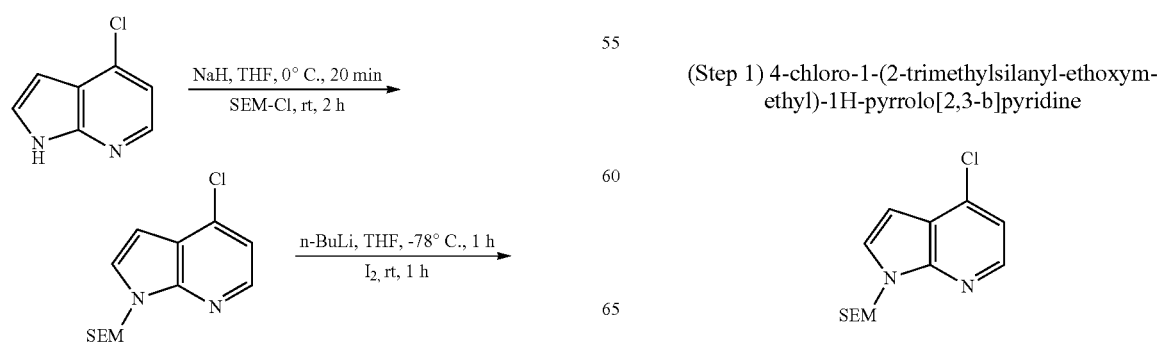

(Step 1) 4-chloro-1-(2-trimethylsilanyl-ethoxymethyl)-1H-pyrrolo[2,3-b]pyridine

4-Chloro-1H-pyrrolo[2,3-b]pyridine (170 mg, 1.114 mmol) was dissolved in tetrahydrofuran (2 mL) under nitrogen atmosphere. After cooling to 0° C., 40% NaH (30 mg, 1.224 mmol) was added. The resulting reaction mixture was stirred for 15 minutes and then heated at 80° C. for 3 hours after adding SEM-Cl (185 mg, 1.114 mmol). The heated reaction mixture was cooled to room temperature and then extracted with dichloromethane and water. The organic layer was separated and washed with sodium chloride aqueous solution. The organic layer was dried with magnesium sulfate and then filtered. The filtrate was concentrated under reduced pressure. The resulting residue was purified by silica gel chromatography (ethyl acetate:hexane=1:1) to give the target compound as a yellow oil (235 mg, 0.83 mmol, 74% yield).

$^1$H NMR (400 MHz, CDCl$_3$): 8.22 (d, J=5.2 Hz, 1H), 7.38 (d, J=3.6 Hz, 1H), 7.12 (d, J=5.2 Hz, 1H), 6.6 (d, J=3.6 Hz, 1H), 5.67 (s, 2H), 3.53 (t, J=8 Hz, 2H), 0.90 (t, J=8 Hz, 2H), −0.07 (s, 9H).

(Step 2) 4-chloro-2-iodo-1-(2-trimethylsilanyl-ethoxymethyl)-1H-pyrrolo[2,3-b]pyridine

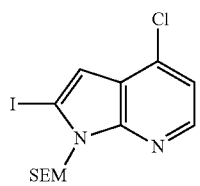 [SMILES: C[Si](C)(C)CCOCn1c(I)cc2c(Cl)ccnc21]

4-Chloro-1-(2-trimethylsilanyl-ethoxymethyl)-1H-pyrrolo[2,3-b]pyridine (235 mg, 0.831 mmol) was dissolved in tetrahydrofuran (3 mL) under nitrogen atmosphere. After cooling to −78° C., n-butyllithium (0.675 mL, 1.080 mmol, 1.6 M hexane solution) was slowly added dropwise. The resulting mixture was stirred for 1 hour. After adding a solution of iodine (253 mg, 0.997 mmol) in tetrahydrofuran (2 mL), the mixture was slowly heated to room temperature. One hour later, the mixture was extracted with dichloromethane and water and the organic layer was washed with sodium chloride aqueous solution. The organic layer was dried with magnesium sulfate and then filtered. The filtrate was concentrated under reduced pressure. The resulting residue was purified by silica gel chromatography (hexane:ethyl acetate=9:1) to give the target compound as a yellow oil (339 mg, 0.83 mmol, 97% yield).

(Step 3) 4-chloro-2-phenyl-1-(2-trimethylsilanyl-ethoxymethyl)-1H-pyrrolo[2,3-b]pyridine

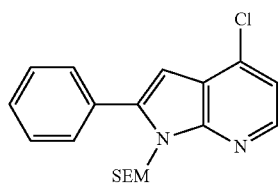 [SMILES: C[Si](C)(C)CCOCn1c(-c2ccccc2)cc2c(Cl)ccnc21]

4-Chloro-2-iodo-1-(2-trimethylsilanyl-ethoxymethyl)-1H-pyrrolo[2,3-b]pyridine (329 mg, 0.805 mmol) and phenylboronic acid (118 mg, 0.966 mmol) were dissolved in dioxane and then Pd(PPh$_3$)$_4$ (46 mg, 0.04 mmol) was added. After adding 1 M potassium carbonate aqueous solution (1.61 mL), the resulting reaction mixture was stirred at 80° C. for 2 hours. The reaction mixture was extracted with dichloromethane and water. The organic layer was washed with sodium chloride aqueous solution, dried with magnesium sulfate, and then filtered. The filtrate was concentrated under reduced pressure. The resulting residue was purified by silica gel chromatography (hexane:ethyl acetate=9:1) to give the target compound as a yellow oil (182 mg, 0.51 mmol, 63% yield).

$^1$H NMR (400 MHz, CDCl$_3$): 8.22 (d, J=4.8 Hz, 1H), 7.80-7.43 (m, 5H), 7.14 (d, J=4.8 Hz, 1H), 6.69 (s, 1H), 5.66 (s, 2H), 3.72 (t, J=8.4 Hz, 2H), 0.95 (t, J=8.4 Hz, 2H), 0.04 (s, 9H).

(Step 4) 3-fluoro-4-[2-phenyl-1-(2-trimethylsilanyl-ethoxymethyl)-1H-pyrrolo[2,3-b]pyridin-4-yloxy]-phenyl-carbamic acid t-butyl ester

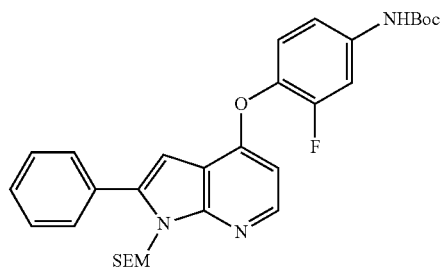 [SMILES: CC(C)(C)OC(=O)Nc1ccc(Oc2ccnc3c2cc(-c2ccccc2)n3COCC[Si](C)(C)C)c(F)c1]

4-Chloro-2-phenyl-1-(2-trimethylsilanyl-ethoxymethyl)-1H-pyrrolo[2,3-b]pyridine (312 mg, 0.87 mmol) and (3-fluoro-4-hydroxy-phenyl)-carbamic acid t-butyl ester (336 mg, 1.48 mmol) were dissolved in anhydrous toluene (5 mL) under nitrogen atmosphere. After adding dicyclohexyl-phosphino-2,4,6-triisopropylbiphenyl (41 mg, 0.087 mmol), Pd$_2$dba$_3$ (40 mg, 0.044 mmol) and potassium carbonate, the mixture was heated at 110° C. The resulting reaction mixture was cooled to room temperature and filtered by passing through a celite pad. The filtrate was concentrated under reduced pressure. The resulting residue was purified by silica gel chromatography (hexane: ethyl acetate=9:1) to give the target compound as a white solid (404 mg, 0.73 mmol, 84% yield).

$^1$H NMR (400 MHz, CDCl$_3$): 8.16 (d, J=5.6 Hz, 1H), 7.77-7.741 (m, 6H), 7.16 (t, J=8.8 Hz, 1H), 7.04-7.01 (m, 1H), 6.57 (s, 1H), 6.53 (br s, 1H), 6.43 (dd, J=4.8 Hz, 1H), 5.66 (s, 2H), 3.73 (t, J=8.4 Hz, 2H), 1.54 (s, 9H), 0.96 (t, J=8.4 Hz, 2H), −0.04 (s, 9H).

(Step 5) 3-fluoro-4-(2-phenyl-1H-pyrrolo[2,3-b]pyridin-4-yloxy)-phenylamine

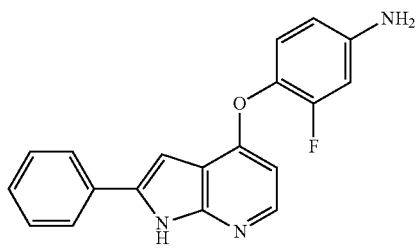 [SMILES: Nc1ccc(Oc2ccnc3[nH]c(-c4ccccc4)cc23)c(F)c1]

To a solution of 3-fluoro-4-[2-phenyl-1-(2-trimethylsilanyl-ethoxymethyl)-1H-pyrrolo[2,3-b]pyridin-4-yloxy]-phenyl-carbamic acid t-butyl ester in methanol, a 1:1 solution (10 mL) of hydrochloric acid and methanol was added. The mixture was stirred at room temperature for 4 hours. The resulting reaction mixture was concentrated under reduced pressure and ether was added to the resulting residue. After stirring for 2 hours, the produced solid was collected by filtering. Thus obtained hydrochloride was dissolved in water and neutralized to about pH 8 by adding 1 M sodium hydroxide aqueous solution. The resulting mixture was extracted with ethyl acetate. The organic layer was separated and washed with sodium chloride aqueous solution. The organic layer was dried with $Na_2SO_4$ and then filtered. The filtrate was concentrated under reduced pressure. The resulting residue was purified by silica gel chromatography (hexane:ethyl acetate=1:1) to give the target compound as a white solid (81 mg, 0.25 mmol, 40% yield).

$^1$H NMR (400 MHz, DMSO): 12.21 (br s, 1H), 8.04 (d, J=5.6 Hz, 1H), 7.93-7.32 (m, 5H), 7.05 (t, J=8.8 Hz, 1H), 6.85 (d, J=2.0 Hz, 1H), 6.54 (dd, J=13.2 Hz, 2.4 Hz, 1H), 6.45 (m, J=10 Hz, 1.6 Hz, 0.8 Hz, 1H), 6.25 (m, 1H), 5.45 (s, 2H).

(Step 6) 1,5-dimethyl-3-oxo-2-phenyl-2,3-dihydro-1H-pyrazole-4-carboxylic acid

[3-fluoro-4-(2-phenyl-1H-pyrrolo[2,3-b]pyridin-4-yloxy)-phenyl]-amide

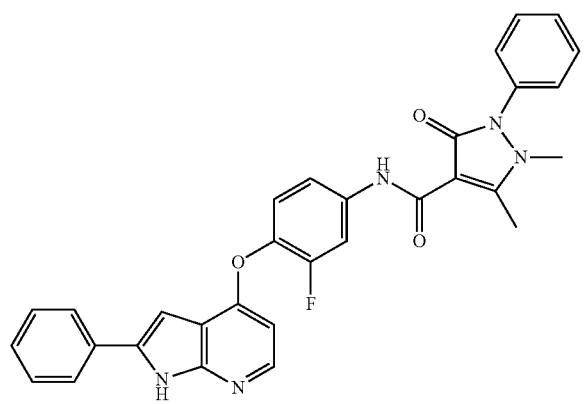 [SMILES: Cc1c(C(=O)Nc2ccc(Oc3ccnc4[nH]c(-c5ccccc5)cc34)c(F)c2)c(=O)n(-c2ccccc2)n1C]

3-Fluoro-4-(2-phenyl-1H-pyrrolo[2,3-b]pyridin-4-yloxy)-phenylamine (80 mg, 0.25 mmol), 1,5-dimethyl-3-oxo-2-phenyl-2,3-dihydro-1H-pyrazole-4-carboxylic acid (72 mg, 0.31 mmol) and HATU (190 mg, 0.5 mmol) were dissolved in dimethylformamide (3 mL). After adding triethylamine (0.04 mL, 0.5 mmol), the mixture was heated at 50° C. for 7 hours. The resulting reaction mixture was extracted with dichloromethane and water. The organic layer was washed with sodium chloride aqueous solution, dried with magnesium sulfate, and then filtered. The filtrate was concentrated under reduced pressure. The resulting residue was purified by silica gel chromatography (hexane:ethyl acetate=1:1) to give the target compound as a white solid (12 mg, 0.02 mmol, 9% yield).

$^1$H NMR (400 MHz, DMSO): 12.29 (br s, 1H), 10.95 (br s, 1H), 8.08 (d, J=5.6 Hz, 1H), 7.98 (d, J=2.4, 1H), 7.94 (m, 2H), 7.60 (m, 2H), 7.52 (m, 1H), 7.46 (m, 4H), 7.33 (m, 3H), 6.89 (d, J=2.0 Hz, 1H), 6.35 (d, J=5.6, 1H), 3.38 (s, 3H), 2.71 (s, 3H). MS (ESI pos. ion) m/z: 534, Calc'd exact mass for $C_{31}H_{24}FN_5O_3$: 533.55.

Example 11

2-(4-Fluoro-phenyl)-1,5-dimethyl-3-oxo-2,3-dihydro-1H-pyrazole-4-carboxylic acid

[3-fluoro-4-(2-phenyl-1H-pyrrolo[2,3-b]pyridin-4-yloxy)-phenyl]-amide

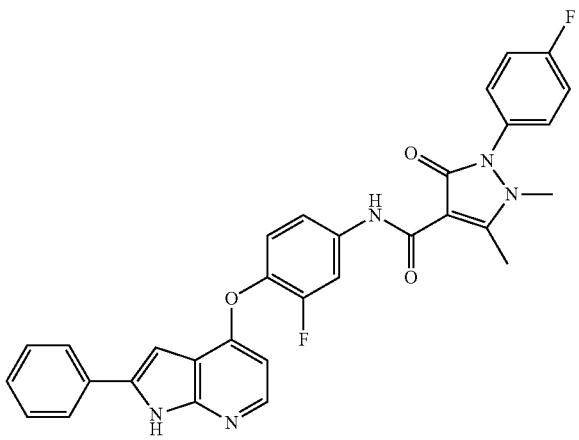 [SMILES: Cc1c(C(=O)Nc2ccc(Oc3ccnc4[nH]c(-c5ccccc5)cc34)c(F)c2)c(=O)n(-c2ccc(F)cc2)n1C]

The target compound was prepared in the same manner as Example 10, except for using 1,5-dimethyl-3-oxo-2-3-fluorophenyl-2,3-dihydro-1H-pyrazole-4-carboxylic acid (0.31 mmol) instead of 1,5-dimethyl-3-oxo-2-phenyl-2,3-dihydro-1H-pyrazole-4-carboxylic acid (0.31 mmol) in Step 6 of Example 10.

MS (ESI pos. ion) m/z: 552 (MH$^+$). Calc'd exact mass for $C_{31}H_{23}F_2N_5O_3$: 551.

$^1$H NMR (400 MHz, DMSO): 10.90 (s, 1H), 8.16 (d, J=5.6 Hz, 1H), 7.93 (dd, J=13.2 Hz, 2.4 Hz, 1H), 7.71 (s, 1H), 7.68-7.65 (m, 2H), 7.53-7.49 (m, 2H), 7.46-7.42 (m, 2H), 7.38-7.32 (m, 3H), 7.29-7.27 (m, 1H), 7.25-7.21 (m, 1H), 6.37 (d, J=5.6 Hz, 1H), 5.67 (s, 1H), 3.36 (s, 3H), 2.69 (s, 3H).

Example 12

2-(4-Fluoro-phenyl)-1,5-dimethyl-3-oxo-2,3-dihydro-1H-pyrazole-4-carboxylic acid

[3-fluoro-4-(3-phenyl-1H-pyrrolo[2,3-b]pyridin-4-yloxy)-phenyl]-amide

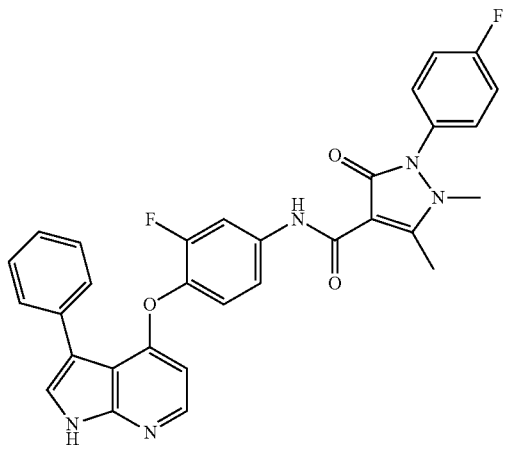 [SMILES: Cc1c(C(=O)Nc2ccc(Oc3ccnc4[nH]cc(-c5ccccc5)c34)c(F)c2)c(=O)n(-c2ccc(F)cc2)n1C]

The target compound was prepared in the same manner as Example 10.

MS (ESI pos. ion) m/z: 552 (MH+), Calc'd exact mass for $C_{31}H_{23}F_2N_5O_3$: 551.

$^1$H NMR (400 MHz, DMSO): 12.29 (br s, 1H), 10.92 (br s, 1H), 8.08 (d, J=5.6 Hz, 1H), 7.98 (d, J=2.4 Hz, 1H), 7.94-7.92 (m, 2H), 7.54-7.30 (m, 9H), 6.89 (s, 1H), 6.35 (d, J=5.6 Hz, 1H), 3.37 (s, 3H), 2.70 (s, 3H).

Example 13

N-(3-Fluoro-4-(pyrrolo[1,2-f][1,2,4]triazin-4-yloxy)phenyl)-2-(4-fluorophenyl)-1,5-dimethyl-3-oxo-2,3-dihydro-1H-pyrazole-4-carboxamide The target compound was prepared as follows:

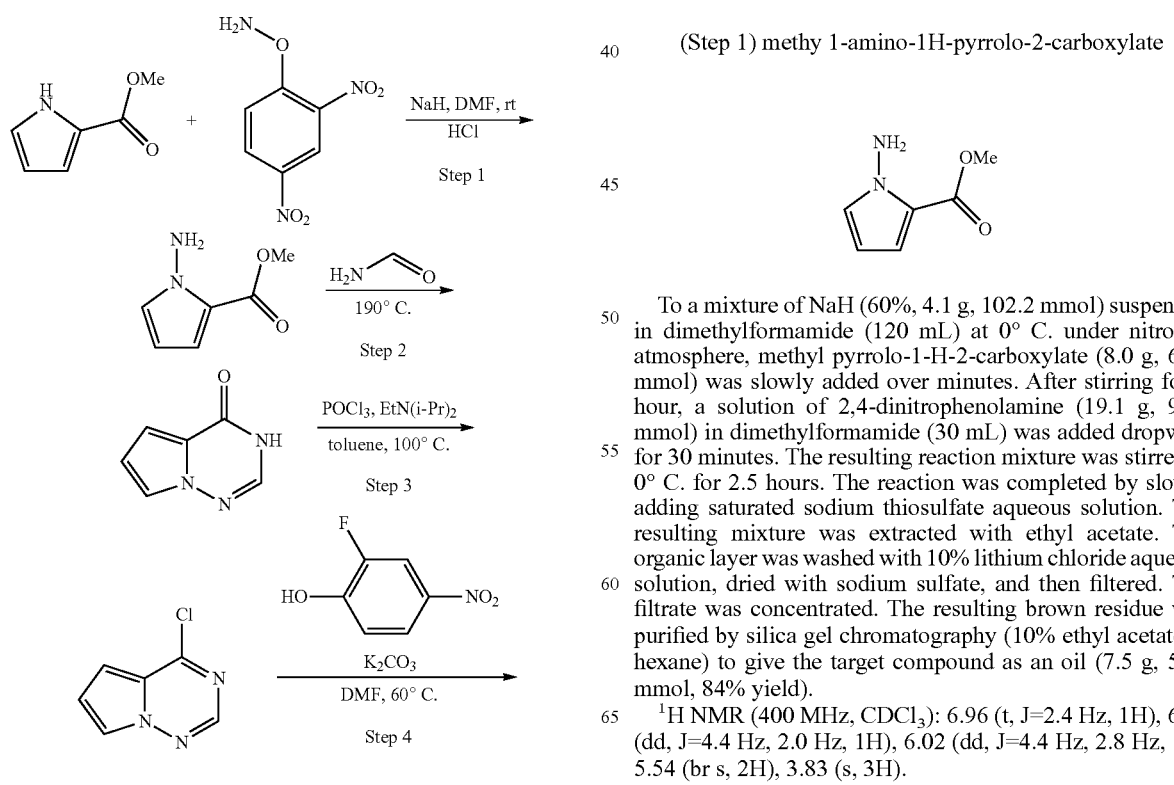

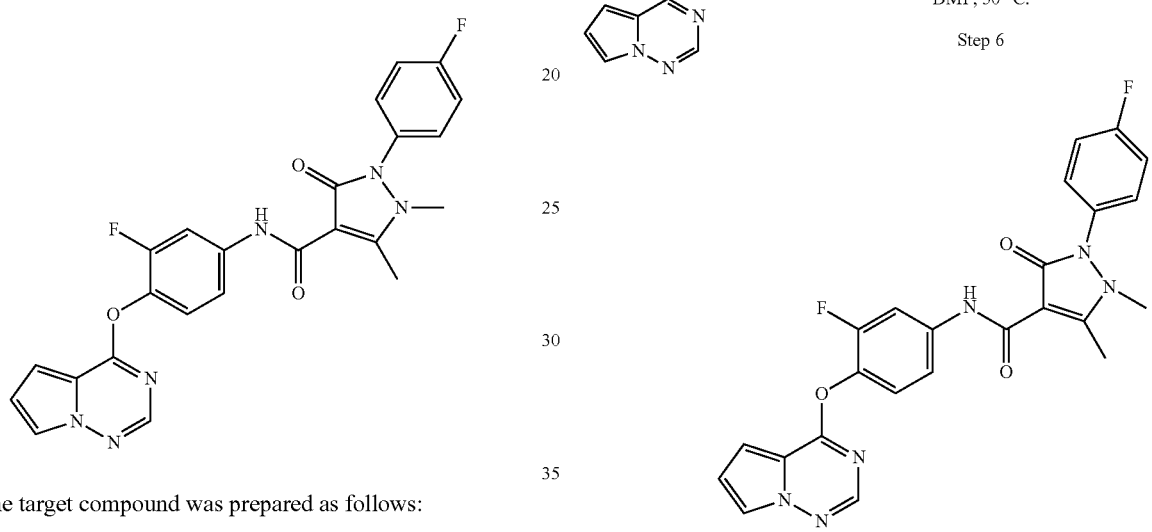

(Step 1) methy 1-amino-1H-pyrrolo-2-carboxylate

To a mixture of NaH (60%, 4.1 g, 102.2 mmol) suspended in dimethylformamide (120 mL) at 0° C. under nitrogen atmosphere, methyl pyrrolo-1-H-2-carboxylate (8.0 g, 63.9 mmol) was slowly added over minutes. After stirring for 1 hour, a solution of 2,4-dinitrophenolamine (19.1 g, 95.9 mmol) in dimethylformamide (30 mL) was added dropwise for 30 minutes. The resulting reaction mixture was stirred at 0° C. for 2.5 hours. The reaction was completed by slowly adding saturated sodium thiosulfate aqueous solution. The resulting mixture was extracted with ethyl acetate. The organic layer was washed with 10% lithium chloride aqueous solution, dried with sodium sulfate, and then filtered. The filtrate was concentrated. The resulting brown residue was purified by silica gel chromatography (10% ethyl acetate in hexane) to give the target compound as an oil (7.5 g, 53.5 mmol, 84% yield).

$^1$H NMR (400 MHz, CDCl$_3$): 6.96 (t, J=2.4 Hz, 1H), 6.83 (dd, J=4.4 Hz, 2.0 Hz, 1H), 6.02 (dd, J=4.4 Hz, 2.8 Hz, 1H) 5.54 (br s, 2H), 3.83 (s, 3H).

(Step 2) pyrrolo[1,2-f]1,2,4]triazin-4(3H)-one

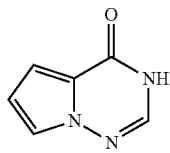

Methyl 1H-pyrrole-2-carboxylate (7.5 g, 53.5 mmol) was dissolved in formamide (30 mL). After heating at 170° C. for 1 hour, the mixture was further heated at 190° C. for 2 hours. The resulting reaction mixture was cooled to room temperature. The produced solid was recrystallized with ethyl acetate to give the target compound as a white solid (5.0 g, 37.0 mmol, 69% yield).

$^1$H NMR (400 MHz, CDCl$_3$): 7.57 (s, 1H), 7.47 (dd, J=2.8 Hz, 1.6 Hz, 1H), 7.10 (dd, J=4.4 Hz, 1.6 Hz, 1H), 7.47 (dd, J=4.4 Hz, 2.8 Hz, 1H).

(Step 3) 4-chloropyrrolo[1,2-f][1,2,4]triazine

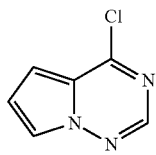

Diisopropylethylamine (3.5 mL, 20.3 mmol) was added to a solution of pyrrolo[1,2-f][1,2,4]triazin-4(3H)-one (2.5 g, 18.5 mmol) dissolved in toluene (37.5 mL) under nitrogen atmosphere. Subsequently, after adding phosphorus oxychloride (5.1 mL, 55.7 mmol), the mixture was heated for 20 hours at 100° C. The resulting reaction mixture was cooled to 0° C. and, after slowly adding sodium bicarbonate aqueous solution, stirred at room temperature for 30 minutes. The resulting aqueous layer was extracted with ethyl acetate, dried with magnesium sulfate, and then filtered. The filtrate was concentrated in vacuum. The resulting yellow solid product was subjected to the next step without purification (2.31 g, 15.0 mmol, 81% yield).

$^1$H NMR (400 MHz, CDCl$_3$): 8.22 (s, 1H), 7.87 (dd, J=2.4 Hz, 1.6 Hz, 1H), 7.00-6.97 (m, 2H).

(Step 4) 4-(2-fluoro-4-nitrophenoxy)pyrrolo[1,2-f][1,2,4]triazine

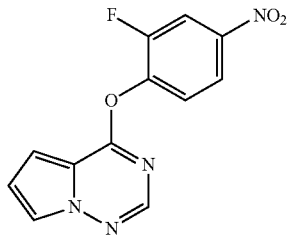

A solution of 4-chloropyrrolo[1,2-f][1,2,4]triazine (4.30 g, 28.0 mmol), 2-fluoro-4-nitrophenol (5.28 g, 33.6 mmol) and potassium carbonate (7.74 g, 56.0 mmol) added to anhydrous N-dimethylformamide (60 mL) under nitrogen atmosphere was heated at 60° C. for 1 hour and 20 minutes. The resulting mixture was allowed to cool to room temperature and then extracted with ethyl acetate. The resulting extract was concentrated and purified by silica gel chromatography (25% ethyl acetate in n-hexane) to give the target compound as a white solid (5.50 g, 20.0 mmol, 72% yield).

$^1$H NMR (400 MHz, CDCl$_3$): 8.21-8.14 (m, 2H), 7.97 (s, 1H), 7.86 (dd, J=2.8 Hz, 1.2 Hz, 1H) 7.54 (t, J=8.0 Hz, 1H), 7.07 (dd, J=4.4 Hz, 1.2 Hz, 1H), 6.93 (dd, J=4.4 Hz, 2.8 Hz, 1H).

(Step 5) 3-fluoro-4-(pyrrolo[1,2-f][1,2,4]triazin-4-yloxy)aniline

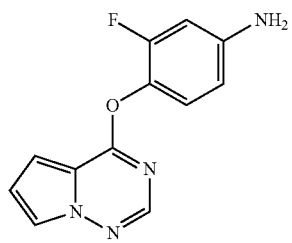 [SMILES: Nc1ccc(Oc2ncnn3cccc23)c(F)c1]

4-(2-Fluoro-4-nitrophenoxy)pyrrolo[1,2-f][1,2,4]triazine (50 mg, 0.18 mmol), zinc powder (280 mg, 4.37 mmol) and ammonium chloride (130 mg, 2.37 mmol) were added to tetrahydrofuran (3.3 mL) and methanol (0.8 mL) and stirred for 1.5 hours at 70° C. under reflux. The resulting mixture was allowed to cool to room temperature and filtered with celite. Purification by silica gel chromatography (1-6% ethyl acetate in dichloromethane) yielded the target compound as an ivory solid (44 mg, 0.18 mmol, 99% yield).

$^1$H NMR (400 MHz, CDCl$_3$): 7.92 (s, 1H), 7.70 (dd, J=2.5 Hz, 1.6 Hz, 1H) 6.98 (t, J=8.5 Hz, 1H), 6.92 (dd, J=4.4 Hz, 1.4 Hz, 1H), 6.77 (m, 1H), 6.42 (m, 2H), 3.71 (br s, 2H).

(Step 6) N-(3-fluoro-4-(pyrrolo[1,2-f][1,2,4]triazin-4-yloxy)phenyl)-2-(4-fluorophenyl)-1,5-dimethyl-3-oxo-2,3-dihydro-1H-pyrazole-4-carboxamide

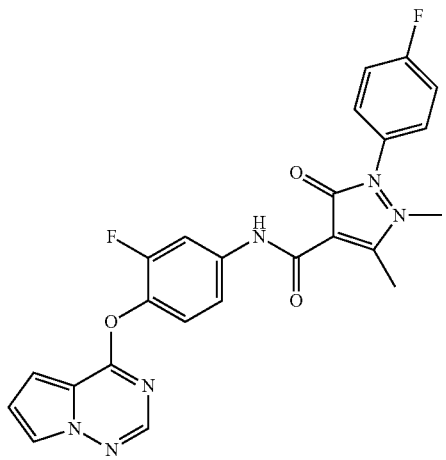

To a solution of 3-fluoro-4-(pyrrolo[1,2-f][1,2,4]triazin-4-yloxy)aniline (44 mg, 0.18 mmol) and 2-(4-fluorophenyl)-1, 5-dimethyl-3-oxo-2,3-dihydro-1H-pyrazole-4-carboxylic acid (90 mg, 0.36 mmol) in dimethylformamide (1.7 mL), HATU (200 mg, 0.54 mmol) and triethylamine (0.08 mL, 0.55 mmol) were sequentially added and stirred at 50° C. overnight. The resulting reaction mixture was concentrated under reduced pressure and the resulting residue was extracted with ethyl acetate and water. The organic layer was separated from the reaction mixture, dried with magnesium sulfate, and then filtered. The filtrate was concentrated under reduced pressure. The resulting residue was purified by silica gel chromatography (10% ethyl acetate in dichloromethane) to give the target compound as a white solid (85 mg, 0.18 mmol, 99% yield).

MS (ESI pos. ion) m/z: 477 (MH$^+$). Calc'd exact mass for $C_{24}H_{18}F_2N_6O_3$: 476. $^1$H NMR (400 MHz, CDCl$_3$): 10.79 (br s, 1H), 7.98 (s, 1H), 7.90 (dd, J=4.0 Hz, 1.6 Hz, 1H), 7.78 (dd, J=1.6 Hz, 0.8 Hz, 1H), 7.37-7.34 (m, 2H), 7.31-7.24 (m, 3H), 7.20 (t, J=5.6 Hz, 1H), 7.00 (dd, J=2.8 Hz, 0.4 Hz, 1H), 6.85 (dd, J=2.8 Hz, 2.0 Hz, 1H), 3.35 (s, 3H), 2.79 (s, 3H).

Example 14

N-(3-Fluoro-4-(pyrrolo[1,2-f][1,2,4]triazin-4-yloxy)phenyl)-1,5-dimethyl-3-oxy-2-phenyl-2,3-dihydro-1H-pyrazole-4-carboxamide

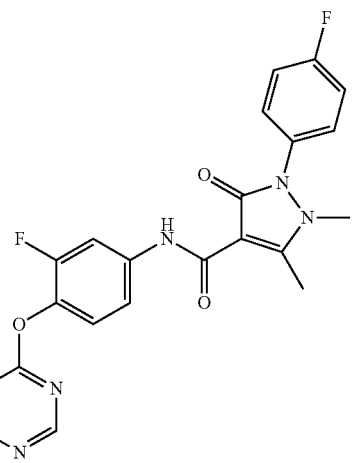

The target compound N-(3-fluoro-4-(pyrrolo[1,2-f][1,2,4]triazin-4-yloxy)phenyl)-1,5-dimethyl-3-oxy-2-phenyl-2,3-dihydro-1H-pyrazole-4-carboxamide was prepared in the same manner as Example 13.

MS (ESI neg. ion) m/z: 457 (MH$^-$). Calc'd exact mass for $C_{24}H_{19}FN_6O_3$: 458.

$^1$H NMR (400 MHz, CDCl$_3$): 10.87 (br s, 1H), 7.99 (s, 1H), 7.92 (dd, J=12.0 Hz, 1.8 Hz, 1H), 7.78 (dd, J=2.4 Hz, 1.2 Hz, 1H), 7.58-7.55 (m, 2H), 7.49-7.46 (m, 1H), 7.37-7.36 (m, 2H), 7.32-7.30 (m, 1H), 7.20 (t, J=8.4 Hz, 1H), 7.00 (dd, J=4.2 Hz, 1.2 Hz, 1H), 6.85 (dd, J=4.2 Hz, 2.4 Hz, 1H), 3.37 (s, 3H), 2.80 (s, 3H).

Example 15

N-(3-fluoro-4-(6-phenylpyrrolo[1,2-f][1,2,4]triazin-4-yloxy)phenyl)-2-(4-fluorophenyl)-1,5-dimethyl-3-oxo-2,3-dihydro-1H-pyrazole-4-carboxamide

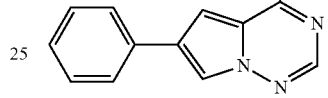

The target compound was prepared as follows:

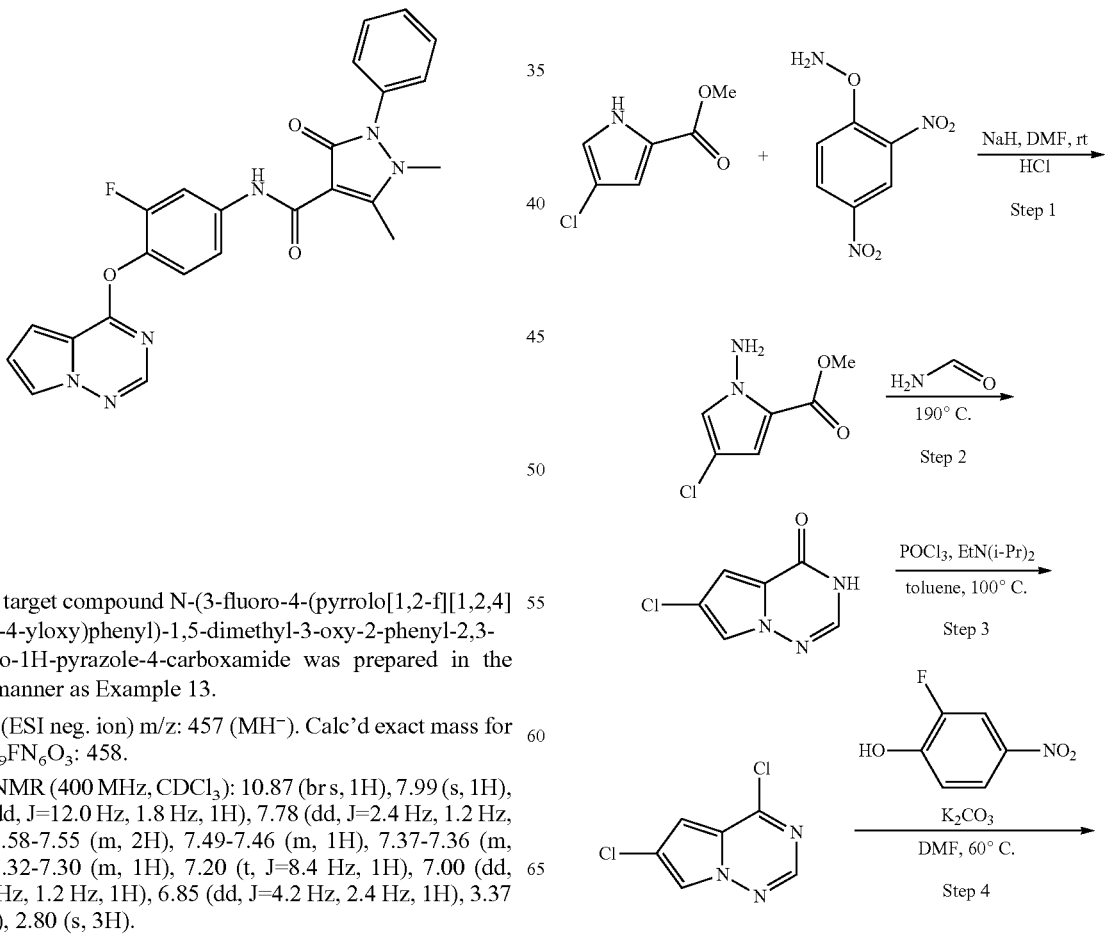

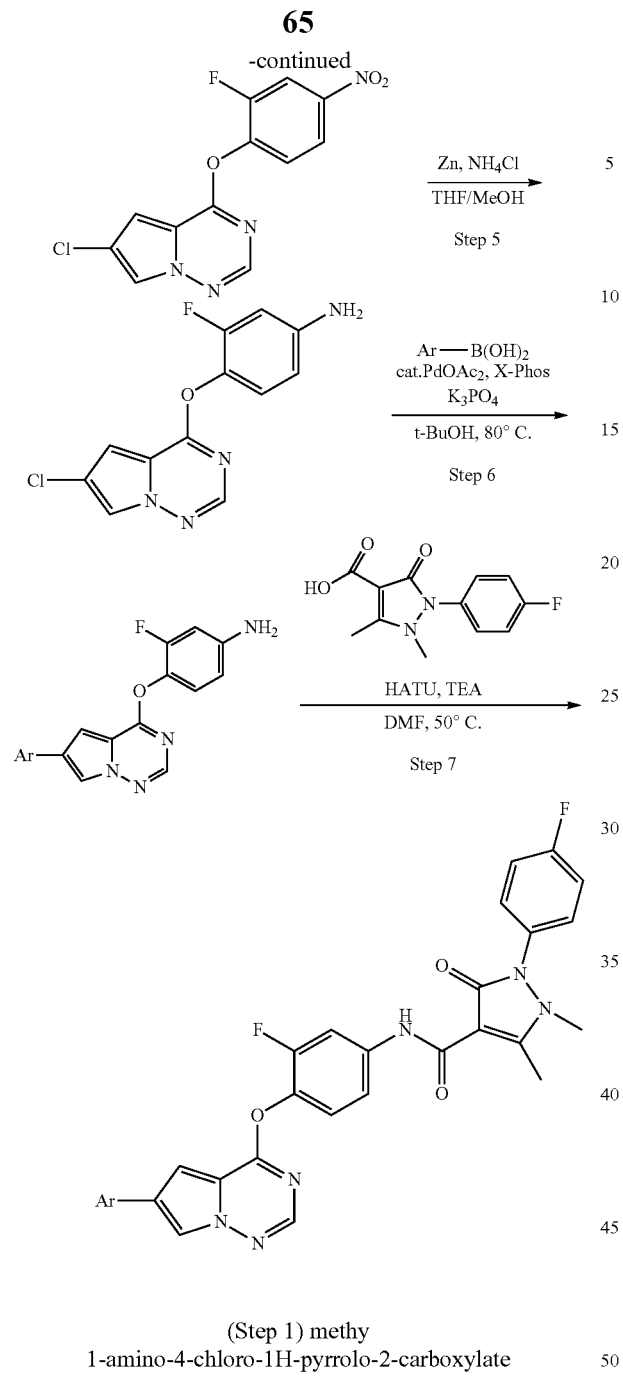

(Step 1) methy 1-amino-4-chloro-1H-pyrrolo-2-carboxylate

Methyl 4-chloro-1-H-pyrrole-2-carboxylate (1.0 g, 6.27 mmol) was slowly added over 30 minutes to a mixture of NaH (60%, 0.4 g, 10.03 mmol) suspended in dimethylformamide (12 mL) at 0° C. under nitrogen atmosphere. After stirring at 0° C. for 1 hour, a solution of 予 2,4-dinitrophenolamine (1.87 g, 9.40 mmol) in dimethylformamide (6 mL) was added dropwise for 30 minutes. The resulting reaction mixture was stirred at 0° C. for 2.5 hours and the reaction was terminated by slowly adding saturated sodium thiosulfate aqueous solution. The resulting mixture was extracted with ethyl acetate. The organic layer was washed with 10% lithium chloride aqueous solution, dried with sodium sulfate, and then filtered. The filtrate was concentrated. The resulting brown residue was purified by silica gel chromatography (10% ethyl acetate in hexane) to give the target compound as an oil (930 mg, 5.33 mmol, 85% yield).

$^1$H NMR (400 MHz, CDCl$_3$): 6.91 (d, J=2.4 Hz, 1H), 6.73 (d, J=2.4 Hz, 1H), 5.54 (br s, 2H), 3.83 (s, 3H).

(Step 2) 6-chloropyrrolo[1,2-f][1,2,4]triazin-4(3H)-one

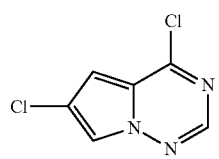 [SMILES: Clc1cc2c(Cl)ncnn2c1]

Methy 1-amino-4-chloro-1H-pyrrolo-2-carboxylate (900 mg, 5.15 mmol) was dissolved in formamide (3.6 mL) and heated at 170° C. for 1 hour and then at 190° C. for 2 hours. The resulting reaction mixture was cooled to room temperature. The produced solid was recrystallized with ethyl acetate to give the target compound as a white solid (500 mg, 2.95 mmol, 57% yield).

$^1$H NMR (400 MHz, CDCl$_3$): 7.54 (s, 1H), 7.41 (d, J=1.6 Hz, 1H), 7.01 (d, J=1.6 Hz, 1H).

(Step 3) 4,6-dichloropyrrolo[1,2-f][1,2,4]triazine

Diisopropylethylamine (0.56 mL, 3.25 mmol) was added to a solution of 6-chloropyrrolo[1,2-f][1,2,4]triazin-4(3H)-one (500 mg, 2.95 mmol) dissolved in toluene (7.5 mL) under nitrogen atmosphere. Subsequently, after adding phosphorus oxychloride (0.8 mL, 8.87 mmol), the mixture was heated for 20 hours at 100° C. The resulting reaction mixture was cooled to 0° C. After slowly adding sodium bicarbonate aqueous solution, the mixture was stirred at room temperature for 30 minutes. The resulting aqueous layer was extracted with ethyl acetate, dried with magnesium sulfate, and then filtered. The filtrate was concentrated in vacuum. The resulting yellow solid product was subjected to the next step without purification (510 mg, 2.71 mmol, 92% yield).

¹H NMR (400 MHz, CDCl₃): 8.25 (s, 1H), 7.84 (d, J=1.6 Hz, 1H), 6.94 (d, J=1.6 Hz, 1H).

(Step 4) 6-chloro-4-(2-fluoro-4-nitrophenoxy)pyrrolo[1,2-f][1,2,4]triazine

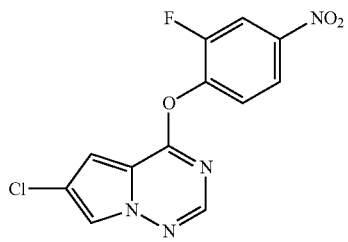 [SMILES: O=[N+]([O-])c1ccc(Oc2ncnn3cc(Cl)cc23)c(F)c1]

4,6-Dimethylpyrrolo[1,2-f][1,2,4]triazine (150 mg, 0.798 mmol), 2-fluoro-4-nitrophenol (150 mg, 0.957 mmol) and potassium carbonate (220 mg, 1.59 mmol) were added to anhydrous N-dimethylformamide (3.6 mL). The resulting solution was heated at 60° C. for 1 hour and 20 minutes under nitrogen atmosphere. The resulting mixture was allowed to cool to room temperature and then extracted with ethyl acetate. The extract was concentrated and purified by silica gel chromatography (25% ethyl acetate in n-hexane) to give the target compound as a white solid. (203 mg, 0.658 mmol, 83% yield)

¹H NMR (600 MHz, CDCl₃): 8.20-8.15 (m, 2H), 7.98 (s, 1H), 7.82 (d, J=1.8 Hz, 1H), 7.54-7.51 (m, 1H), 7.00 (d, J=1.8 Hz, 1H).

(Step 5) 4-(6-chloropyrrolo[1,2-f][1,2,4]triazin-4-yloxy)-3-fluoroaniline

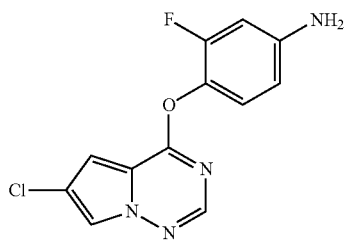 [SMILES: Nc1ccc(Oc2ncnn3cc(Cl)cc23)c(F)c1]

6-Chloro-4-(2-fluoro-4-nitrophenoxy)pyrrolo[1,2-f][1,2,4]triazine (0.2 g, 0.648 mmol), zinc powder (1.02 g, 15.6 mmol) and ammonium chloride (0.45 g, 8.42 mmol) were added to tetrahydrofuran (13.3 mL) and methanol (3.3 mL) and stirred for 1 hour and 10 minutes at 70° C. under reflux. The resulting mixture was allowed to cool to room temperature, filtered with celite, concentrated and then purified by silica gel chromatography to give the target compound as an ivory solid (153 mg, 0.549 mmol, 85% yield).

¹H NMR (600 MHz, CDCl₃): 8.01 (s, 1H), 7.73 (d, J=1.8 Hz, 1H), 7.03 (t, J=2.4 Hz, 1H), 6.93 (d, J=1.8 Hz, 1H), 6.54-6.47 (m, 2H), 3.80 (br s, 2H).

(Step 6) 3-fluoro-4-(6-phenylpyrrolo[1,2,-f][1,2,4]triazin-4-yloxy)aniline

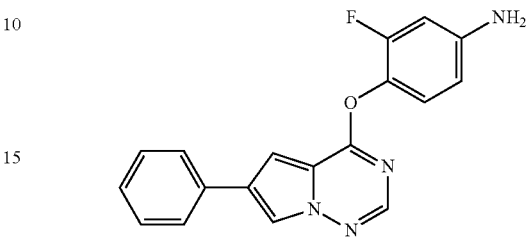

t-Butanol (0.5 mL) was added under nitrogen atmosphere to a flask containing palladium acetate (4 mg, 0.018 mmol), X-Phos ligand (21 mg, 0.045 mmol), 4-(6-chloropyrrolo[1,2-f][1,2,4]triazin-4-yloxy)-3-fluoroaniline (50 mg, 0.018 mmol), phenylboronic acid (44 mg, 0.036 mmol) and potassium phosphate (65 mg, 0.054 mmol). After stirring, the resulting mixture was heated at 80° C. for 10 hours. Upon completion of the reaction, the resulting reaction mixture was cooled to room temperature and filtered through celite while washing with dichloromethane. The filtrate was concentrated and extracted with ethyl acetate and water. The organic layer was dried with magnesium sulfate and then filtered. The filtrate was concentrated under reduced pressure. The resulting residue was purified by silica gel chromatography (n-hexane:ethyl acetate=5:1) to give the target compound as a pale yellow solid (32 mg, 0.1 mmol, 56% yield).

MS (ESI pos. ion) m/z: 321 (MH⁺). Calc'd exact mass for C₁₈H₁₃FN₄O: 320.11.

¹H NMR (600 MHz, CDCl₃): 8.06 (s, 1H), 8.00 (s, 3H), 7.68 (d, J=8.4 Hz, 2H), 7.44 (t, J=7.2 Hz, 2H), 7.32 (t, J=7.2 Hz, 1H), 7.25 (s, 1H), 7.07 (t, J=8.4 Hz, 1H), 6.56-6.49 (m, 2H), 3.80 (s, 2H).

(Step 7) N-(3-fluoro-4-(6-phenylpyrrolo[1,2-f][1,2,4]triazin-4-yloxy)phenyl)-2-(4-fluorophenyl)-1,5-dimethyl-3-oxo-2,3-dihydro-1H-pyrazole-4-carboxamide

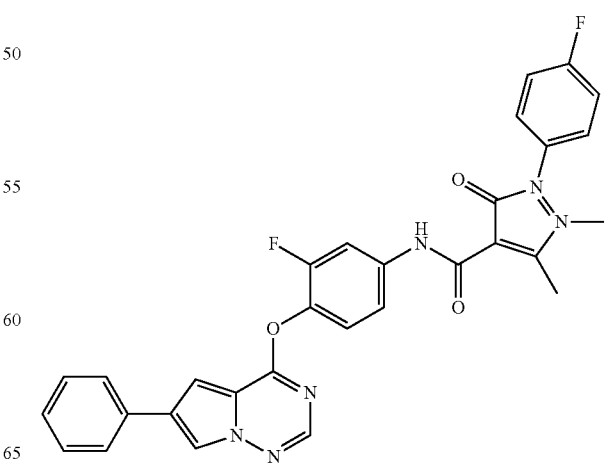

To a solution of 3-fluoro-4-(6-phenylpyrrolo[1,2-f][1,2,4]triazin-4-yloxy)aniline (27 mg, 0.084 mmol) and 2-(4-fluorophenyl)-1,5-dimethyl-3-oxo-2,3-dihydro-1H-pyrazole-4-carboxylic acid (42 mg, 0.017 mmol) in dimethylformamide (0.5 mL), HATU (96 mg, 0.25 mmol) and triethylamine (0.035 mL, 0.25 mmol) were sequentially added and then stirred at 50° C. overnight. The resulting reaction mixture was concentrated under reduced pressure and the produced residue was extracted with ethyl acetate and water. The organic layer was separated, dried with magnesium sulfate, and then filtered. The filtrate was concentrated under reduced pressure. The resulting residue was purified by silica gel chromatography (50% ethyl acetate in n-hexane) to give the target compound as a white solid (38 mg, 0.069 mmol, 83% yield).

MS (ESI pos. ion) m/z: 553 (MH$^+$). Calc'd exact mass for $C_{30}H_{22}F_2N_6O_3$: 552.17.

$^1$H NMR (400 MHz, CDCl$_3$): 10.80 (br s, 1H), 8.07 (d, J=1.6 Hz, 1H), 7.99 (s, 1H), 7.92 (dd, J=12.4, 2.4 Hz, 1H), 7.69 (d, J=7.6, 2H), 7.44 (t, J=7.6, 2H), 7.38-7.23 (m, 8H), 3.56 (s, 3H), 2.80 (s, 3H).

Example 16

N-(4-(6-Chloropyrrolo[1,2-f][1,2,4]triazin-4-yloxy)-3-fluorophenyl)-2-(4-fluorophenyl)-1,5-dimethyl-3-oxo-2,3-dihydro-1H-pyrazole-4-carboxamide

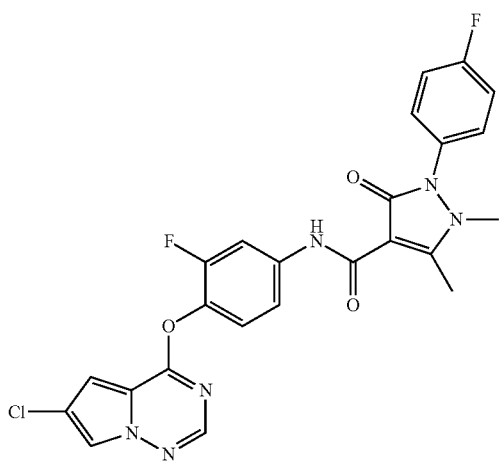 [SMILES: Cc1c(C(=O)Nc2ccc(Oc3ncnn4cc(Cl)cc34)c(F)c2)c(=O)n(-c2ccc(F)cc2)n1C]

The target compound N-(4-(6-chloropyrrolo[1,2-f][1,2,4]triazin-4-yloxy)-3-fluorophenyl)-1,5-dimethyl-3-oxo-2-phenyl-2,3-dihydro-1H-pyrazole-4-carboxamide was prepared in the same manner as Example 15.

MS (ESI pos. ion) m/z: 511 (MH$^+$). Calc'd exact mass for $C_{24}H_{17}ClF_2N_6O_3$: 510.10.

$^1$H NMR (400 MHz, CDCl$_3$ in DMSO-d$_6$ 2 drops): 10.84 (br s, 1H), 8.00 (s, 1H), 7.91 (m, 1H), 7.75 (s, 1H), 7.39-7.17 (m, 6H), 6.94 (s, 1H), 3.37 (s, 3H), 2.80 (s, 3H).

Example 17

N-(4-(6-Chloropyrrolo[1,2-f][1,2,4]triazin-4-yloxy)-3-fluorophenyl)-1,5-dimethyl-3-oxo-2-phenyl-2,3-dihydro-1H-pyrazole-4-carboxamide

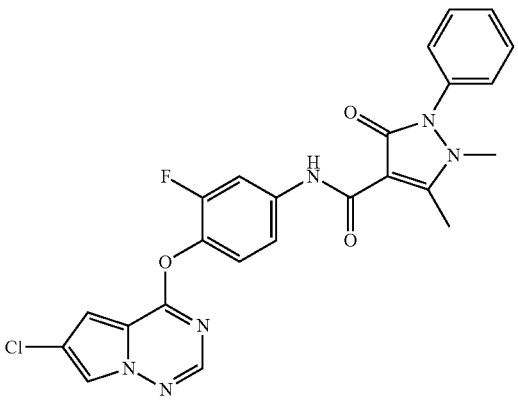 [SMILES: Cc1c(C(=O)Nc2ccc(Oc3ncnn4cc(Cl)cc34)c(F)c2)c(=O)n(-c2ccccc2)n1C]

The target compound N-(4-(6-chloropyrrolo[1,2-f][1,2,4]triazin-4-yloxy)-3-fluorophenyl)-1,5-dimethyl-3-oxo-2-phenyl-2,3-dihydro-1H-pyrazole-4-carboxamide was prepared in the same manner as Example 15.

MS (ESI pos. ion) m/z: 493 (MH$^+$). Calc'd exact mass for $C_{24}H_{18}ClFN_6O_3$: 492.11.

$^1$H NMR (400 MHz, CDCl$_3$): 10.88 (br s, 1H), 7.92 (dd, J=12.2, 2.2 Hz, 1H), 7.74 (d, J=1.6 Hz, 1H), 7.58-7.29 (m, 6H), 7.18 (t, J=8.6 Hz, 1H), 6.95 (d, J=1.6 Hz, 1H), 3.37 (s, 3H), 2.80 (s, 3H).

Example 18

N-(3-Fluoro-4-(6-phenylpyrrolo[1,2-f][1,2,4]triazin-4-yloxy)phenyl)-1,5-dimethyl-3-oxo-2-phenyl-2,3-dihydro-1H-pyrazole-4-carboxamide

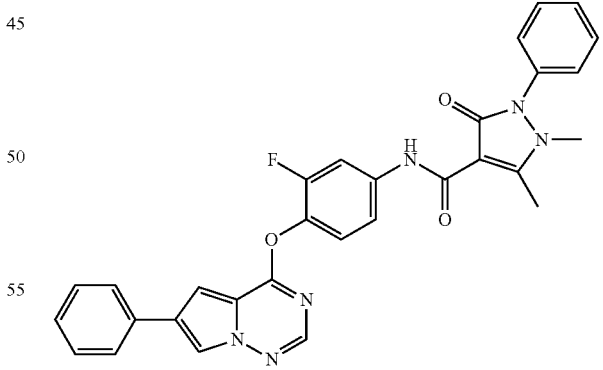

The target compound N-(3-fluoro-4-(6-phenylpyrrolo[1,2-f][1,2,4]triazin-4-yloxy)phenyl)-1,5-dimethyl-3-oxo-2-phenyl-2,3-dihydro-1H-pyrazole-4-carboxamide was prepared in the same manner as Example 15.

MS (ESI pos. ion) m/z: 535 (MH$^+$). Calc'd exact mass for $C_{30}H_{23}FN_6O_3$: 534.18.

$^1$H NMR (400 MHz, CDCl$_3$): 10.88 (br s, 1H), 8.07 (d, J=1.6 Hz, 1H), 8.00 (s, 1H), 7.92 (dd, J=12.2, 2.2 Hz, 1H), 7.69 (d, J=7.2, 2H), 7.57 (t, J=7.6, 2H), 7.50-7.42 (m, 3H), 7.38-7.20 (m, 5H), 3.37 (s, 3H), 2.80 (s, 3H).

Example 19

N-(3-Fluoro-4-(5-phenylpyrrolo[1,2-b]pyridazin-4-yloxy)phenyl)-1,2-dimethyl-3-oxo-5-phenyl-2,3-dihydro-1H-pyrazole-4-carboxamide

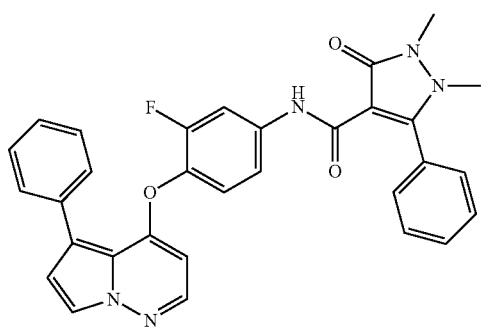 [SMILES: Cn1c(-c2ccccc2)c(C(=O)Nc2ccc(Oc3ccnn4ccc(-c5ccccc5)c34)c(F)c2)c(=O)n1C]

The target compound was prepared as follows:

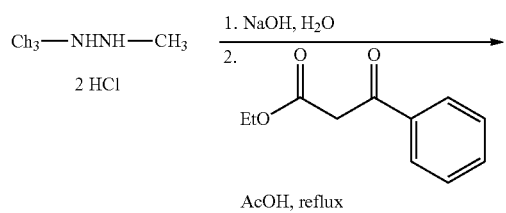

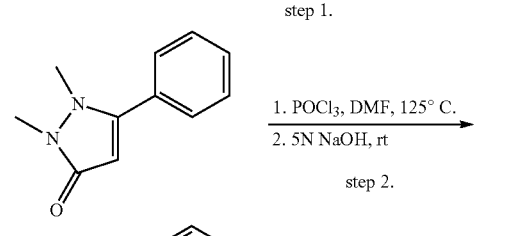 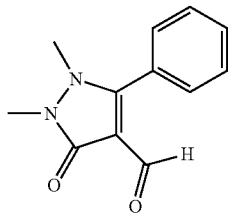 [SMILES: Cn1c(-c2ccccc2)c(C=O)c(=O)n1C]

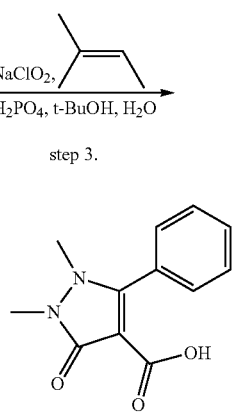

(Step 1) 1,2-dimethyl-5-phenyl-1H-pyrazol-3(2H)-one

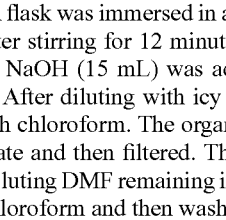

1,2-Dimethylhydrazine 2-dihydrochloride (2.77 g, 20.8 mmol) was added to an aqueous solution of sodium hydroxide (1.66 g, 41.6 mmol) in water (32 mL). After stirring for 10 minutes, ethyl benzoylacetate (2.0 g, 10.4 mmol) and glacial acetic acid (0.89 mL, 15.6 mmol) were added and the mixture was stirred at 115° C. overnight under reflux. The resulting reaction mixture was cooled to room temperature and extracted with ethyl acetate, 10:1 dichloromethane/methanol, and then with ethyl acetate. The organic layer was collected, dried with sodium sulfate, and then filtered. The filtrate was concentrated. The resulting residue was separated by silica gel chromatography (DCM: MeOH=95:5) to give the target compound (420 mg, 2.23 mmol, 21% yield).

MS (ESI pos. ion) m/z: 189 (MH$^+$). Calc'd exact mass for $C_{11}H_{12}N_2O$: 188.23.

$^1$H NMR (400 MHz, CDCl$_3$): 7.49-7.41 (m, 5H), 5.66 (s, 1H), 3.43 (s, 3H), 3.16 (s, 3H).

(Step 2) 1,2-dimethyl-3-oxo-5-phenyl-2,3-dihydro-1H-pyrazole-4-carbaldehyde

N,N-Dimethylformamide (3.4 mL, 43.6 mmol) was added to a flask under nitrogen atmosphere. After cooling to 0° C., phosphorus oxychloride (1.4 mL, 15.2 mmol) was added. The resulting reaction mixture was stirred at room temperature for 50 minutes. The resulting reaction mixture was transferred to a reaction flask containing a solution of 1,2-dimethyl-5-phenyl-1H-pyrazol-3(2H)-one (820 mg, 4.36 mmol) in DMF (4.9 mL). The reaction flask was immersed in a preheated oil bath (120° C.) and, after stirring for 12 minutes, cooled to room temperature. 5 N NaOH (15 mL) was added to the cooled reaction mixture. After diluting with icy water, the mixture was extracted with chloroform. The organic layer was dried with sodium sulfate and then filtered. The filtrate was concentrated. After diluting DMF remaining in the resulting residue again with chloroform and then washing with water, the aqueous layer was extracted again with chloroform. The organic layer was collected, dried with sodium sulfate, and then filtered. The filtrate was concentrated. The concentrated residue was subjected to the next step without further purification.

(Step 3) 1,2-dimethyl-3-oxo-5-phenyl-2,3-dihydro-1H-pyrazole-4-carboxylic acid

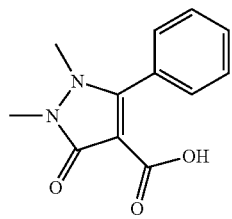 [SMILES: Cn1c(-c2ccccc2)c(C(=O)O)c(=O)n1C]

1,2-Dimethyl-3-oxo-5-phenyl-2,3-dihydro-1H-pyrazole-4-carbaldehyde was dissolved in t-butyl alcohol (23.5 mL) and 2-methyl-2-butene (8.3 mL, 78.5 mmol) was added at 0° C. After adding an aqueous solution of sodium chlorite (80% tech, 0.95 g, 8.7 mmol) in water (10 mL) and a suspension of potassium phosphite monobasic (3.44 g, 25.3 mmol) in water (23.5 mL) to the resulting reaction mixture, the mixture was stirred at room temperature for 10 hours. After adding water to the stirred reaction mixture, the aqueous layer was extracted with ethyl acetate, dichloromethane and 10:1 dichloromethane/methanol. The organic layer was collected, dried with sodium sulfate, and then filtered. The filtrate was concentrated. The resulting residue was washed with a small volume of ethyl acetate to give the target compound as a white solid (350 mg, 1.5 mmol, 35% yield).

MS (ESI pos. ion) m/z: 233 (MH$^+$). Calc'd exact mass for $C_{12}H_{12}N_2O_3$: 232.24.

$^1$H NMR (400 MHz, DMSO): 12.46 (br s, 1H), 7.58-7.47 (m, 5H), 3.62 (s, 3H), 3.48 (s, 3H).

(Step 4) N-(3-fluoro-4-(5-phenylpyrrolo[1,2-b]pyridazin-4-yloxy)phenyl)-1,2-dimethyl-3-oxo-5-phenyl-2,3-dihydro-1H-pyrazole-4-carboxamide

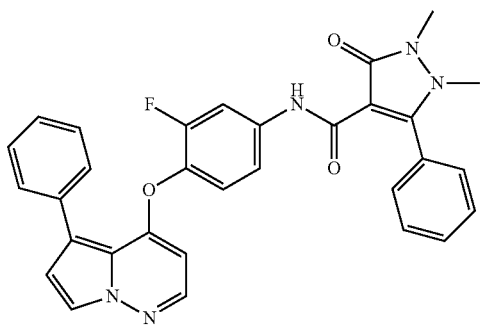 [SMILES: Cn1c(-c2ccccc2)c(C(=O)Nc2ccc(Oc3ccnn4ccc(-c5ccccc5)c34)c(F)c2)c(=O)n1C]

The target compound N-(3-fluoro-4-(5-phenylpyrrolo[1,2-b]pyridazin-4-yloxy)phenyl)-1,2-dimethyl-3-oxo-5-phenyl-2,3-dihydro-1H-pyrazole-4-carboxamide was prepared in the same manner as Example 1, except for using 1,2-dimethyl-3-oxo-5-phenyl-2,3-dihydro-1H-pyrazole-4-carboxylic acid (0.534 mmol) prepared in Step 3 of Example 19 instead of 1,5-dimethyl-3-oxo-2-phenyl-2,3-dihydro-1H-pyrazole-4-carboxylic acid (0.534 mmol), in Step 11 of Example 1.

MS (ESI pos. ion) m/z: 534 (MH$^+$) Calc'd exact mass for $C_{31}H_{24}FN_5O_3$: 533.55.

$^1$H NMR (400 MHz, CDCl$_3$): 11.01 (br s, 1H), 7.85-7.78 (m, 2H), 7.65-7.45 (m, 8H), 7.33 (t, J=7.6 Hz, 2H), 7.25-7.21 (m, 2H), 7.03 (t, J=8.6 Hz, 1H), 6.88 (d, J=2.8 Hz, 1H), 5.64 (dd, J=5.6 Hz, 0.8 Hz, 1H), 3.61 (s, 3H), 3.40 (s, 3H).

Example 20

N-(3-Fluoro-4-(5-(pyridin-2-yl)pyrrolo[1,2-b]pyridazin-4-yloxy)phenyl)-2-(4-fluorophenyl)-1,5-dimethyl-3-oxo-2,3-dihydro-1-pyrazole-4-carboxamide

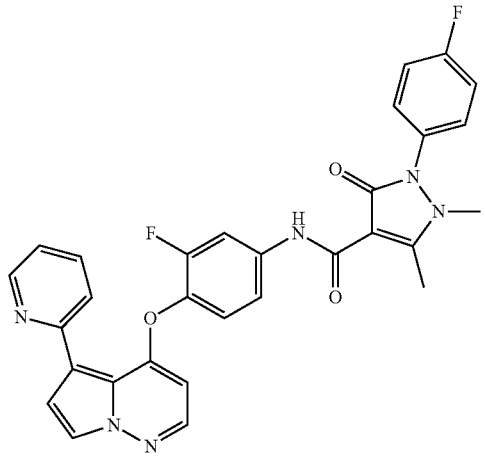 [SMILES: Cc1c(C(=O)Nc2ccc(Oc3ccnn4ccc(-c5ccccn5)c34)c(F)c2)c(=O)n(-c2ccc(F)cc2)n1C]

N-(4-(5-Bromopyrrolo[1,2-b]pyridazin-4-yloxy)-3-fluorophenyl)-2-(4-fluorophenyl)-1,5-dimethyl-3-oxo-2,3-dihydro-1H-pyrazole-4-carb oxamide (70 mg, 0.126 mmol) and Pd(PPh$_3$)$_4$ (11 mg, 0.009 mmol) were suspended in anhydrous toluene (1.4 mL) under nitrogen atmosphere. After adding 2-(tributylstannyl)pyridine, the mixture was stirred for 7 hours under reflux. The resulting reaction mixture was cooled to room temperature, diluted with ethyl acetate, and then filtered with celite. The filtrate was concentrated and the resulting residue was purified by silica gel chromatography (50% ethyl acetate in dichloromethane) to give the target compound as a white solid (33 mg, 0.060 mmol, 48% yield).

MS (ESI pos. ion) m/z: 553 (MH$^+$). Calc'd exact mass for $C_{30}H_{22}F_2N_6O_3$: 552.53.

$^1$H NMR (400 MHz, CDCl$_3$): 10.80 (br s, 1H), 8.64-8.62 (m, 1H), 7.91-7.80 (m, 4H), 7.64-7.60 (m, 1H), 7.37-7.34 (m, 2H), 7.28-7.23 (m, 4H), 7.12-7.08 (m, 2H), 5.77 (d, J=2.8 Hz, 1H), 3.56 (s, 3H), 2.79 (s, 3H).

Example 21

N-(3-Fluoro-4-(5-(thiophen-2-yl)pyrrolo[1,2-b]pyridazin-4-yloxy)phenyl)-2-(4-fluorophenyl)-1,5-dimethyl-3-oxo-2,3-dihydro-1H-pyrazole-4-carboxamide

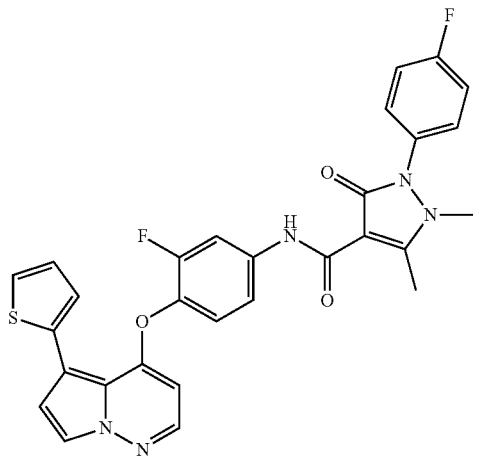 [SMILES: Cc1c(C(=O)Nc2ccc(Oc3ccnn4ccc(-c5cccs5)c34)c(F)c2)c(=O)n(-c2ccc(F)cc2)n1C]

The target compound N-(3-fluoro-4-(5-(thiophen-2-yl)pyrrolo[1,2-b]pyridazin-4-yloxy)phenyl)-2-(4-fluorophenyl)-1,5-dimethyl-3-oxo-2,3-dihydro-1H-pyrazole-4-carboxamide was prepared in the same manner as Example 2.

MS (ESI pos. ion) m/z: 558 (MH+). Calc'd exact mass for $C_{29}H_{21}F_2N_5O_3S$: 557.57.

$^1$H NMR (600 MHz, CDCl$_3$): 10.81 (br s, 1H), 7.90 (dd, J=12.6 Hz, 1.6 Hz, 1H), 7.81 (d, J=5.4 Hz, 1H), 7.75 (d, J=3.0 Hz, 1H), 7.37-7.14 (m, 8H), 7.02-7.00 (m, 1H), 6.95 (d, J=3.0 Hz, 1H), 5.70 (d, J=5.4 Hz, 1H), 3.36 (s, 3H), 2.80 (s, 3H).

Example 22

N-(3-Fluoro-4-(5-(pyrimidin-5-yl)pyrrolo[1,2-b]pyridazin-4-yloxy)phenyl)-2-(4-fluorophenyl)-1,5-dimethyl-3-oxo-2,3-dihydro-1H-pyrazole-4-carboxamide

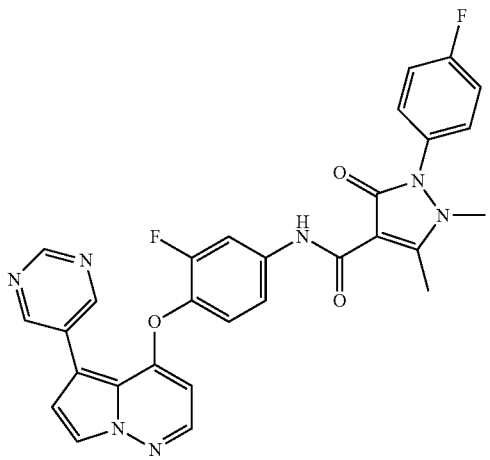 [SMILES: Cc1c(C(=O)Nc2ccc(Oc3ccnn4ccc(-c5cncnc5)c34)c(F)c2)c(=O)n(-c2ccc(F)cc2)n1C]

The target compound N-(3-fluoro-4-(5-(pyrimidin-5-yl)pyrrolo[1,2-b]pyridazin-4-yloxy)phenyl)-2-(4-fluorophenyl)-1,5-dimethyl-3-oxo-2,3-dihydro-1H-pyrazole-4-carboxamide was prepared in the same manner as Example 2.

MS (ESI pos. ion) m/z: 554 (MH+). Calc'd exact mass for $C_{29}H_{21}F_2N_7O_3$: 553.52.

$^1$H NMR (400 MHz, CDCl$_3$): 10.82 (br s, 1H), 9.06 (s, 1H), 8.99 (s, 2H), 7.92-7.86 (m, 3H), 7.37-7.09 (m, 6H), 6.93 (d, J=2.8 Hz, 1H), 5.79 (dd, J=5.6 Hz, 0.8 Hz, 1H), 3.36 (s, 3H), 2.79 (s, 3H).

Example 23

N-(3-Fluoro-4-(5-(thiazol-2-yl)pyrrolo[1,2-b]pyridazin-4-yloxy)phenyl)-2-(4-fluorophenyl-1,5-dimethyl-3-oxo-2,3-dihydro-1H-pyrazole-4-carboxamide

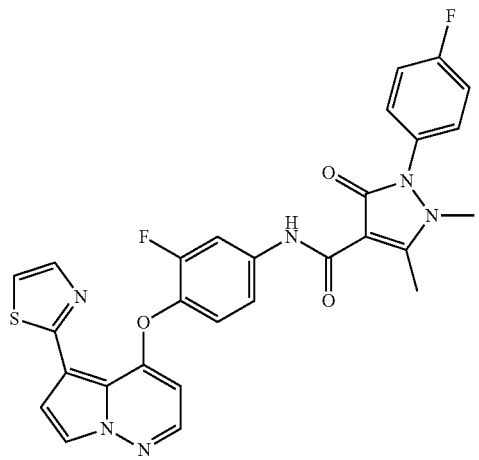 [SMILES: Cc1c(C(=O)Nc2ccc(Oc3ccnn4ccc(-c5nccs5)c34)c(F)c2)c(=O)n(-c2ccc(F)cc2)n1C]

The target compound was prepared in the same manner as Example 20.

MS (ESI pos. ion) m/z: 559 (MH+). Calc'd exact mass for $C_{28}H_{20}F_2N_6O_3S$: 558.56.

$^1$H NMR (400 MHz, CDCl$_3$): 10.84 (br s, 1H), 7.93 (dd, J=12.6 Hz, 2.4 Hz, 1H), 7.87 (d, J=5.2 Hz, 1H), 7.80-7.77 (m, 2H), 7.48 (d, J=2.8 Hz, 1H), 7.38-7.19 (m, 7H), 5.83 (d, J=4.0 Hz, 1H), 3.37 (s, 3H), 2.80 (s, 3H).

Example 24

N-(3-Fluoro-4-(5-(pyrazin-2-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide

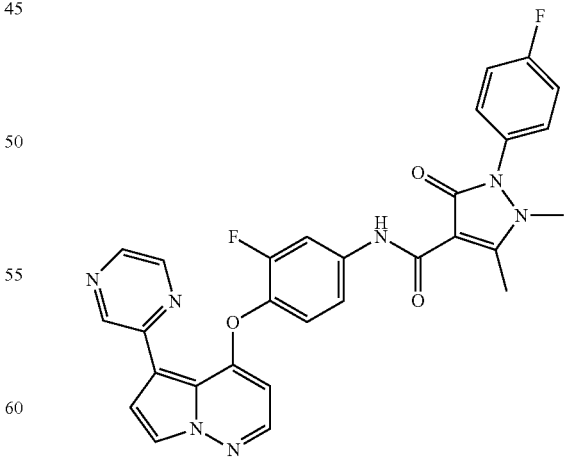

The target compound was prepared in the same manner as Example 20.

MS (ESI pos. ion) m/z: 554 (MH+). Calc'd exact mass for $C_{29}H_{21}F_2N_7O_3$: 553.52.

¹H NMR (400 MHz, CDCl₃): 10.83 (br s, 1H), 9.10 (s, 1H), 8.58 (s, 1H), 8.36 (s, 1H), 7.92-7.87 (m, 3H), 7.36-7.25 (m, 6H), 7.13 (t, J=8.7 Hz, 1H), 5.84 (d, J=5.4 Hz, 1H), 3.36 (s, 3H), 2.79 (s, 3H).

Example 25

N-(3-Dluoro-4-(5-(piperidin-4-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide

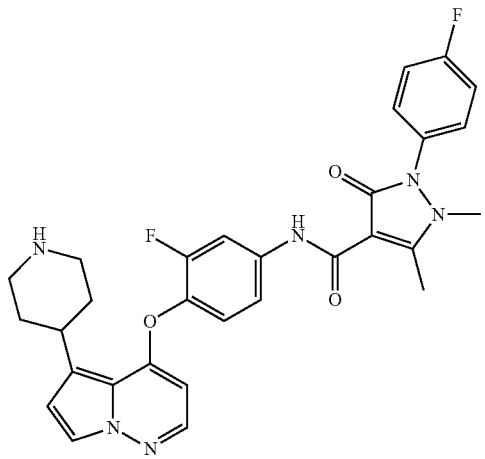 [SMILES: Cc1c(C(=O)Nc2ccc(Oc3ccnn4ccc(C5CCNCC5)c34)c(F)c2)c(=O)n(-c2ccc(F)cc2)n1C]

The target compound N-(3-fluoro-4-(5-(piperidin-4-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide was prepared in the same manner as Example 2.

MS (ESI pos. ion) m/z: 559 (MH⁺) Calc'd exact mass for $C_{30}H_{28}F_2N_6O_3$: 558.58.

¹H NMR (400 MHz, CDCl₃): 10.83 (br s, 1H), 7.92-7.89 (m, 1H), 7.74-7.72 (m, 1H), 7.67 (t, J=2.4 Hz, 1H), 7.38-7.24 (m, 5H), 7.16 (t, J=8.8 Hz, 1H), 6.72 (dd, J=8.0 Hz, 2.8 Hz, 1H), 5.57 (t, J=5.8 Hz, 1H), 3.37 (s, 3H), 2.80 (s, 3H), 2.21-1.82 (m, 4H), 1.39-1.08 (m, 2H), 0.95-0.81 (m, 2H).

Example 26

N-(3-Fluoro-4-(5-(pyridin-3-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide

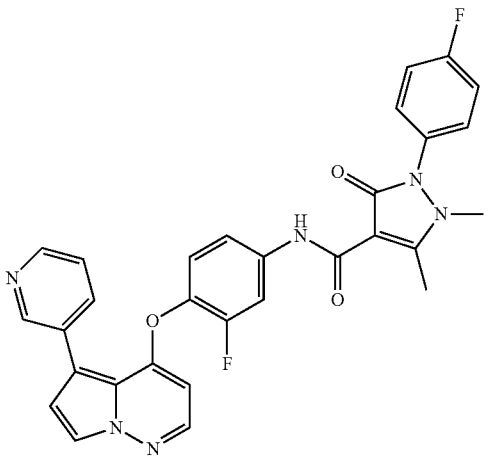 [SMILES: Cc1c(C(=O)Nc2ccc(Oc3ccnn4ccc(-c5cccnc5)c34)c(F)c2)c(=O)n(-c2ccc(F)cc2)n1C]

The target compound N-(3-fluoro-4-(5-(pyridin-3-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide was prepared in the same manner as Example 2.

MS (ESI pos. ion) m/z: 553 (MH⁺) Calc'd exact mass for $C_{30}H_{22}F_2N_6O_3$: 552.53.

¹H NMR (400 MHz, CDCl₃): 10.80 (br s, 1H), 8.88 (d, J=2.4 Hz, 1H), 8.46 (dd, J=4.8 Hz, 1.8 Hz, 1H), 7.95 (d, J=7.8 Hz, 1H), 7.90-7.84 (m, 3H), 7.36-7.08 (m, 7H), 6.91 (d, J=3.0 Hz, 1H), 5.73 (d, J=4.8 Hz, 1H), 3.36 (s, 3H), 2.79 (s, 3H).

Example 27

N-(3-Fluoro-4-(5-(pyridin-4-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide

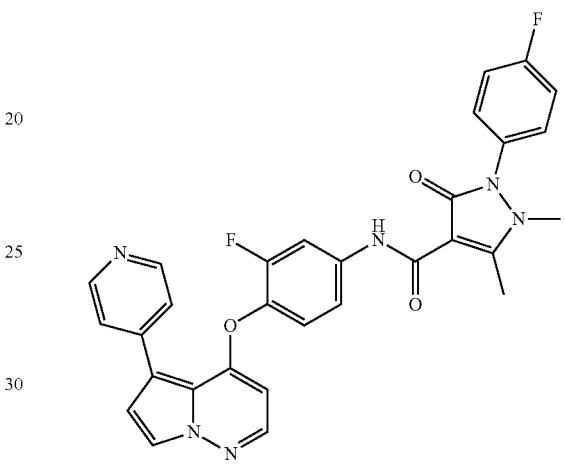

The target compound N-(3-fluoro-4-(5-(pyridin-4-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide was prepared in the same manner as Example 2.

MS (ESI pos. ion) m/z: 553 (MH⁺). Calc'd exact mass for $C_{30}H_{22}F_2N_6O_3$: 552.53.

¹H NMR (400 MHz, CDCl₃): 10.82 (br s, 1H), 8.55 (dd, J=4.6 Hz, 1.4 Hz, 2H), 7.94-7.88 (m, 2H), 7.83 (d, J=3.2 Hz, 1H), 7.57 (dd, J=4.4 Hz, 1.6 Hz, 2H), 7.37-7.09 (m, 6H), 6.96 (d, J=3.2 Hz, 1H), 5.78 (d, J=4.4 Hz, 1H) 3.36 (s, 3H), 2.79 (s, 3H).

Example 28

N-(3-Fluoro-4-(5-(thiophen-3-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide

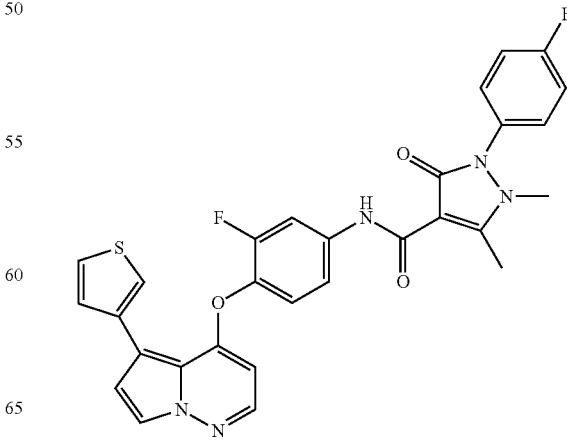

The target compound N-(3-fluoro-4-(5-(thiophen-3-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide was prepared in the same manner as Example 2.

MS (ESI pos. ion) m/z: 558 (MH$^+$). Calc'd exact mass for $C_{29}H_{21}F_2N_5O_3S$: 557.57.

$^1$H NMR (600 MHz, CDCl$_3$): 10.81 (br s, 1H), 7.91 (dd, J=12.6 Hz, 2.4 Hz, 1H), 7.80 (d, J=5.4 Hz, 1H), 7.77 (d, J=2.4 Hz, 1H), 7.45-7.25 (m, 8H), 7.13 (t, J=8.7 Hz, 1H), 6.92 (d, J=3.0 Hz, 1H), 5.68 (d, J=5.4 Hz, 1H), 3.37 (s, 3H), 2.80 (s, 3H).

Example 29

N-(3-Fluoro-4-(5-(3,5-dimethylisoxazol-4-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide

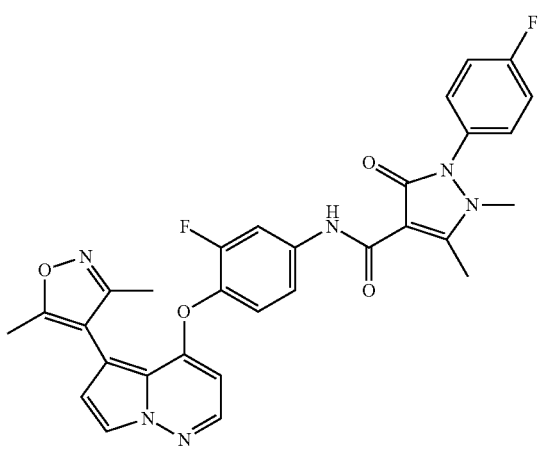 [SMILES: Cc1noc(C)c1-c1ccn2nccc(Oc3ccc(NC(=O)c4c(C)n(C)n(-c5ccc(F)cc5)c4=O)cc3F)c12]

The target compound N-(3-fluoro-4-(5-(3,5-dimethylisoxazol-4-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide was prepared in the same manner as Example 2.

MS (ESI pos. ion) m/z: 571 (MH$^+$) Calc'd exact mass for $C_{30}H_{24}F_2N_6O_4$ 570.55.

$^1$H NMR (400 MHz, CDCl$_3$): 10.80 (br s, 1H), 7.89-7.79 (m, 3H), 7.37-7.21 (m, 5H), 7.00 (t, J=8.8 Hz, 1H), 6.66 (d, J=2.8 Hz, 1H), 5.65 (d, J=5.2 Hz, 1H), 3.36 (s, 3H), 2.79 (s, 3H), 2.35 (s, 3H), 2.23 (s, 3H).

Example 30

N-(3-Fluoro-4-(5-(6-methylpyridin-3-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide

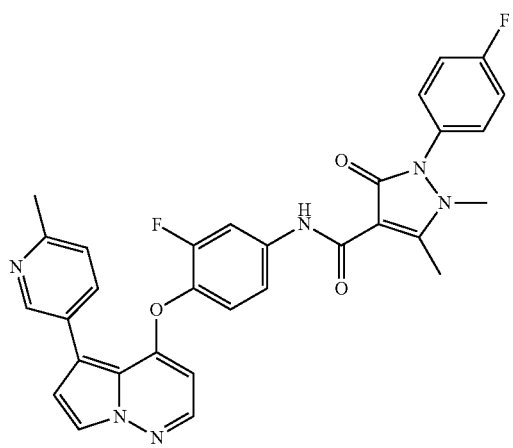 [SMILES: Cc1ccc(-c2ccn3nccc(Oc4ccc(NC(=O)c5c(C)n(C)n(-c6ccc(F)cc6)c5=O)cc4F)c23)cn1]

The target compound N-(3-fluoro-4-(5-(6-methylpyridin-3-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide was prepared in the same manner as Example 2.

MS (ESI pos. ion) m/z: 567 (MH$^+$). Calc'd exact mass for $C_{31}H_{24}F_2N_6O_3$: 566.56.

$^1$H NMR (600 MHz, CDCl$_3$): 10.79 (br s, 1H), 8.76 (d, J=1.8 Hz, 1H), 7.88 (dd, J=12.0 Hz, 2.4 Hz, 1H), 7.85-7.82 (m, 3H), 7.36-7.22 (m, 5H), 7.14 (d, J=7.8 Hz, 1H), 7.08 (t, J=8.4 Hz, 1H), 6.88 (d, J=3.0 Hz, 1H), 5.70 (d, J=5.4 Hz, 1H), 3.36 (s, 3H), 2.79 (s, 3H), 2.55 (s, 3H).

Example 31

N-(3-Fluoro-4-(5-(2-methylpyridin-4-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide

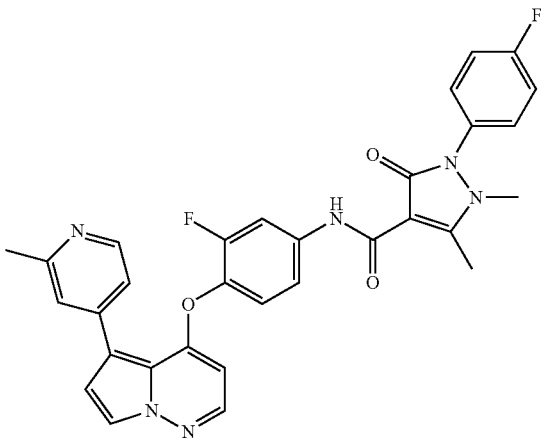 [SMILES: Cc1cc(-c2ccn3nccc(Oc4ccc(NC(=O)c5c(C)n(C)n(-c6ccc(F)cc6)c5=O)cc4F)c23)ccn1]

The target compound N-(3-fluoro-4-(5-(2-methylpyridin-4-yl)pyrrolo[1,2-b]pyridazin-4-yloxy)phenyl)-2-(4-fluorophenyl)-1,5-dimethyl-3-oxy-2,3-dihydro-1H-pyrazole-4-carboxamide was prepared in the same manner as Example 2.

MS (ESI pos. ion) m/z: 567 (MH$^+$). Calc'd exact mass for $C_{31}H_{24}F_2N_6O_3$: 566.56.

$^1$H NMR (400 MHz, CDCl$_3$): 10.81 (br s, 1H), 8.43 (d, J=5.2 Hz, 1H), 7.94-7.82 (m, 3H), 7.46 (s, 1H), 7.39-7.24 (m, 6H), 7.09 (t, J=8.4 Hz, 1H), 6.95 (d, J=2.8 Hz, 1H), 5.78 (d, J=5.2 Hz, 1H), 3.36 (s, 3H), 2.79 (s, 3H) 2.55 (s, 3H).

Example 32

N-(3-Fluoro-4-(5-(1-hydroxyethyl)pyrrolo[1,2-b]pyridazin-4-yloxy)phenyl)-2-(4-fluorophenyl)-1,5-dimethyl-3-oxo-2,3-dihydro-1H-pyrazole-4-carboxamide

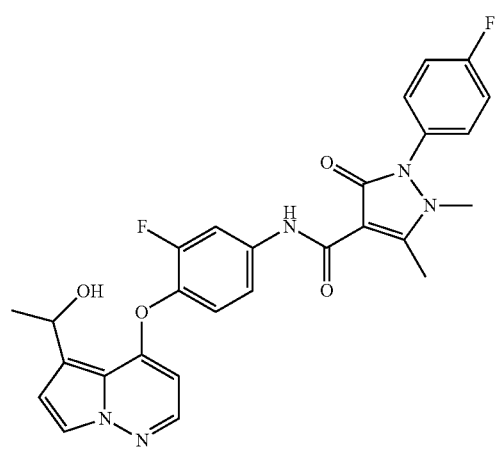 [SMILES: Cc1c(C(=O)Nc2ccc(Oc3ccnn4ccc(C(C)O)c34)c(F)c2)c(=O)n(-c2ccc(F)cc2)n1C]

The target compound was prepared as follows:

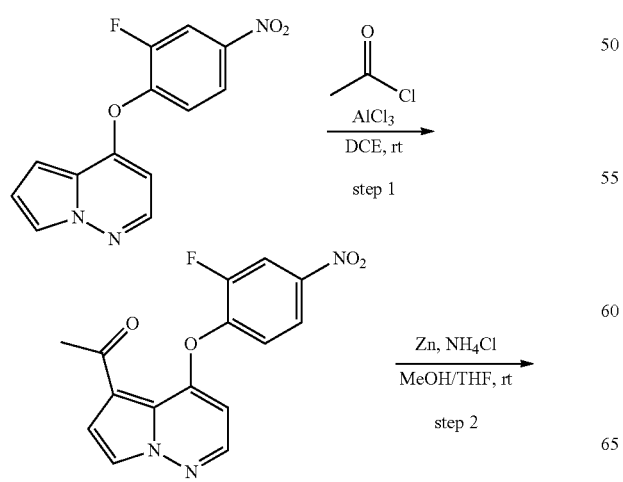

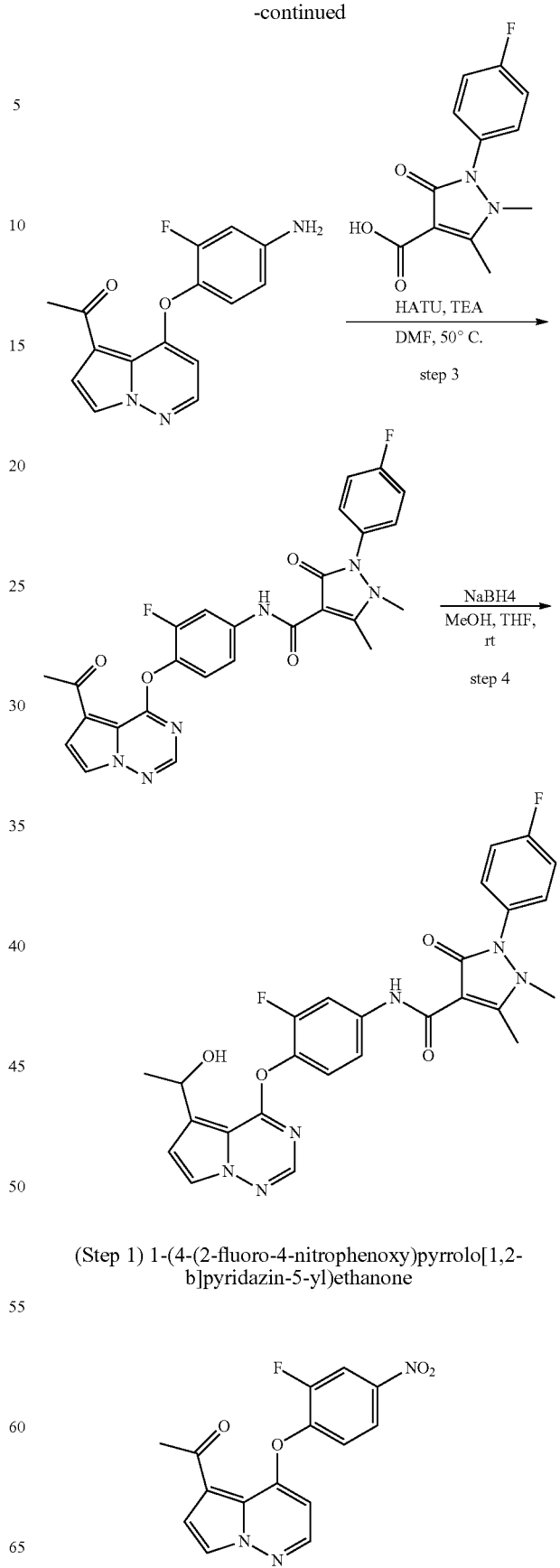

(Step 1) 1-(4-(2-fluoro-4-nitrophenoxy)pyrrolo[1,2-b]pyridazin-5-yl)ethanone

AlCl₃ (1.46 g, 10.98 mmol) was added to a solution of 4-(2-fluoro-4-nitrophenoxy)pyrrolo[1,2-b]pyridazine (600 mg, 2.19 mmol) in dichloroethane (60 mL). After stirring at room temperature for 1 hour and adding acetyl chloride (0.17 mL, 2.42 mmol), the mixture was further stirred for 3 hours. The resulting reaction mixture was neutralized with saturated sodium bicarbonate aqueous solution. The resulting mixture was filtered through celite. After phase separation of the filtrate, the organic layer was dried with magnesium sulfate and then filtered. The filtrate was concentrated and then purified by silica gel chromatography (1-6% ethyl acetate in dichloromethane) to give the target compound as a white solid (640 mg, 2.03 mmol, 93% yield).

¹H NMR (400 MHz, CDCl₃): 8.24-8.16 (m, 3H), 7.58 (d, J=4.8 Hz, 1H), 7.45 (dd, J=8.8 Hz, 7.2 Hz, 1H), 6.81 (d, J=4.8 Hz, 1H), 6.06 (dd, J=5.6 Hz, 1.2 Hz, 1H) 2.75 (s, 3H).

(Step 2) 1-(4-(2-fluoro-4-aminophenoxy)pyrrolo[1,2-b]pyridazin-5-yl)ethanone

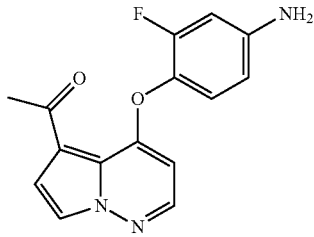 [SMILES: CC(=O)c1ccn2nccc(Oc3ccc(N)cc3F)c12]

The target compound 1-(4-(2-fluoro-4-aminophenoxy)pyrrolo[1,2-b]pyridazin-5-yl)ethanone was prepared in the same manner as Step 5 of Example 13.

(Step 3) N-(4-(5-acetylpyrrolo[1,2-b]pyridazin-4-yloxy)-3-fluorophenyl)-2-(4-fluorophenyl)-1-5-dimethyl-3-oxo-2,3-dihydro-1H-pyrazole-4-carboxamide

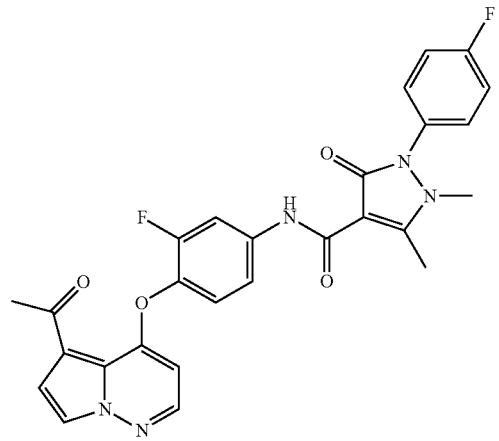 [SMILES: CC(=O)c1ccn2nccc(Oc3ccc(NC(=O)c4c(C)n(C)n(-c5ccc(F)cc5)c4=O)cc3F)c12]

The target compound N-(4-(5-acetylpyrrolo[1,2-b]pyridazin-4-yloxy)-3-fluorophenyl)-2-(4-fluorophenyl)-1-5-dimethyl-3-oxo-2,3-dihydro-1H-pyrazole-4-carboxamide was prepared in the same manner as Step 6 of Example 13 using the compound of Step 2 of this example.

(Step 4) N-(3-fluoro-4-(5-(1-hydroxyethyl)pyrrolo[1,2-b]pyridazin-4-yloxy)phenyl)-2-(4-fluorophenyl)-1,5-dimethyl-3-oxo-2,3-dihydro-1H-pyrazole-4-carboxamide

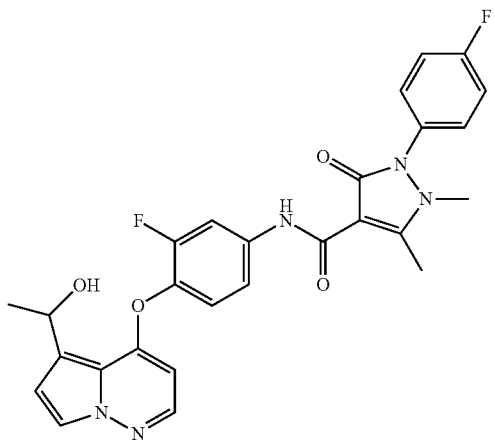 [SMILES: Cc1c(C(=O)Nc2ccc(Oc3ccnn4ccc(C(C)O)c34)c(F)c2)c(=O)n(-c2ccc(F)cc2)n1C]

NaBH₄ (11 mg, 0.288 mmol) was added to a suspension of N-(4-(5-acetylpyrrolo[1,2-b]pyridazin-4-yloxy)-3-fluorophenyl)-2-(4-fluorophenyl)-1-5-dimethyl-3-oxo-2,3-dihydro-1H-pyrazole-4-carboxamide (50 mg, 0.096 mmol) in tetrahydrofuran (2.5 mL) and methanol (3 mL) under nitrogen atmosphere. After stirring at room temperature for 30 minutes, saturated ammonium chloride aqueous solution was added to the resulting reaction mixture. After extraction with dichloromethane, the organic layer was dried with sodium sulfate and then filtered. The filtrate was concentrated. The resulting residue was purified by silica gel chromatography (10% ethyl acetate in dichloromethane) to give the target compound as a white solid (16 mg, 0.029 mmol, 32% yield).

MS (ESI pos. ion) m/z: 542 (MNa⁺). Calc'd exact mass for C₂₇H₂₃F₂N₅O₄: 519.5.

¹H NMR (400 MHz, CDCl₃): 10.81 (br s, 1H), 7.91-7.88 (m, 2H) 7.38-7.24 (m, 6H), 7.17 (t, J=8.4 Hz, 1H), 6.73-6.71 (m, 2H), 5.73 (d, J=5.2 Hz, 1H), 5.39 (m, 1H), 3.96 (br s, 3H), 3.36 (s, 3H), 2.80 (s, 3H). 1.73 (d, J=6.8 Hz, 1H).

Example 33

N-(4-(5-Acetylpyrrolo[1,2-b]pyridazin-4-yloxy)-3-fluorophenyl)-2-(4-fluorophenyl)-1-5-dimethyl-3-oxo-2,3-dihydro-1H-pyrazole-4-carboxamide

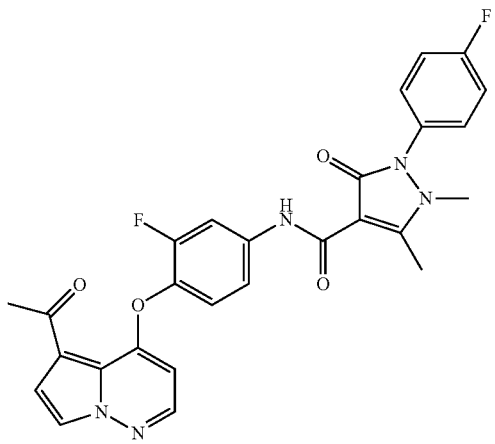 [SMILES: CC(=O)c1ccn2nccc(Oc3ccc(NC(=O)c4c(C)n(C)n(-c5ccc(F)cc5)c4=O)cc3F)c12]

The target compound N-(4-(5-acetylpyrrolo[1,2-b]pyridazin-4-yloxy)-3-fluorophenyl)-2-(4-fluorophenyl)-1-5-dimethyl-3-oxo-2,3-dihydro-1H-pyrazole-4-carboxamide was prepared in the same manner as Example 32.

MS (ESI pos. ion) m/z: 518 (MH⁺). Calc'd exact mass for $C_{27}H_{21}F_2N_5O_4$: 517.48.

¹H NMR (400 MHz, CDCl₃): 10.84 (br s, 1H), 8.16 (d, J=5.2 Hz, 1H), 7.92 (dd, J=12.4 Hz, 2.4 Hz, 1H), 7.54 (d, J=5.2 Hz, 1H), 7.38-7.24 (m, 5H), 7.18 (t, J=8.8 Hz, 1H), 6.85 (d, J=5.2 Hz, 1H), 5.98 (d, J=5.2 Hz, 1H), 3.37 (s, 3H), 2.80 (s, 3H), 2.73 (s, 3H).

Example 34

N-(4-(5-Acetylpyrrolo[1,2-b]pyridazin-4-yloxy)-3-fluorophenyl)-1,5-dimethyl-3-oxo-2-phenyl-2,3-dihydro-1H-pyrazole-4-carboxamide

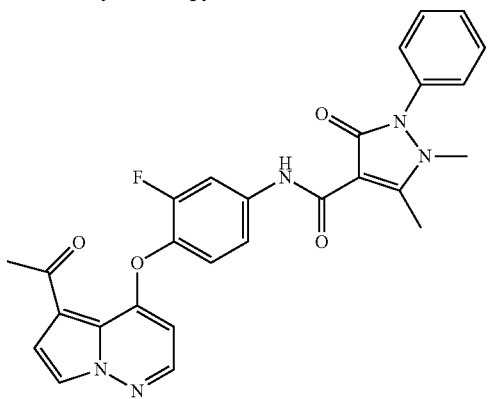

The target compound N-(4-(5-acetylpyrrolo[1,2-b]pyridazin-4-yloxy)-3-fluorophenyl)-1,5-dimethyl-3-oxo-2-phenyl-2,3-dihydro-1H-pyrazole-4-carboxamide was prepared in the same manner as Example 32.

MS (ESI pos. ion) m/z: 500 (MH⁺) Calc'd exact mass for $C_{27}H_{22}FN_5O_4$: 499.49.

¹H NMR (400 MHz, CDCl₃): 10.91 (br s, 1H), 8.16 (d, J=5.6 Hz, 1H), 7.93 (dd, J=12.8 Hz, 2.4 Hz, 1H), 7.59-7.49 (m, 4H), 7.37-7.29 (m, 3H), 7.18 (t, J=8.4 Hz, 1H), 6.85 (d, J=4.8 Hz, 1H), 5.99 (d, J=4.8 Hz, 1H), 3.39 (s, 3H), 2.80 (s, 3H), 2.73 (s, 3H).

Example 35

N-(3-Fluoro-4-(5-(1-hydroxyethyl)pyrrolo[1,2-b]pyridazin-4-yloxy)phenyl)-1,5-dimethyl-3-oxo-2-phenyl-2,3-dihydro-1H-pyrazole-4-carboxamide

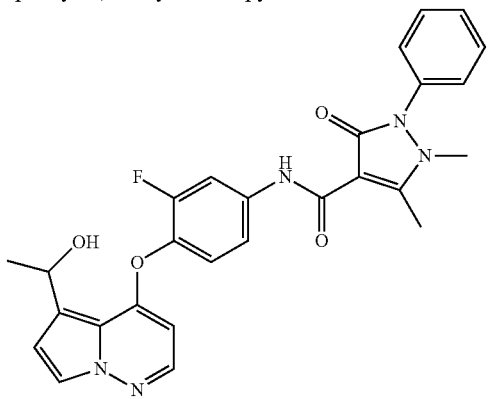

The target compound N-(4-(5-acetylpyrrolo[1,2-b]pyridazin-4-yloxy)-3-fluorophenyl)-2-(4-fluorophenyl)-1-5-dimethyl-3-oxo-2,3-dihydro-1H-pyrazole-4-carboxamide was prepared in the same manner as Example 32.

MS (ESI pos. ion) m/z: 524 (MNa⁺). Calc'd exact mass for $C_{27}H_{24}FN_5O_4$: 501.51.

¹H NMR (400 MHz, CDCl₃): 10.88 (br s, 1H), 7.92-7.88 (m, 2H) 7.59-7.46 (m, 3H), 7.38-7.27 (m, 3H), 7.16 (t, J=8.8 Hz, 1H), 6.73-6.70 (m, 2H), 5.73 (dd, J=5.2 Hz, 0.8 Hz, 1H), 5.40 (m, 1H), 3.96 (d, J=3.2 Hz, 1H), 3.38 (s, 3H), 2.80 (s, 3H). 1.73 (d, J=6.4 Hz, 1H).

Example 36

N-(3-Fluoro-4-(5-thiazol-2-yl)pyrrolo[1,2-b]pyridazin-4-yloxy)phenyl)-1,5-dimethyl-3-oxo-2-phenyl-2,3-dihydro-1H-pyrazole-4-carboxamide

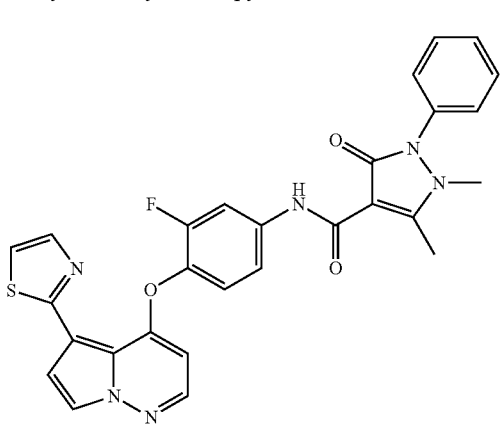

The target compound was prepared in the same manner as Example 20.

MS (ESI pos. ion) m/z: 541 (MH⁺). Calc'd exact mass for $C_{28}H_{21}FN_6O_3S$: 540.57.

¹H NMR (400 MHz, CDCl₃): 10.91 (br s, 1H), 7.94 (dd, J=12.4 Hz, 2.8 Hz, 1H), 7.87 (d, J=5.2 Hz, 1H), 7.78 (dd, J=3.6 Hz, 2.8 Hz, 1H), 7.69-7.64 (m, 2H), 7.59-7.44 (m, 4H), 7.38-7.29 (m, 2H), 7.24-7.19 (m, 2H), 5.83 (dd, J=5.2 Hz, 0.8 Hz, 1H), 3.38 (s, 3H), 2.80 (s, 3H).

Example 37

N-(3-Fluoro-4-(5-(pyridin-3-yl)pyrrolo[1,2-b]pyridazin-4-yloxy)phenyl)-1,5-dimethyl-3-oxo-2-phenyl-2,3-dihydro-1H-pyrazole-4-carboxamide

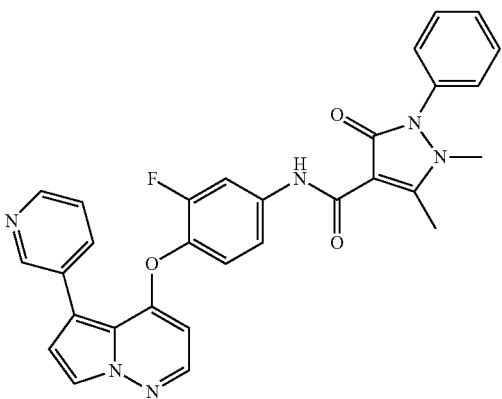 [SMILES: Cc1c(C(=O)Nc2ccc(Oc3ccnn4ccc(-c5cccnc5)c34)c(F)c2)c(=O)n(-c2ccccc2)n1C]

The target compound N-(3-fluoro-4-(5-(pyridin-3-yl)pyrrolo[1,2-b]pyridazin-4-yloxy)phenyl)-1,5-dimethyl-3-oxo-2-phenyl-2,3-dihydro-1H-pyrazole-4-carboxamide was prepared in the same manner as Example 2.

MS (ESI pos. ion) m/z: 535 (MH⁺) Calc'd exact mass for $C_{30}H_{23}FN_6O_3$: 534.54.

¹H NMR (400 MHz, CDCl₃): 10.87 (br s, 1H), 8.87 (d, J=2.0 Hz, 1H), 8.46 (dd, J=4.8 Hz, 1.6 Hz, 1H), 7.97-7.83 (m, 4H), 7.58-7.46 (m, 3H), 7.37-7.22 (m, 4H), 7.04 (t, J=8.4 Hz, 1H), 6.90 (d, J=2.8 Hz, 1H), 5.74 (d, J=5.2 Hz, 1H), 3.38 (s, 3H), 2.80 (s, 3H).

Example 38

N-(4-(5-eEthylpyrrolo[1,2-b]pyridazin-4-yloxy)-3-fluorophenyl)-2-(4-fluorophenyl)-1,5-dimethyl-3-oxo-2,3-dihydro-1H-pyrazole-4-carboxamide

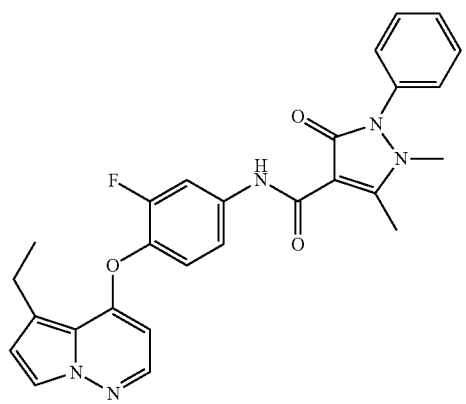 [SMILES: CCc1ccn2nccc(Oc3ccc(NC(=O)c4c(C)n(C)n(-c5ccccc5)c4=O)cc3F)c12]

The target compound N-(4-(5-ethylpyrrolo[1,2-b]pyridazin-4-yloxy)-3-fluorophenyl)-2-(4-fluorophenyl)-1,5-dimethyl-3-oxo-2,3-dihydro-1H-pyrazole-4-carb oxamide was prepared in the same manner as Example 2.

MS (ESI pos. ion) m/z: 504 (MH⁺). Calc'd exact mass for $C_{27}H_{23}F_2N_5O_3$: 503.50.

¹H NMR (400 MHz, CDCl₃): 10.81 (br s, 1H), 7.90 (dd, J=12.4 Hz, 2.4 Hz, 1H), 7.70 (d, J=5.2 Hz, 1H), 7.65 (d, J=2.8 Hz, 1H), 7.38-7.34 (m, 2H), 7.28-7.24 (m, 3H), 7.17 (t, J=8.4 Hz, 1H), 6.64 (d, J=2.8 Hz, 1H), 5.52 (d, J=5.2 Hz, 1H), 3.36 (s, 3H), 3.02 (q, J=7.6 Hz, 2H), 2.80 (s, 3H), 1.31 (t, J=7.6 Hz, 3H).

Example 39

N-(3-Fluoro-4-(pyrrolo[1,2-b]pyridazin-4-yloxy)phenyl)-2-(4-fluorophenyl)-1,5-dimethyl-3-oxo-2,3-dihydro-1H-pyrazole-4-carboxamide

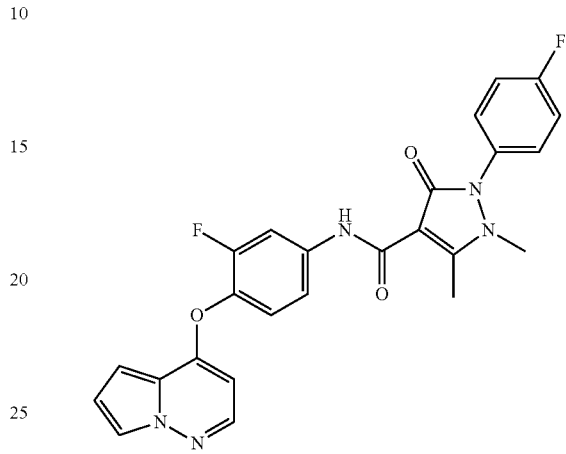

The target compound N-(3-fluoro-4-(pyrrolo[1,2-b]pyridazin-4-yloxy)phenyl)-2-(4-fluorophenyl)-1,5-dimethyl-3-oxo-2,3-dihydro-1H-pyrazole-4-carboxamide was prepared in the same manner as Example 9.

MS (ESI pos. ion) m/z: 476 (MH⁺) Calc'd exact mass for $C_{25}H_{19}F_2N_5O_3$: 475.45.

¹H NMR (400 MHz, CDCl₃): 10.81 (br s, 1H), 7.89 (dd, J=12.4 Hz, 2.4 Hz, 1H), 7.83 (d, J=5.2 Hz, 1H), 7.74 (dd, J=2.4 Hz, 1.6 Hz, 1H), 7.38-7.34 (m, 2H), 7.29-7.24 (m, 2H), 7.17 (t, J=8.8 Hz, 1H), 6.81 (dd, J=4.4 Hz, 2.4 Hz, 1H), 6.75 (dd, J=4.4 Hz, 1.6 Hz, 1H), 5.68 (dd, J=5.2 Hz, 0.8 Hz, 1H), 3.36 (s, 3H), 2.99 (s, 3H).

Example 40

N-(3-Fluoro-4-(5-(pyridin-4-yl)pyrrolo[1,2-b]pyridazin-4-yloxy)phenyl)-1,5-dimethyl-3-oxo-2-phenyl-2,3-dihydro-1H-pyrazole-4-carboxamide

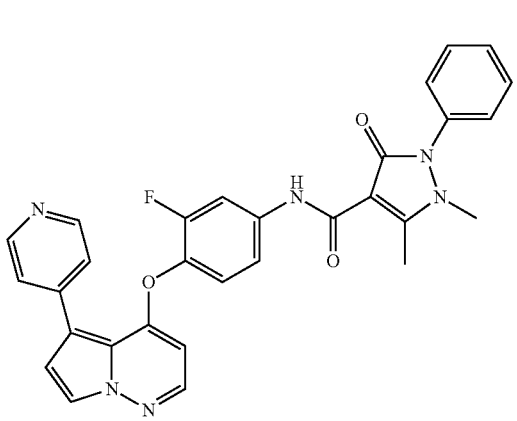 [SMILES: Cc1c(C(=O)Nc2ccc(Oc3ccnn4ccc(-c5ccncc5)c34)c(F)c2)c(=O)n(-c2ccccc2)n1C]

The target compound N-(3-fluoro-4-(5-(pyridin-4-yl)pyrrolo[1,2-b]pyridazin-4-yloxy)phenyl)-1,5-dimethyl-3-oxo-2-phenyl-2,3-dihydro-1H-pyrazole-4-carboxamide was prepared in the same manner as Example 2.

MS (ESI pos. ion) m/z: 535 (MH+) Calc'd exact mass for $C_{30}H_{23}FN_6O_3$: 534.54.

$^1$H NMR (400 MHz, CDCl$_3$): 10.89 (br s, 1H), 8.56-8.53 (m, 2H), 7.92 (dd, J=12.4 Hz, 2.4 Hz, 1H), 7.89 (d, J=5.2 Hz, 1H), 7.83 (d, J=2.8 Hz, 1H), 7.59-7.46 (m, 5H), 7.37-7.35 (m, 2H), 7.27-7.24 (m, 1H), 7.08 (t, J=8.4 Hz, 1H), 6.96 (d, J=2.8 Hz, 1H), 5.79 (d, J=5.2 Hz, 1H), 3.38 (s, 3H), 2.80 (s, 3H).

Example 41

N-(4-(5-Chloropyrrolo[1,2-b]pyridazin-4-yloxy)-3-fluorophenyl)-2-(4-fluorophenyl)-1,5-dimethyl-3-oxo-2,3-dihydro-1H-pyrazole-4-carboxamide

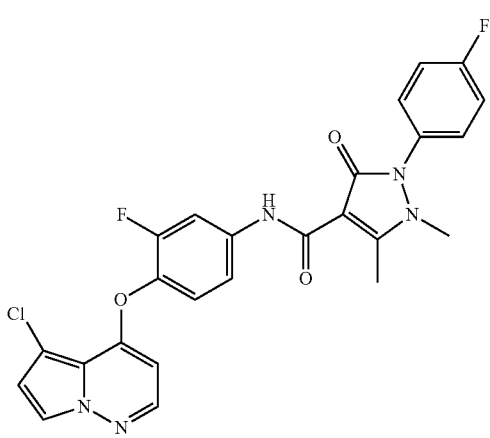 [SMILES: Cc1c(C(=O)Nc2ccc(Oc3ccnn4ccc(Cl)c34)c(F)c2)c(=O)n(-c2ccc(F)cc2)n1C]

The target compound N-(4-(5-chloropyrrolo[1,2-b]pyridazin-4-yloxy)-3-fluorophenyl)-2-(4-fluorophenyl)-1,5-dimethyl-3-oxo-2,3-dihydro-1H-pyrazole-4-carboxamide was prepared in the same manner as Example 1.

MS (ESI pos. ion) m/z: 509 (MH+). Calc'd exact mass for $C_{25}H_{18}ClF_2N_5O_3$: 509.89.

$^1$H NMR (600 MHz, CDCl$_3$): 10.81 (br s, 1H), 7.90 (dd, J=6.6, 2.4 Hz, 1H), 7.76 (d, J=4.8 Hz, 1H), 7.63 (d, J=3.0, 1H), 7.37-7.25 (m, 5H), 7.20 (t, J=2.7, 1H), 6.72 (d, J=2.4, 1H), 5.63 (d, J=5.4, 1H), 3.36 (s, 3H), 2.80 (s, 3H).

Example 42

N-(4-(5-Chloropyrrolo[1,2-b]pyridazin-4-yloxy)-3-fluorophenyl)-1,5-dimethyl-3-oxo-2-phenyl-2,3-dihydro-1H-pyrazole-4-carboxamide

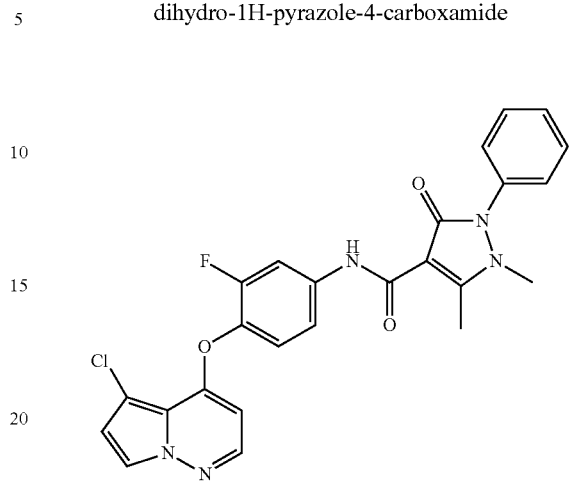

The target compound N-(4-(5-chloropyrrolo[1,2-b]pyridazin-4-yloxy)-3-fluorophenyl)-1,5-dimethyl-3-oxo-2-phenyl-2,3-dihydro-1H-pyrazole-4-carboxamide was prepared in the same manner as Example 1.

MS (ESI pos. ion) m/z: 492 (MH+). Calc'd exact mass for $C_{25}H_{19}ClFN_5O_3$: 491.90.

$^1$H NMR (600 MHz, CDCl$_3$): 10.89 (br s, 1H), 7.91 (dd, J=12.3, 2.1 Hz, 1H), 7.76 (d, J=7.2, 1H), 7.63 (d, J=3.0 Hz, 1H), 7.57 (t, J=7.8, 2H), 7.49 (t, J=7.5, 1H), 7.36 (d, J=8.4, 2H), 7.29 (d, J=7.8, 1H), 7.19 (t, J=8.7, 1H), 6.72 (d, J=2.4, 1H), 5.64 (d, J=5.4, 1H), 3.38 (s, 3H), 2.80 (s, 3H).

Example 43

N-(3-Fluoro-4-(2-(thiophen-2-yl)-1H-pyrrolo[2,3-b]pyridin-4-yloxy)phenyl)-2-(4-fluorophenyl)-1,5-dimethyl-3-oxo-2,3-dihydro-1H-pyrazole-4-carboxamide

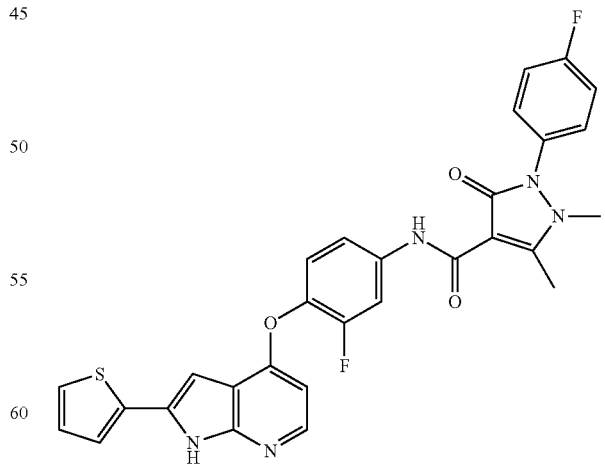

The target compound N-(3-fluoro-4-(2-(thiophen-2-yl)-1H-pyrrolo[2,3-b]pyridin-4-yloxy)phenyl)-2-(4-fluorophenyl)-1,5-dimethyl-3-oxo-2,3-dihydro-1H-pyrazole-4-carboxamide was prepared in the same manner as Example 10.

MS (ESI pos. ion) m/z: 558 (MH+). Calc'd exact mass for C29H21F2N5O3S: 557.57.

Example 44

N-(3-Fluoro-4-(2-(thiophen-3-yl)-1H-pyrrolo[2,3-b]pyridin-4-yloxy)phenyl)-2-(4-fluorophenyl)-1,5-dimethyl-3-oxo-2,3-dihydro-1H-pyrazole-4-carboxamide

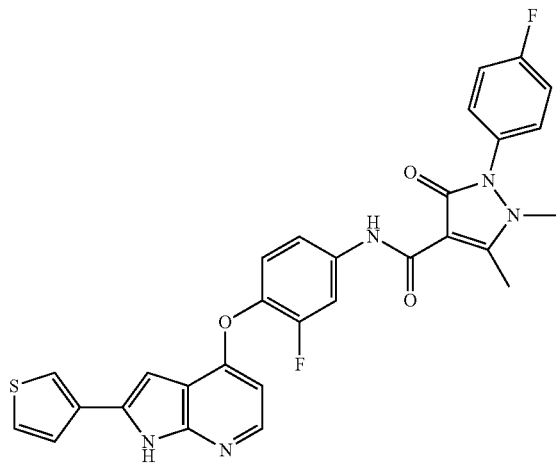 [SMILES: Cc1c(C(=O)Nc2ccc(Oc3ccnc4[nH]c(-c5ccsc5)cc34)c(F)c2)c(=O)n(-c2ccc(F)cc2)n1C]

The target compound N-(3-fluoro-4-(2-(thiophen-3-yl)-1H-pyrrolo[2,3-b]pyridin-4-yloxy)phenyl)-2-(4-fluorophenyl)-1,5-dimethyl-3-oxo-2,3-dihydro-1H-pyrazole-4-carboxamide was prepared in the same manner as Example 10.
MS (ESI pos. ion) m/z: 558 (MH+). Calc'd exact mass for C29H21F2N5O3S: 557.57.

Example 45

N-(3-Fluoro-4-(2-(4-methoxyphenyl)-1H-pyrrolo[2,3-b]pyridin-4-yloxy)phenyl)-2-(4-fluorophenyl)-1,5-dimethyl-3-oxo-2,3-dihydro-1H-pyrazole-4-carboxamide

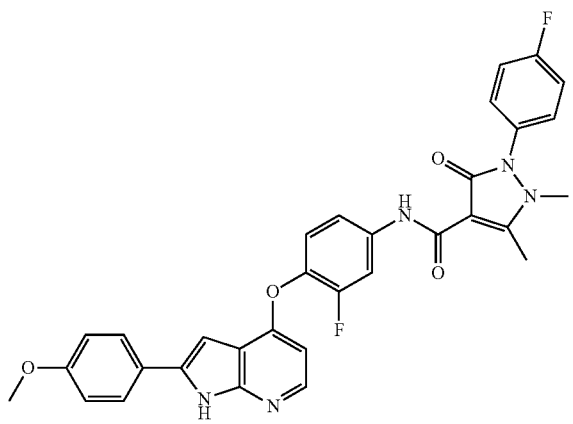

The target compound N-(3-fluoro-4-(2-(4-methoxyphenyl)-1H-pyrrolo[2,3-b]pyridin-4-yloxy) phenyl)-2-(4-fluorophenyl)-1,5-dimethyl-3-oxo-2,3-dihydro-1H-pyrazole-4-carboxamide was prepared in the same manner as Example 10.
MS (ESI pos. ion) m/z: 584 (MH+). Calc'd exact mass for C32H27F2N5O4: 583.58.

Example 46

N-(3-Fluoro-4-(2-(4-methoxyphenyl)-1H-pyrrolo[2,3-b]pyridin-4-yloxy)phenyl)-1,5-dimethyl-3-oxo-2-phenyl-2,3-dihydro-1H-pyrazole-4-carboxamide

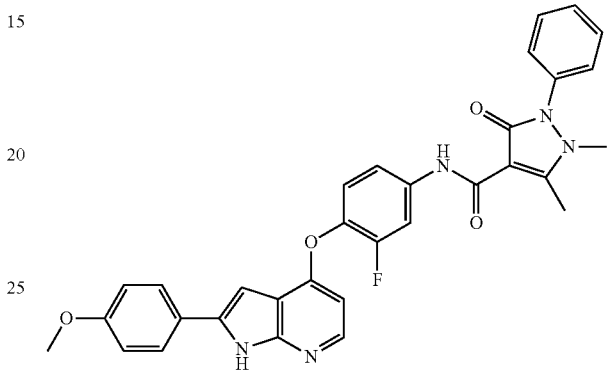

The target compound N-(3-fluoro-4-(2-(4-methoxyphenyl)-1H-pyrrolo[2,3-b]pyridin-4-yloxy)phenyl)-1,5-dimethyl-3-oxo-2-phenyl-2,3-dihydro-1H-pyrazole-4-carboxamide was prepared in the same manner as Example 10.
MS (ESI pos. ion) m/z: 566 (MH+) Calc'd exact mass for C32H28FN5O4: 565.59.

Example 47

N-(3-Fluoro-4-(2-(thiophen-3-yl)-1H-pyrrolo[2,3-b]pyridin-4-yloxy)phenyl-1,5-dimethyl-3-oxo-2-phenyl-2,3-dihydro-1H-pyrazole-4-carboxamide

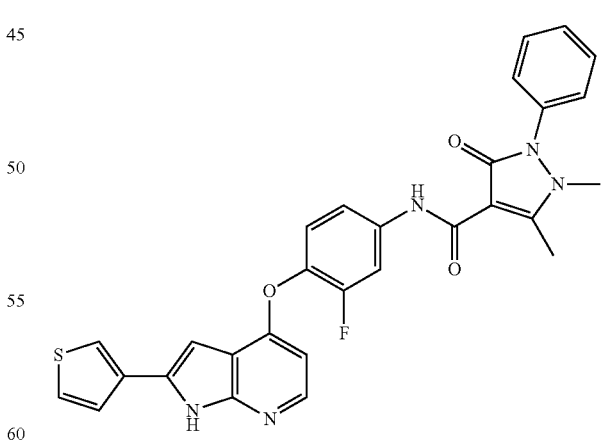

The target compound N-(3-fluoro-4-(2-(thiophen-3-yl)-1H-pyrrolo[2,3-b]pyridin-4-yloxy)phenyl)-1,5-dimethyl-3-oxo-2-phenyl-2,3-dihydro-1H-pyrazole-4-carboxamide was prepared in the same manner as Example 10.
MS (ESI pos. ion) m/z: 540 (MH+). Calc'd exact mass for C29H22FN5O3S: 539.58.

Example 48

N-(3-Fluoro-4-(2-(thiophen-2-yl)-1H-pyrrolo[2,3-b]pyridin-4-yloxy)phenyl)-1,5-dimethyl-3-oxo-2-phenyl-2,3-dihydro-1H-pyrazole-4-carboxamide

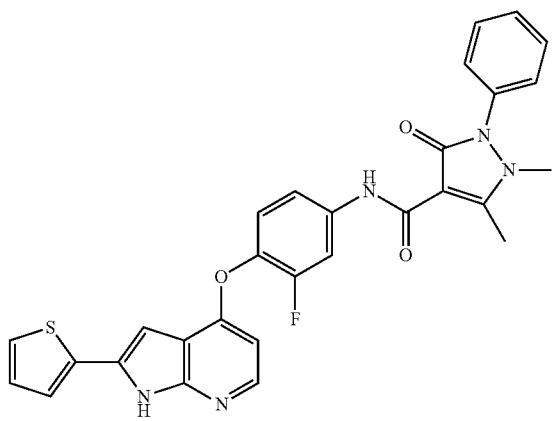 [SMILES: Cc1c(C(=O)Nc2ccc(Oc3ccnc4[nH]c(-c5cccs5)cc34)c(F)c2)c(=O)n(-c2ccccc2)n1C]

The target compound N-(3-fluoro-4-(2-(thiophen-2-yl)-1H-pyrrolo[2,3-b]pyridin-4-yloxy)phenyl)-1,5-dimethyl-3-oxo-2-phenyl-2,3-dihydro-1H-pyrazole-4-carboxamide was prepared in the same manner as Example 10.

MS (ESI pos. ion) m/z: 540 (MH$^+$). Calc'd exact mass for $C_{29}H_{22}FN_5O_3S$: 539.58.

Activity Analysis

The pharmacological characteristics of the compound of the present invention may be confirmed through many pharmacological analyses. The following typical pharmacological assays were performed for the compounds according to the present invention and/or pharmaceutically acceptable salts thereof.

ELK Luciferase Assay

In order to evaluate the effect of the compounds of the present invention on the signal transduction system of the HGF receptor, c-Met, the PathDetect trans-reporting system (Stratagene Cloning Systems Inc.) was employed. After infecting Chinese hamster ovary (CHO) cells with pFR-Luc and pFA2-Elk1 plasmids (Stratagene), the cells growing in a medium containing G418 were selected to obtain stable pool. Clones responding well to the HGF signal transduction were selected using the Luciferase Assay System (Promega Corp.). The selected CHO clone was maintained in Dulbecco's modified Eagle's medium (DMEM, Invitrogen) containing 200 μg/mL G418.

Luciferase assay was carried out as follows. First, the cells were detached using PBS containing 0.5 mM EDT. The cells were added to F12 medium containing 0.1% BSA. The cells were transferred to a 96-well plate treated with poly-D-lysine, at about 45000 cells per well. After culturing the cells for about 16 hours, followed by treating with HGF (Cell Signal) diluted in F12-BSA medium, 10 mL each well, the cells were further cultured for about 4 to 6 hours. In order to measure luciferase activity, Bright-Glo (60 mL, Promega) was added and then luminescence was measured using Victor2 (Perkin Elmer). For testing of the efficiency of the compounds, HGF was used at a final concentration of 50 ng/mL. After adding the compound diluted in F12-BSA medium, 10 μL each well, and waiting for 10 minutes, 350 ng/mL HGF (10 μL) was added. After culturing for 4 to 6 hours, luciferase activity was measured according to the same procedure. For result analysis, plotting was carried out using the Prism software (GraphPad Software, Inc.) and IC$_{50}$ was measured.

The compounds of the present invention have IC$_{50}$ values for c-Met kinase of 0.001 to 2 μM. More preferred compounds have an IC$_{50}$ value less than 1.0 μM, more preferably less than about 0.5 μM. Table 1 shows the activity analysis result for some compounds of the present invention.

cMet ELISA Assay

To measure the potency of compounds to inhibit HGF signaling through cMet in cells expressing human cMet endogenously, sandwich ELISA was used to detect phosphorylated cMet. A549 cells or other cells were plated in 96 well plate at 50,000 cells per well in 100 ul volume of growth media (DMEM containing 10% FBS). After overnight growth, the medium was replaced with assay media (F-12 containing 0.1% BSA). The next day, compounds were serially diluted in assay media, and added to the wells for 10 minutes. Then cells were activated with HGF at 500 ug/ml final concentration for 15 minutes. After a brief wash, cells were lysed with lysis buffer containing protease and phosphatase inhibitor (Cell Signal) and extract was harvested.

Then, the cell extract was added to an ELISA plate that had been coated with anti-cMET antibody (Cell Signal). After washing and reacting with anti-phospho-cMET antibody (Cell Signal), the cell extract was further incubated using HRP-labeled secondary antibody. The degree of phosphorylation of cMET was detected by adding LumiGlo (KPL).

The ELISA assay result for some compounds of the present invention is also shown in Table 1.

TABLE 1

| Example Number | Luciferase, IC$_{50}$ (−M) | ELISA, IC$_{50}$ (−M) |
|---|---|---|
| 1 | 0.679 | 0.929 |
| 2 | 0.099 | 0.522 |
| 3 | 0.492 | 0.159 |
| 4 | 0.055 | 0.369 |
| 5 | 0.354 | 2.653 |
| 6 | 0.236 | 0.256 |
| 7 | 0.410 | 0.513 |
| 8 | 0.030 | 0.119 |
| 9 | 0.205 | 0.320 |
| 10 | 0.016 | 0.232 |
| 11 | 0.008 | 0.311 |
| 12 | 0.008 | 0.225 |
| 13 | 0.242 | |
| 14 | 4.288 | 3.022 |
| 15 | 0.373 | |
| 16 | 1.743 | 3.508 |
| 17 | 2.297 | 8.443 |
| 18 | 2.000 | |
| 19 | 2.045 | 0.510 |
| 20 | 0.096 | 0.070 |
| 21 | 0.186 | 0.264 |
| 22 | 0.069 | 0.074 |
| 23 | 0.055 | 0.062 |
| 24 | 0.036 | 0.041 |
| 25 | 0.738 | 0.264 |
| 26 | 0.050 | 0.058 |
| 27 | 0.042 | 0.048 |
| 28 | 0.035 | 0.239 |
| 29 | 0.144 | 0.137 |
| 30 | 0.061 | 0.081 |
| 31 | 0.074 | 0.081 |
| 32 | 1.842 | |
| 33 | 1.426 | |
| 34 | 2.259 | |
| 35 | 2.438 | |
| 36 | 0.089 | 0.126 |
| 37 | 0.008 | 0.148 |
| 38 | 0.393 | 0.358 |
| 39 | 0.345 | 0.248 |

TABLE 1-continued

| Example Number | Luciferase, IC$_{50}$ (−M) | ELISA, IC$_{50}$ (−M) |
|---|---|---|
| 40 | 0.040 | 0.118 |
| 41 | 0.518 | |
| 42 | 1.048 | |
| 43 | 0.036 | 0.203 |
| 44 | 0.027 | 0.138 |
| 45 | 0.052 | 0.711 |
| 46 | 0.041 | 0.288 |
| 47 | 0.056 | 0.203 |
| 48 | 0.228 | 0.249 |

The foregoing examples are for illustrative purposes only and are not intended to limit the present invention to the compounds described therein. Modifications and changes obvious to those skilled in the art are also within the scope of the present invention as set forth in the appended claims.

Those skilled in the art will easily understand the essential features of the present invention from the foregoing description and may make various changes and modifications of the present invention to meet various applications and conditions without departing from the spirit and scope of the present invention.

As long as the compound of the present invention is administered according to the present invention, no forbidden toxic effect is expected.

All the cited references, patents, patent applications and patent publications are incorporated herein by reference.

The invention claimed is:

1. A compound represented by Chemical Formula 1, or a pharmaceutically acceptable salt or a stereoisomer thereof:

[Chemical Formula 1]

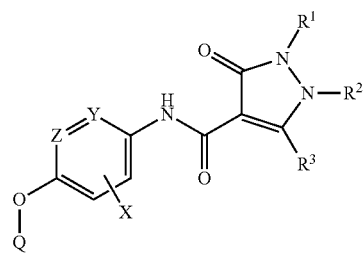

wherein
R$^1$ is aryl, or aryl substituted with halogen;
R$^2$ is C$_1$-C$_6$ alkyl;
R$^3$ is C$_1$-C$_{12}$ alkyl;
Q is

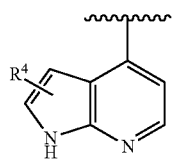

X is hydrogen or halogen;
Y is CH; and
Z is CH;
wherein the structures above,
R$^4$ is aryl, aryl substituted with alkoxy, unsaturated heterocyclyl, or a pharmaceutically acceptable salt or a stereoisomer thereof.

2. The compound according to claim 1, wherein R$^1$ is C$_6$-C$_{10}$ aryl, or C$_6$-C$_{10}$ aryl substituted with halogen, or a pharmaceutically acceptable salt or a stereoisomer thereof.

3. The compound according to claim 2, wherein R$^1$ is phenyl, or phenyl substituted with halogen, or a pharmaceutically acceptable salt or a stereoisomer thereof.

4. The compound according to claim 1, wherein R$^3$ is C$_1$-C$_6$ alkyl, or a pharmaceutically acceptable salt or a stereoisomer thereof.

5. The compound according to claim 1, wherein X is halogen selected from the group consisting of F, Cl, Br and I, or a pharmaceutically acceptable salt or a stereoisomer thereof.

6. The compound according to claim 1, wherein R$^4$ is C$_6$-C$_{10}$ aryl, C$_6$-C$_{10}$ aryl substituted with C$_1$-C$_6$ alkoxy, or 3- to 10-membered unsaturated heterocyclyl having one or more heteroatom(s) selected from the group consisting of N, S and O, or a pharmaceutically acceptable salt or a stereoisomer thereof.

7. The compound according to claim 6, wherein R$^4$ is phenyl, phenyl substituted with C$_1$-C$_6$ alkoxy, naphthyl, pyridyl, pyrimidinyl, pyrazolyl, thiazolyl, thiophenyl, isoxazolyl, or a pharmaceutically acceptable salt or a stereoisomer thereof.

8. The compound according to claim 1, which is selected from the group consisting of:
1,5-dimethyl-3-oxo-2-phenyl-2,3-dihydro-1H-pyrazole-4-carboxylic acid [3-fluoro-4-(2-phenyl-1H-pyrrolo[2,3-b]pyridin-4-yloxy)-phenyl]-amide;
2-(4-fluoro-phenyl)-1,5-dimethyl-3-oxo-2,3-dihydro-1H-pyrazole-4-carboxylic acid [3-fluoro-4-(2-phenyl-1H-pyrrolo[2,3-b]pyridin-4-yloxy)-phenyl]-amide;
2-(4-fluoro-phenyl)-1,5-dimethyl-3-oxo-2,3-dihydro-1H-pyrazole-4-carboxylic acid [3-fluoro-4-(3-phenyl-1H-pyrrolo[2,3-b]pyridin-4-yloxy)-phenyl]-amide;
N-(3-fluoro-4-(2-(thiophen-2-yl)-1H-pyrrolo[2,3-b]pyridin-4-yloxy)phenyl)-2-(4-fluorophenyl)-1,5-dimethyl-3-oxo-2,3-dihydro-1H-pyrazole-4-carboxamide;
N-(3-fluoro-4-(2-(thiophen-3-yl)-1H-pyrrolo[2,3-b]pyridin-4-yloxy)phenyl)-2-(4-fluorophenyl)-1,5-dimethyl-3-oxo-2,3-dihydro-1H-pyrazole-4-carboxamide;
N-(3-fluoro-4-(2-(4-methoxyphenyl)-1H-pyrrolo[2,3-b]pyridin-4-yloxy)phenyl)-2-(4-fluorophenyl)-1.5-dimethyl-3-oxo-2,3-dihydro-1H-pyrazole-4-carboxamide;
N-(3-fluoro-4-(2-(4-methoxyphenyl)-1H-pyrrolo[2,3-b]pyridin-4-yloxy)phenyl)-1,5-dimethyl-3-oxo-2-phenyl-2,3-dihydro-1H-pyrazole-4-carboxamide;
N-(3-fluoro-4-(2-(thiophen-3-yl)-1H-pyrrolo[2,3-b]pyridin-4-yloxy)phenyl-1,5-dimethyl-3-oxo-2-phenyl-2,3-dihydro-1H-pyrazole-4-carboxamide; and
N-(3-fluoro-4-(2-(thiophen-2-yl)-1H-pyrrolo[2,3-b]pyridin-4-yloxy)phenyl)-1,5-dimethyl-3-oxo-2-phenyl-2,3-dihydro-1H-pyrazole-4-carboxamide,
or a pharmaceutically acceptable salt or a stereoisomer thereof.

9. A pharmaceutical composition comprising a therapeutically effective amount of one or more compound(s) according to claim 1, in admixture with one or more pharmaceutically acceptable carrier(s).

10. The pharmaceutical composition according to claim 9, which is for treating non-small cell lung cancer, colorectal cancer, glioblastoma, head and neck cancer, gastric cancer, bladder cancer, liver cancer, and ovarian cancer.

11. A method for treating non-small cell lung cancer, colorectal cancer, glioblastoma, head and neck cancer, gastric cancer, bladder cancer, liver cancer, and ovarian cancer as HGF-mediated disorders in a subject in need thereof, comprising administering a therapeutically effective amount of the compound according to claim 1 to the subject.

* * * * *